United States Patent [19]
Jo et al.

[11] Patent Number: 6,153,768
[45] Date of Patent: Nov. 28, 2000

[54] BENZOPYRAN DERIVATIVES

[75] Inventors: Jae Chon Jo, Suwon-shi; Sung Dae Park, Seoul; Hyun Suk Lim, Suwon-shi; Ju Su Kim, Ansan-shi; Sung Jin Kim, Inchun, all of Rep. of Korea; Kazumi Morikawa, Mishima, Japan; Yoshitake Kanbe, Gotemba, Japan; Masahiro Nishimoto, Mishima, Japan; Myung-Hwa Kim, Gotemba, Japan

[73] Assignee: C & C Research Laboratories, Kyunggi-do, Rep. of Korea

[21] Appl. No.: 09/319,616

[22] PCT Filed: Dec. 13, 1997

[86] PCT No.: PCT/KR97/00265

§ 371 Date: Jun. 8, 1999

§ 102(e) Date: Jun. 8, 1999

[87] PCT Pub. No.: WO98/25916

PCT Pub. Date: Jun. 18, 1998

[30] Foreign Application Priority Data

Dec. 13, 1996 [KR] Rep. of Korea ........................ 96-65301
Jun. 24, 1997 [KR] Rep. of Korea ........................ 97-26915

[51] Int. Cl.$^7$ .................................................. C07D 311/04
[52] U.S. Cl. .......................... 549/406; 514/336; 514/422; 514/456; 548/525; 546/282.1
[58] Field of Search ........................ 546/282.1; 548/525; 549/406; 514/336, 422, 456

[56] References Cited

U.S. PATENT DOCUMENTS 4,904,661 2/1990 Pilgrim et al. ........................ 514/237.5

FOREIGN PATENT DOCUMENTS

WO 93/10741 6/1993 WIPO .

OTHER PUBLICATIONS

Chemical Abstracts, vol. 110, p. 718, (1989).
Jacobsen, P. et al. "Preparation of Novel Cis–3,4–Chroman Derivatives Useful in the Prevention or Treatment of Estrogen Related Diseases or Syndromes" CA 129:4579 (1998).
Jacobsen, P. et al. "Novel (–)–Enatomers of Cis–3,4–Chroman Derivaties Useful in the Prevention or Treatment of Estrogen Related Diseases or Syndromes" CA 129:4522 (1998).

*Primary Examiner*—Amelia Owens
*Attorney, Agent, or Firm*—Peter F. Corless; Edwards & Angell, LLP

[57] ABSTRACT

The present invention relates to a novel benzopyran derivative having anti-estrogenic activity. More specifically, the present invention relates to a novel benzopyran derivative represented by formula (I) and pharmaceutically acceptable salt thereof, in which ----- represents a single bond or a double bond; R1 and R2 independently of one another represent hydrogen, hydroxy or OR group, wherein R represents acyl or alkyl; R3 represents hydrogen, lower alkyl or halogeno lower alkyl, provided that when ----- represents a double bond, R3 is not present; R4 represents hydrogen or lower alkyl; A represents a group of formula a, b, c or d; R5, R6 and R7 independently of one another represent hydrogen, alkyl, halogenoalkyl, alkenyl or halogenoalkenyl, or R6 and R7 together with nitrogen atom to which they are bound can form a 4- to 8-membered heterocyclic ring which can be substituted with R5; X represents O, S, or NR8, wherein R8 represents hydrogen or lower alkyl; m denotes an integer of 2 to 15; n denotes an integer of 0 to 2; and p denotes an integer of 0 to 4.

16 Claims, No Drawings

BENZOPYRAN DERIVATIVES

TECHNICAL FIELD

The present invention relates to a novel benzopyran derivative having anti-estrogenic activity. More specifically, the present invention relates to a novel benzopyran derivative represented by formula (I):

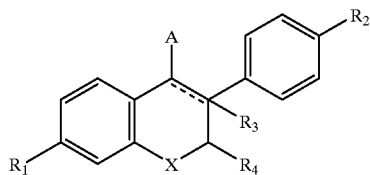

and pharmaceutically acceptable salt thereof, in which
- ----- represents a single bond or a double bond;
- $R_1$ and $R_2$ independently of one another represent hydrogen, hydroxy or OR group, wherein R represents acyl or alkyl;
- $R_3$ represents hydrogen, lower alkyl or halogeno lower alkyl, provided that when ----- represents a double bond, $R_3$ is not present;
- $R_4$ represents hydrogen or lower alkyl;
- A represents a group of formula (a), (b), (c) or (d);

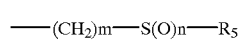 (a)

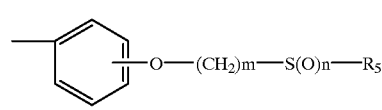 (b)

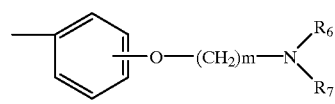 (c)

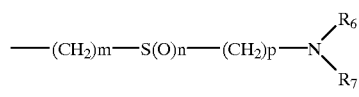 (d)

- $R_5$, $R_6$ and $R_7$ independently of one another represent hydrogen, alkyl, halogenoalkyl, alkenyl or halogenoalkenyl, or
- $R_6$ and $R_7$ together with nitrogen atom to which they are bound can form a 4- to 8-membered heterocyclic ring which can be substituted with $R_5$;
- X represents O, S or $NR_8$, wherein $R_8$ represents hydrogen or lower alkyl;
- m denotes an integer of 2 to 15;
- n denotes an integer of 0 to 2; and
- p denotes an integer of 0 to 4, and to a process for preparation thereof and a pharmaceutical composition having anti-estrogenic activity which contains the compound (I) as an active component.

BACKGROUND ART

In treating diseases caused by the abnormal tissue growth depending on a certain sexual steroidal hormone such as estrogen, it is very important to significantly inhibit, if possible, to completely remove the effect induced by said sexual steroidal hormone. For this purpose, it is desirable to block the receptor site which can be stimulated by sexual steroidal hormone and further, to reduce the level of sexual steroidal hormone capable of acting on said receptor site. For instance, as a substitution or combined therapy, administration of anti-estrogenic agents to limit the production of estrogen to the amount less than required to activate the receptor site may be used. However, prior methods for blocking the estrogen production could not sufficiently inhibit the effect induced through estrogen receptor. Practically, even when estrogen is completely absent, some of the receptors may be activated. Accordingly, it was considered that antagonists for estrogen can provide better therapeutic effect in comparison to the method for blocking only the production of sexual steroidal hormone. Thus, numerous anti-estrogenic compounds have been developed. For example, many patent publications including U.S. Pat. Nos. 4,760,061, 4,732,912, 4,904,661 and 5,395,842 and WO 96/22092, etc. disclose various anti-estrogenic compounds. However, prior antagonists have sometimes insufficient affinity to the receptors. In some cases, moreover, they can combine to the receptor but act themselves as agonists, and therefore, activate rather than block the receptor. For example, Tamoxifen has been most widely used as an anti-estrogenic agent. However, it has a disadvantage that it exhibits estrogenic activity in some organs (see, M. Harper and A. Walpole, J. Reprod. Fertil., 1967, 13, 101). Therefore, it is required to develop the anti-estrogenic compound which has substantially or completely no agonistic effect and can effectively block the estrogenic receptor.

In addition, it has been known that 7 α-substituted derivatives of estradiol, for example, 7 α—$(CH_2)_{10}$CONMeBu derivative, exhibit anti-estrogenic activity (see, EP Appl. 0138504, U.S. Pat. No. 4,659,516). Further, estradiol derivative having —$(CH_2)_9SOC_5H_6F_5$ substituent has also been disclosed (see, Wakeling et al., Cancer Res., 1991, 51, 3867) as steroidal anti-estrogen without agonistic effect.

Non-steroidal anti-estrogenic drug without agonistic effect has been first reported by Wakeling et al. in 1987 (see, A. Wakeling and J. Bowler, J. Endocrinol., 1987, 112, R7). Meanwhile, U.S. Pat. No. 4,904,661 (ICI, Great Britain) discloses a phenol derivative having anti-estrogenic activity. This phenol derivative generally has a naphthalene structure and includes, typically, the following compounds:

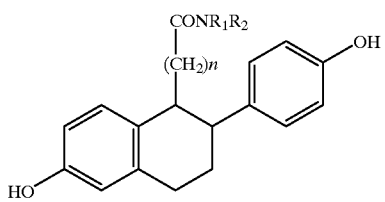

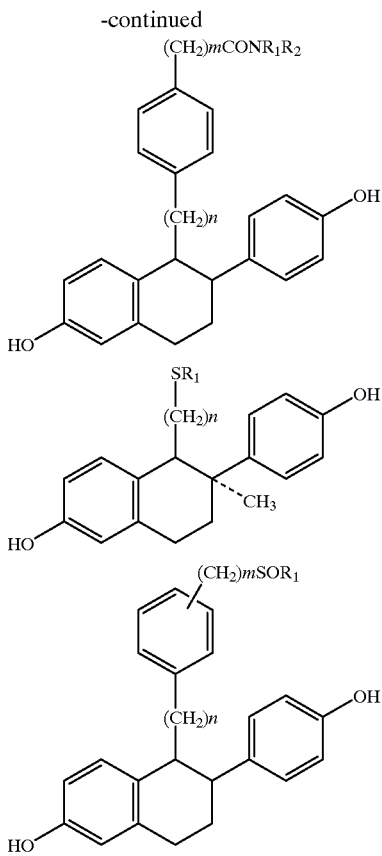

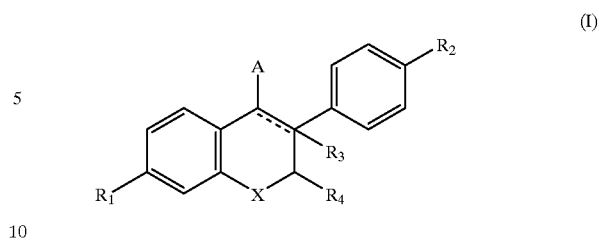

and pharmaceutically acceptable salt thereof, in which
----- represents a single bond or a double bond;
$R_1$ and $R_2$ independently of one another represent hydrogen, hydroxy or OR group, wherein R represents acyl or alkyl;
$R_3$ represents hydrogen, lower alkyl or halogeno lower alkyl, provided that when ----- represents a double bond, $R_3$ is not present;
$R_4$ represents hydrogen or lower alkyl;
A represents a group of formula (a), (b), (c) or (d);

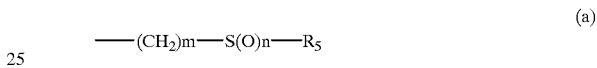

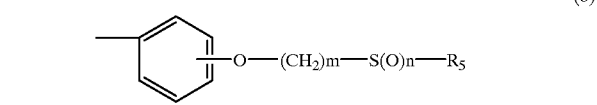

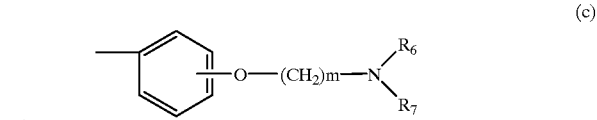

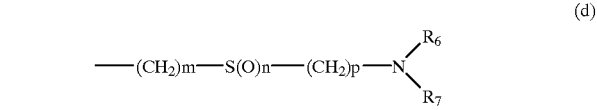

$R_5$, $R_6$ and $R_7$ independently of one another represent hydrogen, alkyl, halogenoalkyl, alkenyl or halogenoalkenyl, or
$R_6$ and $R_7$ together with nitrogen atom to which they are bound can form a 4- to 8-membered heterocyclic ring which can be substituted with $R_5$;
X represents O, S or $NR_8$, wherein $R_8$ represents hydrogen or lower alkyl;
m denotes an integer of 2 to 15;
n denotes an integer of 0 to 2; and
p denotes an integer of 0 to 4.

In addition, the present invention also relates to a process for preparing the benzopyran derivative of formula (I).

Further, the present invention relates to a pharmaceutical composition having anti-estrogenic activity, which contains the compound of formula (I) as an active component.

BEST MODE FOR CARRYING OUT THE INVENTION

In the present specification, the term "lower alkyl" denotes straight or branched saturated hydrocarbon radicals having 1 to 6, preferably 1 to 4, carbon atoms; the term "halogeno lower alkyl" denotes straight or branched saturated hydrocarbon radicals having 1 to 6, preferably 1 to 4, carbon atoms and 1 to 9, preferably 1 to 5, halogen atoms As other non-steroidal anti-estrogenic compounds, WO 93/10741 discloses benzopyran derivatives having aminoethoxyphenyl substituent (Endore-cherche), of which the typical compound is EM-343 having the following structure:

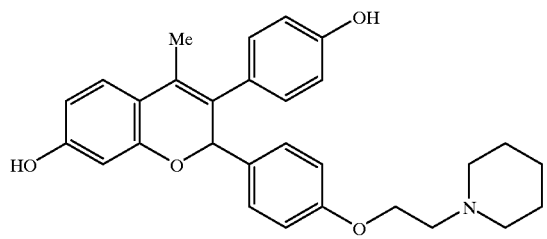

Accordingly, the present inventors have researched the anti-estrogenic activity of compounds having various structures. As a result, we have identified that the benzopyran derivatives represented by formula (I), as defined above, can exhibit a good anti-estrogenic activity without agonistic activity, to be expected no undesirable side effect and thus, completed the present invention.

DISCLOSURE OF THE INVENTION

Therefore, the present invention relates to a novel benzopyran derivative represented by formula (I):

such as fluorine, chlorine, bromine, etc, preferably fluorine atom; the term "alkyl" denotes straight or branched saturated hydrocarbon radicals having 1 to 10, preferably 1 to 6, carbon atoms including lower alkyl as defined above; and the term "alkenyl" denotes straight or branched hydrocarbon radicals having 2 to 10, preferably 2 to 6, carbon atoms and one or more double bond(s). Further, the term "4- to 8-membered heterocyclic ring" denotes saturated or unsaturated heteromonocyclic ring which can contain 1 to 4 nitrogen atoms and includes, for example, pyrrolyl, pyrrolinyl, imidazolyl, pyrazolyl, pyridyl, pyrimidinyl, pyrazinyl, triazinyl, pyridazinyl, triazolyl, tetrazolyl, piperazinyl, piperidino, pyrrolidinyl, imidazolidinyl, etc.

In the compound of formula (I) according to the present invention, preferably $R_1$ and $R_2$ independently of one another represent hydrogen, hydroxy or OR wherein R represents acyl or alkyl, $R_3$ represents hydrogen, $C_1$–$C_4$ lower alkyl or halogeno-$C_1$–$C_4$ lower alkyl, $R_4$ represents hydrogen or $C_1$–$C_4$ lower alkyl, A represents a group of formula (a), (b), (c) or (d), $R_5$, $R_6$ and $R_7$ independently of one another represent hydrogen, $C_1$–$C_6$ alkyl, halogeno-$C_1$–$C_6$ alkyl, $C_2$–$C_6$ alkenyl or halogeno-$C_2$–$C_6$ alkenyl, or $R_6$ and $R_7$ together with nitrogen atom to which they are bound can form a 5- to 6-membered heterocyclic ring which can contain 1 to 2 nitrogen atoms and can be substituted with halogeno-$C_1$–$C_6$ alkyl, X represents O, S or $NR_8$, wherein $R_8$ represents hydrogen or $C_1$–$C_4$ lower alkyl, m denotes an integer of 4 to 12, n denotes an integer of 0 to 2 and p denotes an integer of 1 to 3.

Particularly preferable compound of formula (I) according to the present invention includes those wherein $R_1$ and $R_2$ independently of one another represent hydrogen or hydroxy, $R_3$ represents hydrogen or $C_1$–$C_2$ lower alkyl, $R_4$ represents hydrogen or $C_1$–$C_2$ lower alkyl, A represents a group of formula (a), (b), (c) or (d), $R_5$, $R_6$ and $R_7$ independently of one another represents hydrogen, $C_1$–$C_6$ alkyl or halogeno-$C_1$–$C_6$ alkyl, or $R_6$ and $R_7$ together with nitrogen atom to which they are bound can form piperazinyl or piperidino group which can be substituted with halogeno-$C_1$–$C_6$ alkyl, X represents O or S, m denotes an integer of 4 to 12, n denotes an integer of 0 to 2 and p denotes an integer of 2.

As specific example of the compound of formula (I) according to the present invention, the following compounds can be mentioned:

(3RS,4RS)-7-hydroxy-3-(4-hydroxyphenyl)-3-methyl-4-[9-(4,4,5,5,5-pentafluoropentylthio)nonyl]-2,3-dihydro-4H-benzopyran;

(3RS,4RS)-7-hydroxy-3-(4-hydroxyphenyl)-3-methyl-4-[9-(4,4,5,5,5-pentafluoropentylsulfinyl)nonyl]-2,3-dihydro-4H-benzopyran;

(3RS,4RS)-7-hydroxy-3-(4-hydroxyphenyl)-3-methyl-4-[8-(4,4,5,5,5-pentafluoropentylthio)octyl]-2,3-dihydro-4H-benzopyran;

(3RS,4RS)-7-hydroxy-3-(4-hydroxyphenyl)-3-methyl-4-[8-(4,4,5,5,5-pentafluoropentylsulfinyl)octyl]-2,3-dihydro-4H-benzopyran;

(3RS,4RS)-7-hydroxy-3-(4-hydroxyphenyl)-3-methyl-4-[9-(4,4,5,5,5-pentafluoropentylsulfonyl)nonyl]-2,3-dihydro-4H-benzopyran;

7-hydroxy-3-(4-hydroxyphenyl)-4-[4-(5-(4,4,5,5,5-pentafluoropentylthio)pentyloxy)phenyl]-2H-benzopyran;

(3RS,4RS)-7-hydroxy-3-(4-hydroxyphenyl)-3-methyl-4-[9-(4,4,5,5,5-pentafluoropentylsulfinyl)nonyl]-thiochroman;

(3RS,4RS)-7-hydroxy-3-(4-hydroxyphenyl)-3-methyl-4-[3-(4-(4,4,5,5,5-pentafluoropentylthio)butyloxy)phenyl]-2,3-dihydro-4H-benzopyran;

(3RS,4RS)-7-hydroxy-3-(4-hydroxyphenyl)-3-methyl-4-[3 (4-(4,4,5,5,5-pentafluoropentylsulfinyl)butyloxy) phenyl]-2,3-dihydro-4H-benzopyran;

(3RS,4RS)-7-hydroxy-3-(4-hydroxyphenyl)-3-methyl-4-[3-(4-(4,4,5,5,5-pentafluoropentylsulfonyl)butyloxy) phenyl]-2,3-dihydro-4H-benzopyran;

(3RS,4RS)-7-hydroxy-3-(4-hydroxyphenyl)-3-methyl-4-[9-(2-piperidinoethylthio)nonyl]-2,3-dihydro-4H-benzopyran;

(3RS,4RS)-7-hydroxy-3-(4-hydroxyphenyl)-3-methyl-4-[9-(2-piperidinoethylsulfinyl)nonyl]-2,3-dihydro-4H-benzopyran;

(3RS,4RS)-7-hydroxy-3-(4-hydroxyphenyl)-3-methyl-4-[3-(5-(4,4,5,5,5-pentafluoropentylthio)pentyloxy)phenyl]-2,3-dihydro-4H-benzopyran;

(3RS,4RS)-7-hydroxy-3-(4-hydroxyphenyl)-3-methyl-4-[3-(5-(4,4,5,5,5-pentafluoropentylsulfinyl)pentyloxy) phenyl]-2,3-dihydro-4H-benzopyran;

(3RS,4RS)-7-hydroxy-3-(4-hydroxyphenyl)-3-methyl-4-[3-(5-(4,4,5,5,5-pentafluoropentylsulfonyl)pentyloxy) phenyl]-2,3-dihydro-4H-benzopyran;

(3RS,4RS)-7-hydroxy-3-(4-hydroxyphenyl)-3-methyl-4-[4-(piperidinoetliyloxy)phenyl]-2,3-dihydro-4H-benzopyran;

(3RS,4RS)-7-hydroxy-3-(4-hydroxyphenyl)-3-methyl-4-[4-(5-(4,4,5,5,5-pentafluoropentylsulfonyl)pentyloxy) phenyl]thiochroman;

(3RS,4RS)-7-hydroxy-3-(4-hydroxyphenyl)-3-methyl-4-[4-(4-piperidinobutyloxy)phenyl]thiochroman or its hydrochloride;

(3RS,4RS)-7-hydroxy-3-(4-hydroxyphenyl)-3-methyl-4-{4-[2-(4-(4,4,5,5,5-pentafluoropentyl)piperazino)ethyloxy] phenyl}thiochroman dihydrochloride;

(3RS,4RS)-7-hydroxy-3-(4-hydroxyphenyl)-3-methyl-4-[8-(4,4,5,5,5-pentafluoropentylsulfinyl)octyl]thiochroman;

(3RS,4RS)-7-hydroxy-3-(4-hydroxyphenyl)-3-methyl-4-[10-(4,4,5,5,5-pentafluoropentylsulfinyl)decyl] thiochroman;

(3RS,4RS)-7-hydroxy-3-phenyl-3-methyl-4-[9-(4,4,5,5,5-pentafluoropentylsulfinyl)nonyl]thiochroman;

(3RS,4RS)-3-(4-hydroxyphenyl)-3-methyl-4-[9-(4,4,5,,5,-pentafluoropentylsulfinyl)nonyl]thiochroman;

(3RS,4RS)-7-methoxy-3-(4-methoxyphenyl)-3-methyl-4-(9-pentylthiononyl)thiochroman;

(3RS,4RS)-7-hydroxy-3-(4-hydroxyphenyl)-3-methyl-4-(9-pentylthiononyl)thiochroman;

(3RS,4RS)-7-hydroxy-3-(4-hydroxyphenyl)-3-methyl-4-(9-pentylsulfinynonyl)thiochroman;

(3RS,4RS)-7-hydroxy-3-(4-hydroxyphenyl)-3-methyl-4-[9-(4,4,5,5,5-pentafluoropentylthio)nonyl]thiochroman; and (3RS,4RS)-7-hydroxy-3-(4-hydroxyphenyl)-3-methyl-4-[9-(4,4,5,5,5-pentafluoropentylsulfinyl)nonyl]thiochroman.

The present invention also provides a process for preparing the compound of formula (I) as defined above. According to the present invention, the compound of formula (I) can be prepared by a method depicted in anyone of the following reaction schemes I, II, III, IV, V, VI and VII.

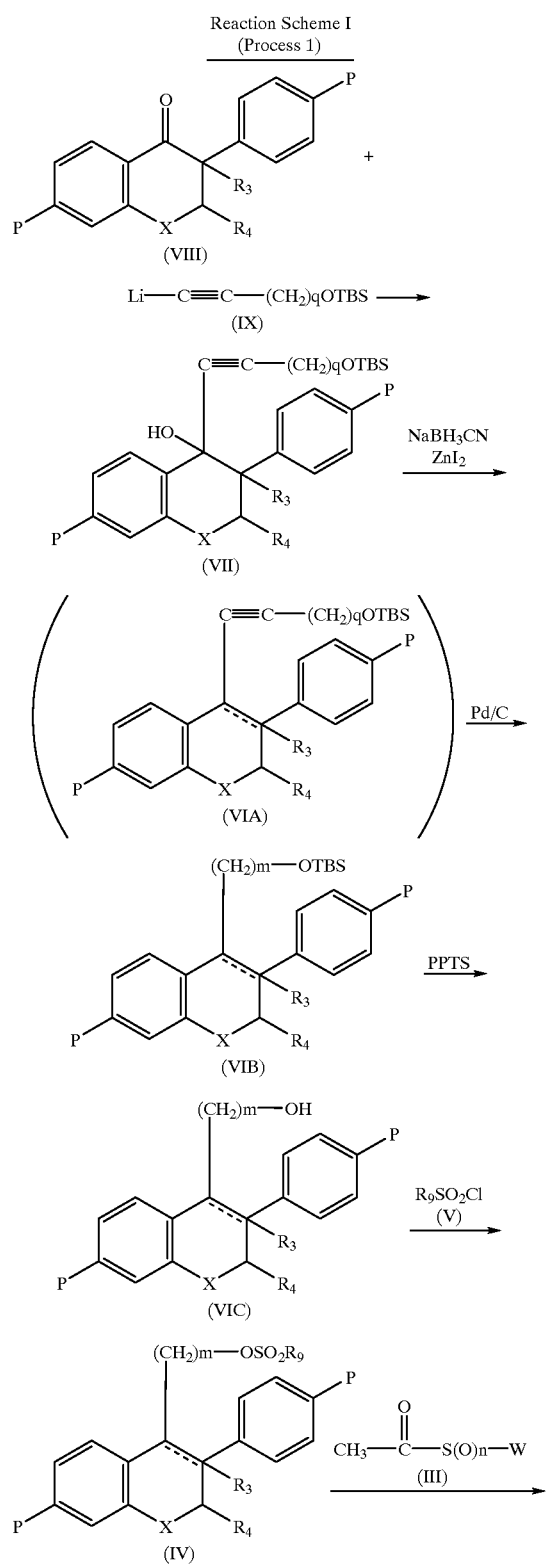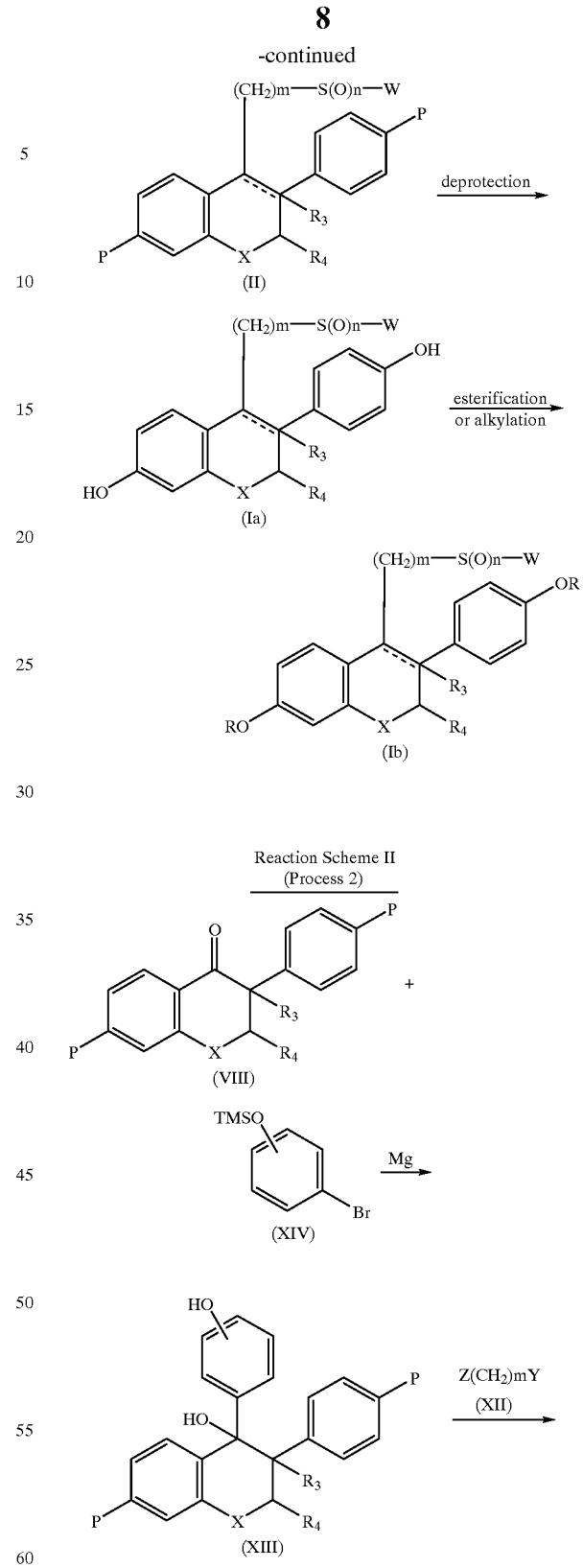

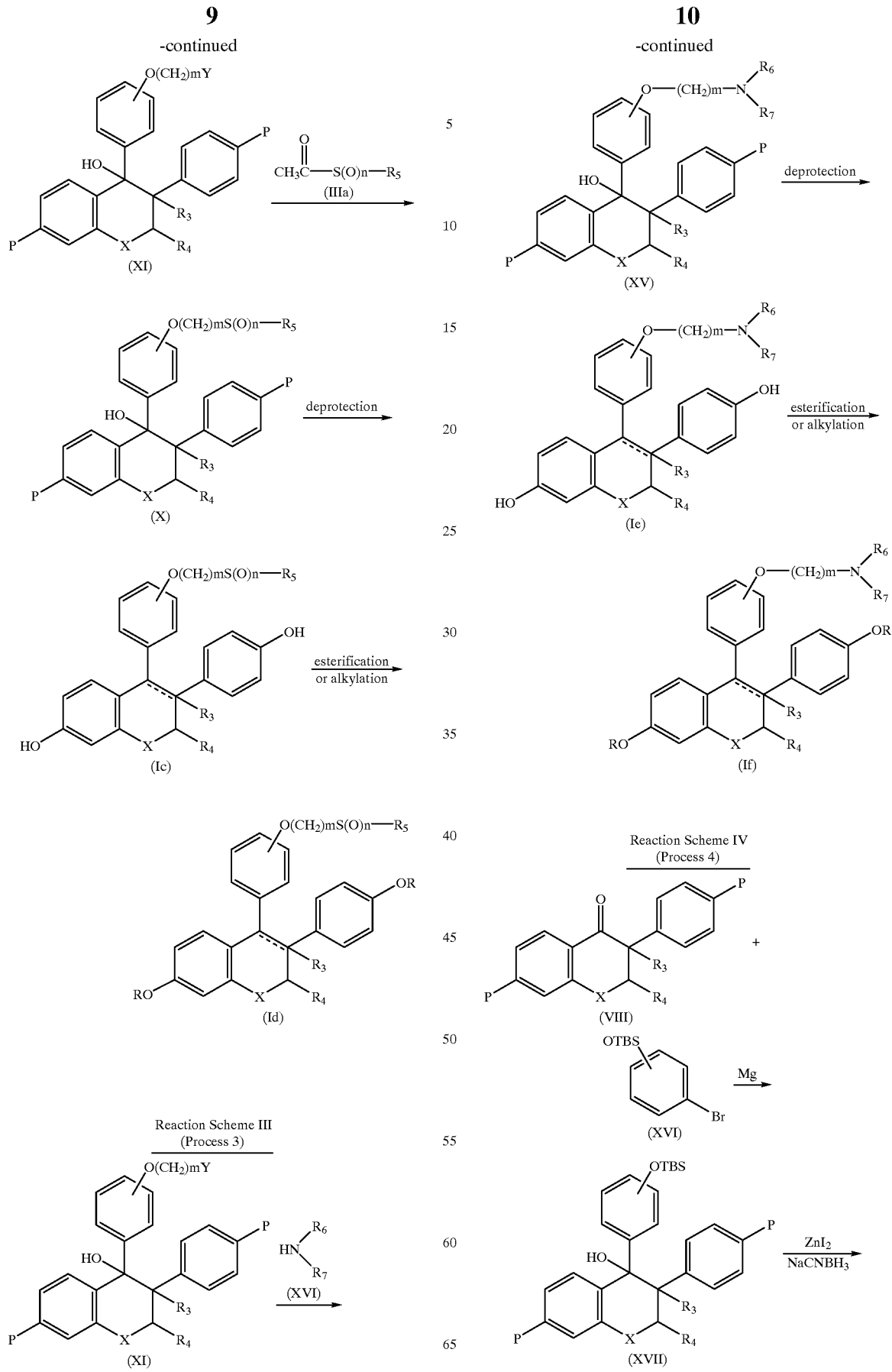

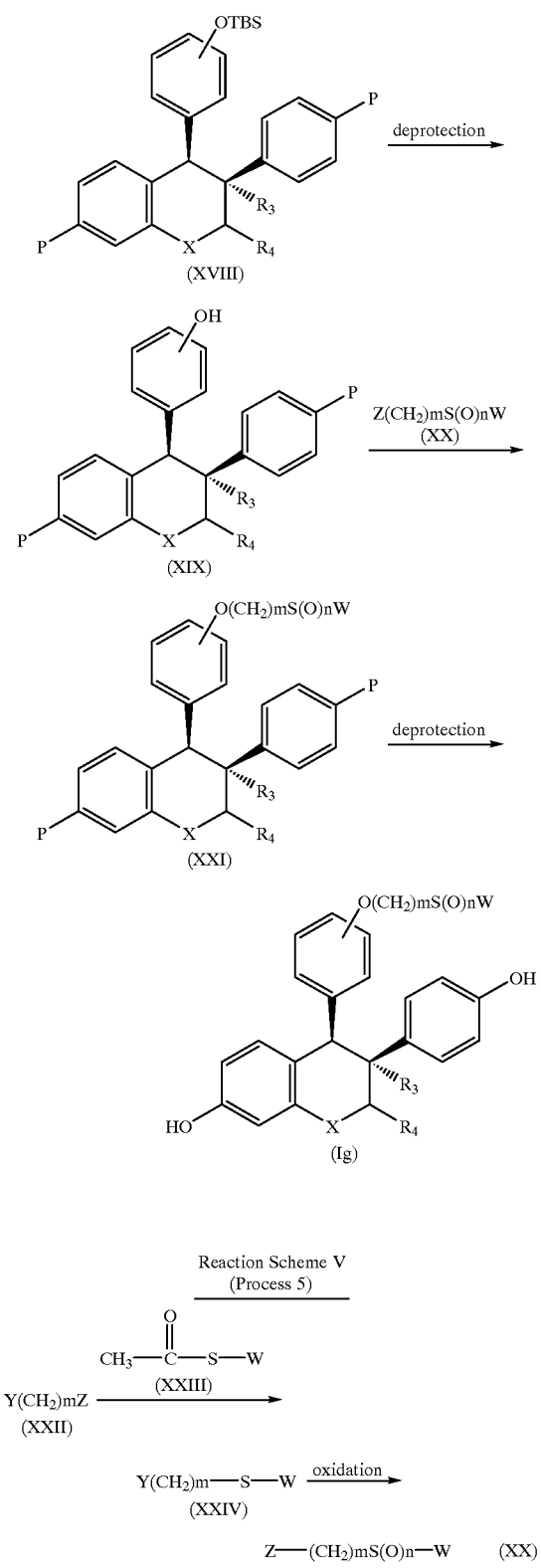

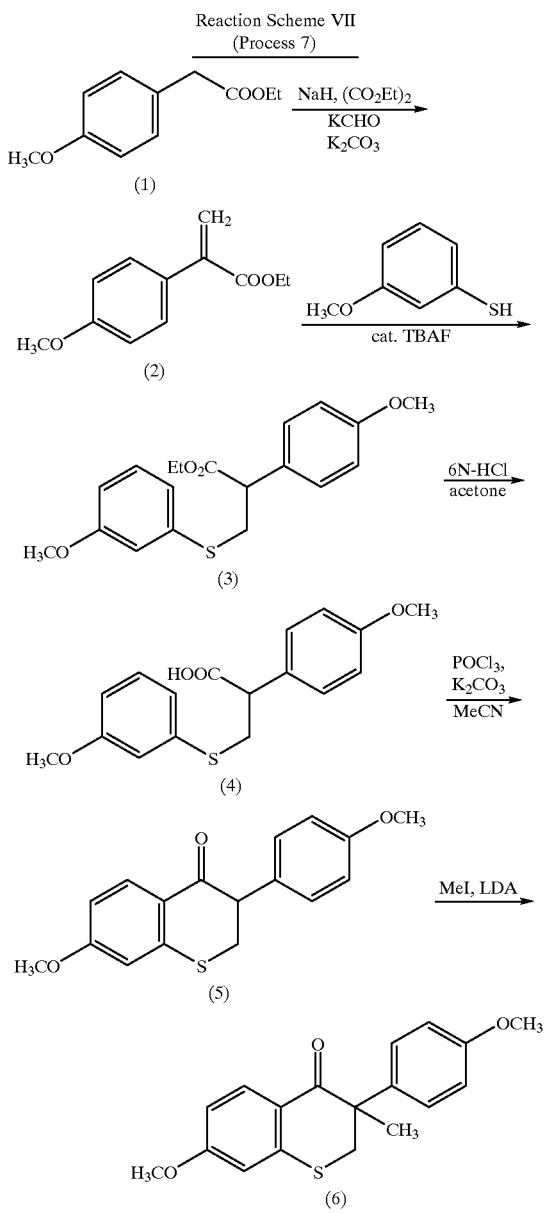

Reaction Scheme VII
(Process 7)

In the above reaction schemes I, II, III, IV, V, VI and VII
R, R$_1$ to R$_8$, X, m and n are defined as in formula (I),
R$_9$ represents methyl or tolyl,
P represents hydrogen or hydroxy protected by a conventional hydroxy-protecting group such as methoxymethyl or t-butyldimthylsilyl,
W represents R$_5$ or

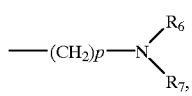

wherein
R$_5$, R$_6$, R$_7$ and p are defined as in formula (I),
Z represents halogen,
Y represents halogen or hydroxy,
q denotes an integer of m−2, and TBS denotes t-butyldimethylsilyl group and TMS denotes trimethylsilyl group.

Hereinafter, the process of the present invention will be more specifically explained.

Process 1

According to the process 1 of the present invention for preparing the compound of formula (I), in the first reaction step a compound of formula (VIII) is reacted with a compound of formula (IX) to produce a compound of formula (VII). This reaction can preferably be carried out in the presence of a solvent. Although any of organic solvents which do not adversely affect the reaction can be used as the solvent in this reaction, the reaction is preferably carried out in the solvent such as tetrahydrofuran, ethyl ether, dioxane, hexane, etc., with tetrahydrofuran being particularly preferable. The reaction is preferably conducted under anhydrous condition. The reaction temperature is not specifically limited and the reaction can be generally carried out under cooling to warming, preferably at room temperature.

In the second reaction step, the compound of formula (VII) produced in the first reaction step is reduced to produce a compound of formula (VIC). This reduction can be practiced by means of any of conventional reduction methods, for example, using a combination of metal and organic or inorganic acid or by catalytic reduction in the presence of a metallic catalyst. This reaction is actually conducted in the manner that the compound (VII) is reduced with sodium cyanoborohydride and zinc iodide to produce a compound of formula (VIA) and then the compound of formula (VIA) is reduced using Pd/C to produce a compound of formula (VIB) which is then treated with pyridinium p-toulenesulfonate (PPTS) to obtain the compound (VIC).

The reaction is generally carried out in the presence of a solvent which does not adversely affect the reaction. The solvent which can be preferably used for this purpose includes, for example, ethyl acetate, methanol, ethanol, etc., with ethyl acetate being particularly preferable. The reaction temperature is not specifically limited and the reaction can be generally carried out under cooling to warming.

In the third reaction step, the compound of formula (VI) produced in the second reaction step is reacted with a compound of formula (V) to produce a compound of formula (IV). This reaction is generally carried out in the presence of a solvent which does not adversely affect the reaction. The solvent which can be preferably used for this purpose includes, for example, pyridine, dichloromethane, ethyl acetate, tetrahydrofuran, ethyl ether, chloroform, etc., with pyridine and dichloromethane being particularly preferable. The reaction temperature is not specifically limited and the reaction can be generally carried out under cooling to warming.

In the fourth reaction step, the compound of formula (IV) produced in the third reaction step is reacted with a compound of formula (III) to produce a compound of formula (II). The reaction is preferably carried out in the presence of a base. The base which can be preferably used for this purpose includes, for example, sodium hydroxide, sodium methoxide, potassium hydroxide, sodium ethoxide, etc., with sodium hydroxide being particularly preferable. The reaction is generally carried out in the presence of a solvent which does not adversely affect the reaction. The solvent which can be preferably used for this purpose includes, for example, methanol, ethanol, tetrahydrofuran, dioxane, etc., with methanol being particularly preferable.

In the fifth reaction step, the compound of formula (II) produced in the fourth reaction step wherein P represents protected hydroxy group, is subsequently deprotected to produce a compound of formula (Ia). The deprotection can be conducted according to a conventional deprotection method such as hydrolysis in the presence of acid or base, reduction, and the like.

If desired, in the sixth reaction step, the compound of formula (Ia) thus produced is alkylated or esterified according to a conventional method to produce a compound of formula (Ib) wherein R represents acyl or alkyl.

In addition, the compound of formula (I), wherein n is 0, produced according to the process 1 can be converted into the corresponding sulfinyl or sulfonyl compound wherein n is 1 or 2 according to a conventional oxidation method. As the oxidizing agent suitable for this reaction, for example, sodium periodate ($NaIO_4$), metachloroperbenzoic acid, hydrogen peroxide, oxone, etc. can be preferably used. The reaction is generally carried out in the presence of a solvent which does not adversely affect the reaction. The solvent which can be preferably used for this purpose includes, for example, methanol, dioxane, water, ethanol, tetrahydrofuran, etc.

The desired compound produced in this process can be separated and purified according to a conventional method such as column chromatography, recrystallization, etc.

Process 2

According to the process 2 of the present invention for preparing the compound of formula (I), in the first reaction step the compound of formula (VIII) is reacted with a compound of formula (XIV) to produce a compound of formula (XIII). This reaction is carried out in the presence of magnesium so that the compound (XIV) can first be reacted with magnesium to form a Grignard reagent and the resulting Grignard reagent is then reacted with the compound of formula (VIII). The reaction is generally carried out in the presence of a solvent which does not adversely affect the reaction. The solvent which can be preferably used for this purpose includes tetrahydrofuran ethyl ether, dioxane, etc. The reaction is preferably conducted under anhydrous condition. The reaction is generally carried out under cooling, preferably at −78° C. to room temperature.

In the second reaction step, the compound of formula (XIII) produced in the first reaction step is reacted with a compound of formula (XII) to produce a compound of formula (XI). This reaction is generally carried out in the presence of a solvent which does not adversely affect the reaction. The solvent which can be preferably used for this purpose includes, for example, acetone, methyl ethyl ketone, tetrahydrofuran, ethyl acetate, dioxane, etc. The reaction is generally carried out under reflux.

In view of the reaction efficiency in the next reaction step, if necessary, it may be preferable to convert the compound wherein Y is hydroxy or halogen such as chloro, except iodo, into the compound wherein Y is iodo by reacting with an iodizing agent such as sodium iodide.

In the third reaction step, the compound of formula (XI) produced in the second reaction step is reacted with a compound of formula (IIIa) to produce a compound of formula (X). This reaction is carried out under the same condition as in the fourth reaction step of the process 1.

The compound of formula (X) thus produced is subsequently deprotected to produce a compound of formula (Ic). If desired, the resulting compound of formula (Ic) is then alkylated or esterified to produce a compound of formula (Id). This reaction is carried out under the same condition as in the fifth and sixth reaction steps of the process 1.

In addition, the compound of formula (I), wherein n is 0, produced according to the process 2 can be oxidized according to a conventional method to convert into the corresponding sulfinyl or sulfonyl compound wherein n is 1 or 2, as mentioned in the process 1.

The desired compound produced in this process can be separated and purified according to a conventional method such as column chromatography, recrystallization, etc.

Process 3

According to another process 3 of the present invention for preparing the compound of formula (I), the compound of formula (XI) is reacted with an amino compound of formula (XVI) to produce a compound of formula (XV), which is then deprotected and optionally alkylated or esterified according to the same procedures as the fifth and sixth reaction steps of the process 1 to produce a compound of formulae (Ie) and (If). The reaction between the compound of formula (XI) and the compound of formula (XVI) is generally carried out in the presence of a solvent which does not adversely affect the reaction. The solvent which can be preferably used for this purpose includes, for example, chloroform, ethyl acetate, dichloromethane, tetrahydrofuran, etc. The reaction temperature is not specifically limited and the reaction can be generally carried out under cooling to warming.

The desired compound produced in this process can be separated and purified according to a conventional method such as column chromatography, recrystallization, etc.

Process 4

According to the process 4 of the present invention for preparing the compound of formula (Ig), in the first reaction step a compound of formula (VIII) is reacted with a compound of formula (XVI) to produce a compound of formula (XVII). This reaction is carried out in the presence of magnesium so that the compound (XVI) can first be reacted with magnesium to form a Grignard reagent and the resulting Grignard reagent is then reacted with the compound of formula (VIII). The reaction is generally carried out in the presence of a solvent which does not adversely affect the reaction. The solvent which can be preferably used for this purpose includes tetrahydrofuran, ethyl ether, dioxane, etc. The reaction is preferably conducted under anhydrous condition. The reaction is generally carried out under refluxing temperature.

In the second reaction step, the compound of formula (XVII) produced in the first reaction step is reduced to produce a compound of formula (XVIII). This reaction can be practiced by means of any conventional method, for example, sodium cyanoborohydride, lithium aluminumhydride, etc., with Lewis acid such as zinc iodide, iron (III) chloride, trifluoroborane etherate, etc. The reaction is generally carried out in the presence of a solvent which does not adversely affect the reaction. The solvent which can be preferably used for this purpose includes, for example, dichloromethane, 1,2-dichloroethane, chloroform, etc., with dichloromethane being particularly preferable.

In the third reaction step, the compound of formula (XVIII) produced in the second reaction step is deprotected to produce a compound of formula (XIX). The deprotection can be conducted according to a conventional deprotecting method with tetra-n-butylammonium fluoride, hydrogen chloride, hydrogen fluoride, etc. The reaction is generally carried out in the presence of a solvent which does not adversely affect the reaction. The solvent which can be preferably used for this purpose includes, for example, tetrahydrofuran, ethyl ether, dichloromethane, etc., with tetrahydrofuran being particularly preferable.

In the fourth reaction step, the compound of formula (XIX) produced in the third reaction step is reacted with a compound of formula (XX) to produce a compound of formula (XXI). This reaction is generally carried out in the presence of a solvent which does not adversely affect the reaction. The solvent which can be preferably used for this purpose includes, for example, dimethylformamide, toluene, 2-butanone, tetrahydrofuran, acetone, dioxane, etc. The reaction is generally carried out under refluxing in the presence of a base such as potassium carbonate, sodium hydroxide, cesium carbonate, and crown ether.

In the fifth reaction step, the compound of formula (XXI) produced in the fourth reaction step wherein P represents protected hydroxy group, is subsequently deprotected to produce a compound of formula (Ig). The deprotection can be conducted under the same condition as in the fifth reaction step of the process 1.

Process 5

According to the process of the present invention for preparing the compound of formula (XX), in the first reaction step a compound of formula (XXII) is reacted with a compound of formula (XXIII) to produce a compound of formula (XXIV). The reaction is preferably carried out in the presence of a base. The base which can be preferably used for this purpose includes, for example, sodium hydroxide, sodium methoxide, potassium hydroxide, sodium ethoxide, etc., with sodium hydroxide being particularly preferable. The reaction is generally carried out in the presence of a solvent which does not adversely affect the reaction. The solvent which can be preferably used for this purpose includes, for example, methanol, ethanol, tetrahydrofuran, dioxane, etc., with methanol being particularly preferable.

In the second reaction step, the compound of formula (XXIV) produced in the first reaction step is oxidized to produce a compound of formula (XX). As the oxidizing agent suitable for this reaction, for example, sodium periodate ($NaIO_4$), metachloroperbenzoic acid, hydrogen peroxide, oxone, etc. can be preferably used. The reaction is generally carried out in the presence of a solvent which does not adversely affect the reaction. The solvent which can be preferably used for this purpose includes, for example, methanol, dioxane, water, ethanol, tetrahydrofuran, etc.

Process 6

According to the process 6 of the present invention for preparing the compound of formulae (XXVIII) and (XXIX), in the first reaction step a compound of formula (XXV) is reacted with a compound of formula (XII) to produce a compound of formula (XXVI). This reaction is generally carried out in the presence of a solvent which does not adversely affect the reaction. The solvent which can be preferably used for this purpose includes, for example, acetone, 2-butanone, tetrahydrofuran, ethyl acetate, dichloromethane, chloroform, etc., with acetone and 2-butanone being particularly preferable. The reaction temperature is not specifically limited and the reaction can be generally carried out under heating.

In the second reaction step, the compound of formula (XXVI) produced in the first reaction step is reacted with an amino compound of formula (XVI) to produce a compound of formula (XXVII), which is then deprotected and optionally alkylated or esterified according to the same procedures as the fifth and sixth reaction steps of the process 1 to produce a compound of formulae (Ia) and (Ib). The reaction between the compound of formula (XXVI) and the compound of formula (XVI) is generally carried out in the presence of a solvent which does not adversely affect the reaction. The solvent which can be preferably used for this purpose includes, for example, ethanol, isopropanol, t-butanol, tetrahydrofuran, dichloromethane chloroform, etc., with ethanol and isopropanol being particularly preferable. The reaction temperature is not specifically limited and the reaction can be generally carried out under heating.

The desired compound produced in this process can be separated and purified according to a conventional method such as column chromatography, recrystallization, etc.

Process 7

The process 7 depicted in the reaction scheme VII is a method for preparing the chromanon derivative of formula (6) which is the starting compound required for preparing the compound of formula (I) wherein X is S. The specific method and reaction conditions refer to Example 57 described hereinafter.

As stated above, the compound of formula (I) prepared according to the process of the present invention as mentioned above has a good anti-estrogenic activity and, therefore, can be used for treatment of estrogen-related diseases including anovular infertility, breast cancer, endometrial cancer, uterine cancer, ovarian cancer, endometriosis, endometrial fibroma, benign prostate hypertrophy, premature, menstrual disorder, etc.

Therefore, the present invention relates to an anti-estrogenic pharmaceutical composition containing the compound of formula (I) as an active component.

When the anti-estrogenic pharmaceutical composition containing the compound of the present invention as an active component is used for clinical purpose, it can be formulated into a conventional preparation in the pharmaceutical field, for example, preparation for oral administration such as tablet, capsule, troche, solution, suspension, etc., or injectable preparation such as injectable solution or suspension, ready-to-use injectable dry powder which can be reconstituted with distilled water for injection when it is injected, etc., by combining with a carrier conventionally used in the pharmaceutical field.

Suitable carrier which can be used in the composition of the present invention includes those conventionally used in the pharmaceutical field, for example, binder, lubricant, disintegrant, excipient, solubilizer, dispersing agent, stabilizing agent, suspending agent, coloring agent, perfume, etc. for oral preparation; and preservative, pain alleviating agent, solubilizing agent, stabilizing agent, etc. for injectable preparation. The pharmaceutical preparation thus prepared can be administered orally or parenterally, for example, intravenously, subcutaneously or intraperitoneally. In addition, in order to prevent the active component from the decomposition with gastric acid, the oral preparation can be administered together with an antacid or in the enteric-coated form of the solid preparation such as tablet.

The dosage of the benzopyran derivative of formula (I) according to the present invention for human being can be suitably determined depending on absorption, inactivation and secretion of the active ingredient in the human body, age, sex and condition of subject patient, kinds and severity of disease to be treated. It is generally suitable to administer the compound of formula (I) in an amount of 1 to 500 mg, preferably 5 to 200 mg, per day for adult patient.

The present invention is more specifically explained by the following examples. However, it should be understood that the present invention is not limited to these examples in any manner.

EXAMPLE 1

Synthesis of 7-methoxymethyloxy-3-[4-(methoxymethyloxy)phenyl]-3-methyl-2,3-dihydro-4H-benzopyran-4-one 7-Hydroxy-3-(4-hydroxyphenyl)-2,3-dihydro-4H-benzopyran-4-one (1.9 g, 5.5 mmol) and methyl iodide (20.5 ml, 60 equ.) were added to dry tetrahydrofuran (20 ml) under argon atmosphere and the mixture was cooled to −78° C. 2.0M Lithium diisopropylamide (LDA) (4.2 ml) was slowly added dropwise thereto. Then the reaction mixture was slowly warmed to −20° C. with stirring and water was added thereto at the same temperature. The reaction solution was extracted with dichloromethane, dried over magnesium sulfate and then concentrated. The residue was subjected to column chromatography (n-hexane:ethyl acetate=8:1) to obtain 1.3 g (yield: 66%) of the title compound as a colorless oil.

$^1$H-NMR(300 MHz, CDCl$_3$): δ 7.87(d, 1H), 7.33(dd, 2H), 6.97(dd, 2H), 6.65(dd, 1H), 6.53(d, 1H), 5.16(s, 2H), 5.13(s, 2H), 4.81(d, 1H), 4.32(d, 1H), 3.45(s, 3H), 3.45(s, 3H), 1.45(s, 3H).

EXAMPLE 2

Synthesis of (3RS,4RS)-4-[9-(t-butyldimethylsilyloxy)nonynyl]-4-hydoxy-7-methoxymethyloxy-3-[4-(methoxymethyloxy)phenyl]-3-methyl-2,3-dihydro-4H-benzopyran 9-(t-Butyldimethylsilyloxy)-non-1-yne (0.46 g, 1.8 mmol) was dissolved in dry tetrahydrofuran (8 ml) under argon atmosphere and then cooled to −78° C. 2.5M n-Butyllithium (n-BuLi) (0.7 ml, 1.68 mmol) was slowly added dropwise thereto and then the mixture was stirred for 30 minutes. To the mixture was added dropwise 7-methoxymethyloxy-3-[4-(methoxymethyloxy)phenyl]-3-methyl-2,3-dihydro-4H-benzopyran-4-one (200 mg, 6.6 mmol) dissolved in dry tetrahydrofuran (4 ml), and then the reaction mixture was slowly warmed to room temperature. The reaction solution was quenched with water and then extracted with ethyl acetate. The organic layer was separated, dried over magnesium sulfate and concentrated. The residue was subjected to column chromatography (n-hexane:ethyl acetate=4:1) to obtain 350 mg (yield: >100%) of the title compound as a colorless oil.

EXAMPLE 3

Synthesis of (3RS,4RS)-4-(9-hydroxynonyl)-7-methoxymethyloxy-3-[4-(methoxymethyloxy)phenyl]-3-methyl-2,3-dihydro-4H-benzopyran (3RS,4RS)-4-[9-(t-Butyldimethylsilyloxy)nonynyl]-4-hydroxy-7-methoxymethyloxy-3-[4-(methoxymethyloxy)phenyl]-3-methyl-2,3-dihydro-4H-benzopyran (340 mg, 0.56 mmol) was dissolved in ethyl acetate (10 ml) and then 10% Pd/C (180 mg) was added dropwise thereto. The reaction solution was stirred for 15 hours under hydrogen atmosphere, filtered and then concentrated. The residue was subjected to column chromatography (n-hexane:ethyl acetate=4:1→1:1) to obtain 90 mg (yield: 33%) of the title compound as a colorless oil.

$^1$H-NMR(300 MHz, CDCl$_3$): δ 7.05(d, 2H), 6.96(d, 2H), 6.88(d, 1H), 6.49(m, 2H), 5.10(s, 2H), 5.07(s, 2H), 4.45(d, 1H), 4.18(d, 1H), 3.53(t, 2H), 3.42(s, 6H), 2.55(m, 1H), 1.44(m, 2H), 1.23–0.99(brs, 17H).

EXAMPLE 4

Synthesis of (3RS,4RS)-7-methoxymethyloxy-3-[4-(methoxymethyloxy)phenyl]-3-methyl-4-[9-(p-toluenesulfonyloxy)nonyl]-2,3-dihydro-4H-benzopyran (3RS,4RS)-4-(9-Hydroxynonyl)-7-methoxymethyloxy-3-[4-(methoxymethyloxy)phenyl]-3-methyl-2,3-dihydro-4H-benzopyran (90 mg, 0.19 mmol) was dissolved in pyridine (2 ml) and dichloromethane (0.5 ml) and then cooled to 0° C. p-Toluenesulfonylchloride (0.12 g, 0.63 mmol) was added dropwise thereto, and the mixture was stirred for 3 hours at room temperature, quenched with water and then extracted with ethyl acetate. The extracted organic substance was washed with 2N hydrochloric acid, dried over magnesium sulfate and then concentrated. The residue was subjected to column chromatography (n-hexane:ethyl acetate= 4:1) to obtain 105 mg (yield: 88%) of the title compound as a colorless oil.

$^1$H-NMR(300 MHz, CDCl$_3$): δ 7.71(dd, 2H), 7.25(d, 2H), 7.10(d, 2H), 6.95(d, 2H), 6.88(m, 1H), 6.49(m, 2H), 5.10(s, 2H), 5.06(s, 2H), 4.45(d, 1H), 4.18(d, 1H), 3.60(t, 2H), 3.41(s, 6H), 2.56(m, 1H), 2.35(s, 3H), 1.51(m, 2H), 1.17–0.99 (m, 17H).

EXAMPLE 5

Synthesis of (3RS,4RS)-7-methoxymethyloxy-3-[4-(methoxymethyloxy)phenyl]-3-methyl-4-[9-(4,4,5,5,5-pentafluoropentylthio)nonyl]-2,3-dihydro-4H-benzopyran 4,4,5,5,5-Pentafluoropentylthioacetate (0.21 g, 0.9 mmol) was dissolved in methanol (5 ml) and 2N aqueous sodium hydroxide solution (0.8 ml) was added thereto. The reaction solution was stirred for 30 minutes at room temperature and (3RS,4RS)-7-methoxymethyloxy-3-[4-(methoxymethyloxy)phenyl]-3-methyl-4-[9-(p-toluenesulfonyloxy)nonyl]-2,3-dihydro-4H-benzopyran (100 mg, 0.2 mmol) dissolved in methanol (2 ml) was added thereto. The reaction mixture was stirred for one hour at 60° C. and then cooled. After adding water, the reaction solution was extracted with ethyl acetate and the organic layer was dried over magnesium sulfate and concentrated. The residue was subjected to column chromatography (n-hexane:ethyl acetate=7:1) to obtain 100 mg (yield: 97%) of the title compound as a colorless oil.

$^1$H-NMR(300 MHz, CDCl$_3$): δ 7.16(d, 2H), 7.06(d, 2H), 6.98(d, 1H), 6.60(m, 2H), 5.21(s, 2H), 5.18(s, 2H), 4.55(d, 1H), 4.29(d, 1H), 3.52(s, 6H), 2.65(m, 1H), 2.60(t, 2H), 2.51(t, 2H), 2.15(m, 2H), 1.95(m, 2H), 1.57(m, 2H), 1.35–1.10(m, 17H).

EXAMPLE 6

Synthesis of (3RS,4RS)-7-hydroxy-3-(4-hydroxyphenyl)-3-methyl-4-[9-(4,4,5,5,5-pentafluoropentylthio)nonyl]-2,3-dihydro-4H-benzopyran (3RS,4RS)-7-Methoxymethyloxy-3-[4-(methoxymethyloxy)phenyl]-3-methyl-4-[9-(4,4,5,5,5-pentafluoropentylthio)nonyl]-2,3-dihydro-4H-benzopyran (100 mg, 0.15 mmol) and pyridinium p-toluenesulfonate (380 mg, 1.5 mmol) were dissolved in methanol (5 ml) and refluxed for 4 hours. The reaction solution was cooled to room temperature and, after adding water, extracted with ethyl acetate. The extracted organic layer was dried over magnesium sulfate and concentrated. The residue was subjected to column chromatography (n-hexane:ethyl acetate= 4:1) to obtain 57 mg (yield: 66%) of the title compound as a colorless oil.

$^1$H-NMR(300 MHz, CDCl$_3$): δ 7.02(d, 2H), 6.83(d, 1H), 6.75(d, 2H), 6.29(m, 2H), 4.42(d, 1H), 4.14(d, 1H), 2.90(m, 1H), 2.53(t, 2H), 2.44(t, 2H), 2.20(m, 2H), 1.81(m, 2H), 1.48(m, 2H), 1.21–1.02 (m, 17H).

EXAMPLE 7

Synthesis of (3RS,4RS)-7-hydroxy-3-(4-hydroxyphenyl)-3-methyl-4-[9-(4,4,5,5,5-pentafluoropentylsulfinyl)nonyl]-2,3-dihydro-4H-benzopyran (3RS,4RS)-7-Hydroxy-3-(4-hydroxyphenyl)-3-methyl-4-[9-(4,4,5,5,5-pentafluoropentylthio)nonyl]-2,3-dihydro-4H-benzopyran (47 mg, 0.08 mmol) was dissolved in 1,4-dioxane (1 ml), methanol (1 ml) and water (0.25 ml). NaIO$_4$ (20 mg, 0.093 mmol) was added dropwise thereto, and the reaction mixture was stirred for 12 hours at room temperature and then filtered. The filtrate was concentrated and the residue was subjected to column chromatography (n-hexane:ethyl acetate=3:1→1:1) to obtain 35 mg (yield: 73%) of the title compound as a colorless oil.

$^1$H-NMR(300 MHz, CDCl$_3$): δ 7.05(d, 2H), 6.85(d, 1H), 6.80(d, 2H), 6.32(s, 2H), 5.20(s, 1H), 5.16(s, 1H), 4.48(d, 1H), 4.20(dd, 1H), 2.72(m, 2H), 2.56(m, 1H), 2.23(m, 4H), 1.76(m, 2H), 1.30(m, 2H), 1.21–0.90(m, 19H).

MS: 591(M+1)

EXAMPLE 8

Synthesis of (3RS,4RS)-4-[8-(t-butyldimethylsilyloxy)octynyl]-4-hydroxy-7-methoxymethyloxy-3-[4-(methoxymethyloxy)phenyl]-3-methyl-2,3-dihydro-4H-benzopyran 8-(t-Butyldimethylsilyloxy)oct-1-yne (0.6 g, 2.5 mmol) was dissolved in dry tetrahydrofuran (8 ml) under argon atmosphere and then cooled to −78° C. 2.5M n-BuLi (0.94 ml, 2.35 mmol) was slowly added dropwise thereto and then the mixture was stirred for 30 minutes. To the mixture was added dropwise 7-methoxymethyloxy-3-[4-(methoxymethyloxy)phenyl]-3-methyl-2,3-dihydro-4H-benzopyran-4-one (300 mg, 0.84 mmol) dissolved in dry tetrahydrofuran (4 ml), and then the reaction mixture was slowly warmed to room temperature. After 3 hours, water was added to the reaction mixture. The reaction solution was extracted with ethyl acetate and the organic layer was dried over magnesium sulfate. The residue was subjected to column chromatography (n-hexane:ethyl acetate=4:1) to obtain 500 mg (yield: ~100%) of the title compound as a colorless oil.

EXAMPLE 9

Synthesis of (3RS,4RS)-4-(8-hydroxyoctyl)-7-methoxymethyloxy-3-[4-(methoxymethyloxy)phenyl]-3-methyl-2,3-dihydro-4H-benzopyran (3RS,4RS)-4-[8-(t-Butyldimethylsilyloxy)octynyl]-4-hydroxy-7-methoxymethyloxy-3-[4-methoxymethyloxy)phenyl]-3-methyl-2,3-dihydro-4H-benzopyran (500 mg, 0.84 mmol) was dissolved in ethyl acetate (14 mg) and then 10% Pd/C (230 mg) was added thereto. The reaction mixture was stirred under hydrogen atmosphere. After 5 hours, the reaction solution was filtered and then concentrated. The residue was subjected to column chromatography (n-hexane:ethyl acetate=4:1→1:1) to obtain 80ing (yield: 33%) of the title compound as a colorless oil.

EXAMPLE 10

Synthesis of (3RS,4RS)-7-methoxymethyloxy-3-[4-(methoxymethyloxy)phenyl]-3-methyl-4-[8-(p-toluenesulfonyloxy)octyl]-2,3-dihydro-4H-benzopyran (3RS,4RS)-4-(8-Hydroxyoctyl)-7-methoxymethyloxy-3-[4-(methoxymethyloxy)phenyl]-3-methyl-2,3-dihydro-4H-benzopyran (80 mg, 0.17 mmol) was dissolved in pyridine (2 ml) and dichloromethane (0.5 ml) and then cooled to 0° C. p-Toluenesulfonylchloride (0.12 g, 0.63 mmol) was added thereto and the mixture was stirred for 6 hours at room temperature. Water was added thereto at 0° C. and the reaction solution was extracted with ethyl acetate, washed with saturated saline and then dried over magnesium sulfate. The residue was subjected to column chromatography (n-hexane:ethyl acetate=4:1) to obtain 110 mg (yield: ~100%) of the title compound as a colorless oil.

EXAMPLE 11

Synthesis of (3RS,4RS)-7-methoxymethyloxy-3-[4-(methoxymethyloxy)phenyl]-3-methyl-4-[8-(4,4,5,5,5-pentafluoropentylthio)octyl]-2,3-dihydro-4H-benzopyran 4,4,5,5,5-Pentafluoropentylthioacetate (0.28 g, 1.2 mmol) was dissolved in methanol (5 ml) and 2N aqueous sodium hydroxide solution (1 ml) was added thereto. The reaction solution was stirred for 40 minutes at room temperature and (3RS,4RS)-7-methoxymethyloxy-3-[4-(methoxymethyloxy)phenyl]-3-methyl-4-[8-(p-toluenesulfonyloxy)octyl]-2,3-dihydro-4H-benzopyran (100 mg, 0.2 mmol) dissolved in methanol (2 ml) was added thereto. The reaction mixture was stirred for 2 hours at 60° C. and then cooled. After adding water, the reaction solution was extracted with ethyl acetate and the organic layer was dried over magnesium sulfate and concentrated. The residue was subjected to column chromatography (n-hexane:ethyl=acetate 8:1) to obtain 120 mg (yield: ~100%) of the title compound as a colorless oil.

$^1$H-NMR(300 MHz, CDCl$_3$): δ 7.16(d, 2H), 7.10(d, 2H), 6.97(d, 1H), 6.60(m, 2H), 5.21(s, 2H), 5.18(s, 2H), 4.55(d, 1H), 4.30(d, 1H), 3.52(s, 6H), 2.65(m, 1H), 2.60(t, 2H), 2.52(t, 2H), 2.20(m, 2H), 1.91(m, 2H), 1.53(m, 2H), 1.32–1.10 (m, 15H).

EXAMPLE 12

Synthesis of (3RS,4RS)-7-hydroxy-3-(4-hydroxyphenyl)-3-methyl-4-[8-(4,4,5,5,5-pentafluoropentylthio)octyl]-2,3-dihydro-4H-benzopyran (3RS,4RS)-7-Methoxymethyloxy-3-[4-(methoxymethyloxy)phenyl]-3-methyl-4-[8-(4,4,5,5,5-pentafluoropentylthio)octyl]-2,3-dihydro-4H-benzopyran (120 mg, 0.19 mmol) and pyridinium p-toluenesulfonate (580 mg, 2.3 mmol) were dissolved in methanol (8 ml) and then refluxed for 7 hours. The reaction solution was cooled to room temperature and, after adding water, extracted with ethyl acetate. The organic layer was separated, washed with water, dried over magnesium sulfate and then concentrated. The residue was subjected to column chromatography (n-hexane:ethyl acetate=4:1) to obtain 64 mg (yield: 69%) of the title compound as a colorless oil.

$^1$H-NMR(300 MHz, CDCl$_3$): δ 7.01(dd, 2H), 6.83(d, 1H), 6.77(d, 2H), 6.30(d, 2H), 4.96(s, 1H), 4.76(s, 1H), 4.44(d, 2H), 4.18(d, 2H), 2.51(m, 3H), 2.40(t, 2H), 2.05(m, 2H), 1.81(m, 2H), 1.44(m, 2H), 1.21–0.98(m, 15H).

MS: 561(M+1)

EXAMPLE 13

Synthesis of (3RS,4RS)-7-hydroxy-3-(4-hydroxyphenyl)-3-methyl-4-[8-(4,4,5,5,5-pentafluoropentylsulfinyl)octyl]-2,3-dihydro-4H-benzopyran (3RS,4RS)-7-Hydroxy-3-(4-hydroxyphenyl)-3-methyl-4-[8-(4,4,5,5,5-pentafluoropentylthio)octyl]-2,3-dihydro-4H- benzopyran (53 mg, 0.095 mmol) was dissolved in 1,4-dioxane (1.2 ml), methanol (1.2 ml) and water (0.3 ml). NaIO$_4$ (24 mg, 0.11 mmol) was added dropwise thereto, and the reaction mixture was stirred for 8 hours at room temperature and then filtered. The filtrate was concentrated and the residue was subjected to column chromatography (n-hexane:ethyl acetate=2:1) to obtain 38 mg (yield: 70%) of the title compound as a colorless oil.

$^1$H-NMR(300 MHz, CDCl$_3$): δ 6.98(dd, 2H), 6.83(m, 3H), 6.33(d, 2H), 4.16(d, 1H), 2.72(m, 3H), 2.48(m, 2H), 2.16–2.11(m, 4H), 1.62(m, 2H), 1.24–0.93(m, 15H).

MS: 577(M+1)

EXAMPLE 14

Synthesis of (3RS,4RS)-7-hydroxy-3-(4-hydroxyphenyl)-3-methyl-4-[9-(4,4,5,5,5-pentafluoropentylsulfonyl)nonyl]-2,3-dihydro-4H-benzopyran (3RS,4RS)-7-Hydroxy-3-(4-hydroxyphenyl)-3-methyl-4-[9-(4,4,5,5,5-pentafluoropentylthio)nonyl]-2,3-dihydro-4H-benzopyran (65 mg, 0.113 mmol) was dissolved in methanol (3 mg) and water (1.5 ml). Oxone (210 mg, 0.34 mmol) was added dropwise thereto, and the reaction mixture was stirred for 14 hours at room temperature. After adding water, the reaction solution was extracted with ethyl acetate, dried over magnesium sulfate and then concentrated. The residue was subjected to column chromatography (n-hexane:ethyl acetate=4:1→2:1) to obtain 28 mg (yield: 41%) of the title compound as a colorless oil.

$^1$H-NMR(300 MHz, CDCl$_3$): δ 7.01(d, 2H), 6.83(d, 1H), 6.77(d, 2H), 6.32(s, 2H), 5.45(s, 1H), 4.95(s, 1H), 4.43(d, 1H), 4.17(d, 1H), 2.99(t, 2H), 2.90(t, 2H), 2.50(m, 1H), 2.19–2.12(m, 4H), 1.30(m, 2H), 1.28–0.99(m, 17H).

MS: 607(M+1)

EXAMPLE 15

Synthesis of 4-(4-hydroxyphenyl)-4-hydroxy-7-methoxymethyloxy-3-[4-(methoxymethyloxy)phenyl]-2,3-dihydro-4H-benzopyran Under nitrogen atmosphere, 3-bromomagnesium phenyl trimethylsilyl ether prepared from 3-bromophenyl trimethylsilyl ether (2.35 g, 9.57 mmol) and magnesium turning (0.23 g, 9.57 mmol) in dry tetrahydrofuran (3 ml) was cooled to −78° C. 7-Methoxymethyloxy-3-[4-(methoxymethyloxy)phenyl]-2,3-dihydro-4H-benzopyran-4-one (1 g, 2.9 mmol) dissolved in dry tetrahydrofuran (2 ml) was slowly added dropwise thereto, and the mixture was stirred for one hour. The reaction solution was quenched with saturated aqueous ammonium chloride solution and then extracted with ethyl acetate. The organic layer was dried over anhydrous magnesium sulfate and concentrated under reduced pressure to remove the organic solvent. The concentrate was then subjected to column chromatography (n-hexane:ethyl acteate=4:1) to obtain 903 mg (yield: 74%) of the title compound as a foam.

$^1$H-NMR(300 MHz, CDCl$_3$): δ 7.05(dd, 1H), 6.98(d, 2H), 6.81(d, 2H), 6.73(s, 1H), 6.67(t, 2H), 6.55(d, 3H), 5.21(s, 2H), 5.12(s, 2H), 4.71(dd, 1H), 4.21(d, 1H), 3.50(dd, 1H), 3.42(s, 6H).

EXAMPLE 16

Synthesis of 4-[4-(5chloropentyloxy)phenyl]-4-hydroxy-7-methoxymethyloxy-3-[4-(methoxymethyloxy)phenyl]-2,3-dihydro-4H-benzopyran 4-(4-Hydroxyphenyl)-4-hydroxy-7-methoxymethyloxy-3-[4-(methoxymethyloxy)phenyl]-2,3-dihydro-4H-benzopyran (180 mg, 0.4 mmol), 1-bromo-5-chloropentane (0.39 ml, 2 mmol) and 2N aqueous sodium hydroxide solution (70 μl, 2 mmol) were dissolved in acetone (4 ml) and then refluxed for 6 hours. The reaction mixture was cooled to room temperature and, after adding water, extracted with ethyl acetate. The organic layer was dried over anhydrous magnesium sulfate, filtered and then concentrated under reduced pressure to remove the organic solvent. The concentrate was subjected to column chromatography (n-hexane:ethyl acetate=4:1) to obtain 247 mg (yield: 97%) of the title compound as a colorless oil.

$^1$H-NMR(300 MHz, CDCl$_3$): δ 7.10(m, 1H), 6.78(m, 5H), 6.70(dd, 3H), 6.63(s, 1H), 6.45(dd, 1H), 5.23(s, 2H), 5.14(s, 2H), 4.65(t, 1H), 4.22(dd, 1H), 3.83(m, 2H), 3.72(t, 2H), 3.43(s, 6H), 1.82(m, 2H), 1.48(m, 2H), 1.17(t, 2H).

EXAMPLE 17

Synthesis of 4-hydroxy-4-[4-(5-iodopentyloxy)phenyl]-7-methoxymethyloxy-3-[4-(methoxymethyloxy)phenyl]-2,3-dihydro-4H-benzopyran 4-[4-(5-Chloropentyloxy)phenyl]-4-hydroxy-7-methoxymethyloxy-3-[4-(methoxymethyloxy)phenyl]-2,3-dihydro-4H-benzopyran (167 mg, 0.3 mmol) and sodium iodide (139 mg, 0.9 mmol) were dissolved in methyl ethyl ketone (5 ml) and then refluxed for 12 hours. The reaction solution was cooled to room temperature and, after adding water, extracted with ethyl acetate. The organic layer was dried over anhydrous magnesium sulfate, filtered and then concentrated under reduced pressure to remove the organic solvent. The concentrate was subjected to column chromatography (n-hexane:ethyl acetate=4:1) to obtain 142 mg (yield: 75%) of the title compound as a colorless oil.

$^1$H-NMR(300 MHz, CDCl$_3$): δ 7.05(m, 1H), 6.72(m, 5H), 6.65(dd, 3H), 6.55(s, 1H), 6.41(dd, 1H), 5.16(s, 2H), 5.13(s, 2H), 4.61(t, 1H), 4.21(dd, 1H), 3.81(m, 2H), 3.41(s, 6H), 3.13(t, 2H), 1.72(m, 2H), 1.56–1.45(m, 2H), 1.16(t, 2H).

EXAMPLE 18

Synthesis of 4-hydroxy-7-methoxymethyloxy-3-[4-(methoxymethyloxy)phenyl]-4-[4-(5-(4,4,5,5,5-pentafluoropentylthio)pentyloxy)phenyl]-2,3-dihydro-4H-benzopyran 4,4,5,5,5-Pentafluoropentylthioacetate (254 mg, 1.1 mmol) was dissolved in methanol (3 ml) and 2N aqueous sodium hydroxide solution (0.43 ml) was added thereto. The reaction solution was stirred for one hour at room temperature and 4-hydroxy-4-[4-(5-iodopentyloxy)phenyl]-7-methoxymethyloxy-3-[4-(methoxymethyloxy)phenyl]-2,3-dihydro-4H-benzopyran (142mg, 0.22 mmol) dissolved in methanol (2 ml) was added dropwise thereto. The reaction mixture was stirred for 2 hours at 60° C. and then cooled to room temperature. After adding water, the reaction solution was extracted with ethyl acetate and the organic layer was dried over anhydrous magnesium sulfate, filtered and then concentrated under reduced pressure to remove the organic solvent. The concentrate was subjected to column chromatography (n-hexane:ethyl acetate=4:1) to obtain 153 mg (yield: 98%) of the title compound as a colorless oil.

$^1$H-NMR(CDCl$_3$, CDCl$_3$): δ 7.20(t, 1H), 6.92(m, 5H), 6.78(dd, 3H), 6.63(d, 1H), 6.56(dd, 1H), 5.25(s, 2H), 5.20(s, 2H), 4.72(t, 1H), 4.20(dd, 1H), 3.80(m, 2H), 3.42(s, 6H), 2.61(m, 4H), 2.10(m, 2H), 1.72(m, 2H), 1.55(m, 4H), 1.25(s, 2H).

EXAMPLE 19

Synthesis of 7-hydroxy-3-(4-hydroxyphenyl)-4-[4-(5-(4,4,5,5,5-pentafluoropentylthio)pentyloxy)phenyl]-2H-benzopyran 4-Hydroxy-7-methoxymethyloxy-3-[4-(methoxymethyloxy)phenyl]4-[4-(5-(4,4,5,5,5-pentafluoropentylthio)pentyloxy)phenyl]-2,3-dihydro-4H-benzopyran (220 mg, 0.3 mmol) and pyridinium p-toluenesulfonate (789 mg, 3 mmol) were dissolved in methanol (8 mg) and then refluxed for 8 hours. The reaction solution was cooled to room temperature and, after adding water, extracted with ethyl acetate. The organic layer was dried over anhydrous magnesium sulfate, filtered and then concentrated under reduced pressure to remove the organic solvent. The concentrate was subjected to column chromatography (n-hexane:ethyl acetate=1:1) to obtain 142 mg (yield, 78%) of the title compound as a colorless oil.

$^1$H-NMR(300 MHz, CDCl$_3$): δ 7.12(q, 1H), 6.80(dd, 2H), 6.72(d, 1H), 6.65(dd, 2H), 6.52(dd, 3H), 6.35(d, 1H), 6.20 (dd, 1H), 5.06(s, 2H), 3.76(t, 2H), 2.63(m, 4H), 2.22–2.01 (m, 2H), 1.83(m, 2H), 1.75–1.62(m, 2H), 1.45–1.37(m, 2H), 1.20(m, 2H), 0.91–0.80(t, 2H).

EXAMPLE 20

Synthesis of 4-methoxyphenylglyoxylic ethyl ester

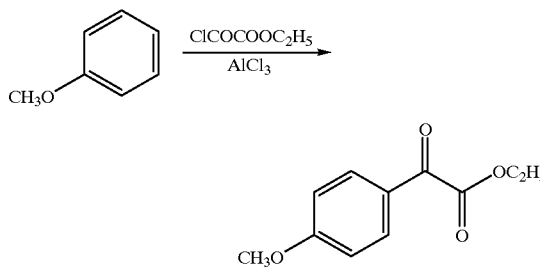

Aluminum chloride (84.30 g, 632 mmol) was added to chloroform (300 ml) and chloroglyoxylic ethyl ester (60 g, 439 mmol) was added dropwise to the resulting suspension over 20 minutes at 0° C. The reaction mixture was stirred for 40 minutes at 5° C. At the same temperature, anisole (68.79 g, 636 mmol) was slowly added dropwise to the reaction solution and then stirred for 12 hours at 10° C. When the reaction is completed, the reaction solution was cooled and, after adding cooling water (100 ml), extracted with dichloromethane. The extract was dried over anhydrous magnesium sulfate and then concentrated to obtain the title compound as a yellow solid (TLC identification). The resulting compound was used in the next reaction without further purification.

EXAMPLE 21

Synthesis of 4-methoxyphenylglyoxylic acid

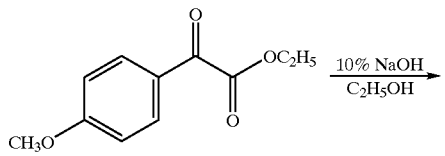

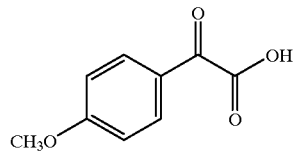

4-Methoxyphenylglyoxylic ethyl ester obtained in Example 20 was dissolved in 20% sodium hydroxide (60 mg) and methanol (600 ml) and then stirred for 3 hours with heating at 80° C. When the reaction is completed, the reaction solution was extracted with diethyl ether (200 mg) and the obtained aqueous solution was acidified (pH 1–2) with hydrochloric acid. The resulting aqueous acidic solution was extracted with dichloromethane, and the extract was dried over anhydrous magnesium sulfate and then concentrated under reduced pressure to remove the organic solvent to obtain 34.63 g (yield in two reaction steps: 43%) of the title compound as a pale violet solid.

$^1$H-NMR(270 MHz, CDCl$_3$): δ 8.59(brs, 1H, COOH), 8.44(d, $^3$J=8.9 Hz, 2H, Ar—H), 6.99(d, $^3$J=8.9 Hz, 2H, Ar—H), 3.92(s, 3H, OCH$_3$).

EXAMPLE 22

Synthesis of 2-hydroxy-2-(4-methoxyphenyl)propionic acid

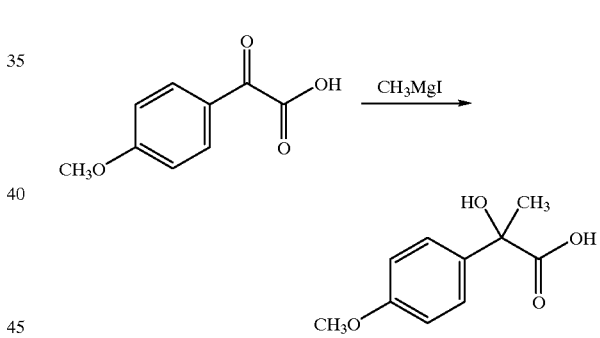

Methyl iodide (55 ml, 880 mmol) was slowly added to a solution of magnesium (23 g) in diethyl ether (500 ml) at −20° C. and then stirred for 3 hours at room temperature. To the resulting suspension was slowly added dropwise 4-methoxyphenylglyoxylic acid (34.6 g, 192 mmol), as prepared in Example 21, dissolved in dry tetrahydrofuran (100 ml) at 0° C., and the reaction mixture was stirred for about 12 hours at room temperature. After adding cooling water, the reaction solution was extracted with ethyl acetate and the organic layer was washed with water and saturated sodium thiosulfate solution and dried over anhydrous magnesium sulfate. The residue was concentrated under reduced pressure to remove the organic solvent to obtain 35 g (yield: 93%) of the title compound as a yellow solid.

$^1$H-NMR(270 MHz, CDCl$_3$): δ 7.39(d, $^3$J=8.9 Hz, 2H, Ar—H), 7.16(s, 1H, COOH), 6.89(d, $^3$J=8.5 Hz, 2H, Ar—H), 4.90(brs, 1H, OH), 3.80(s, 3H, OCH$_3$), 1.71(s, 3H, CH$_3$).

EXAMPLE 23

Synthesis of 2-(4-methoxyphenyl)acrylic acid

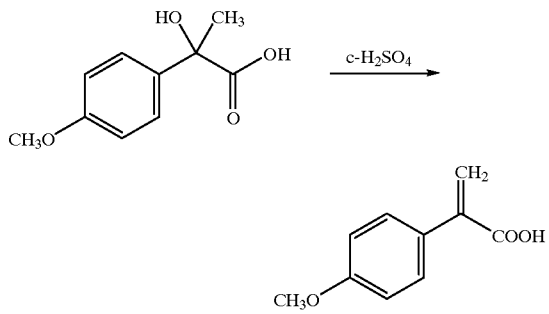

2-Hydroxy-2-(4-methoxyphenyl)propionic acid (35 g, 178 mmol) was dissolved in dioxane (700 ml) and concentrated sulfuric acid (60 ml) was added thereto. The reaction mixture was refluxed for 2 hours under heating. The reaction solution was cooled and, after adding water, extracted with ethyl acetate. The organic layer was washed with saturated sodium thiosulfate solution and water, dried over anhydrous magnesium sulfate and then concentrated under reduced pressure to obtain 24.8 g (yield: 72%) of the title compound as a brown solid.

$^1$H-NMR(270 MHz, CDCl$_3$): δ 7.39(d, $^3$J=8.5 Hz, 2H, Ar—H), 7.40(s, 1H, COOH), 6.89(d, $^3$J=8.5 Hz, 2H, Ar—H), 6.45(s, 1H, =CH$_2$), 5.96(s, 1H, =CH$_2$), 3.82(s, 3H, OCH$_3$).

EXAMPLE 24

Synthesis of 2-(4-methoxyphenyl)-3-(3-methoxyphenylthio)propionic acid

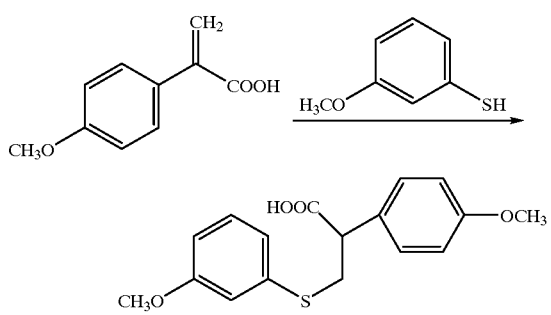

3-Methoxybenzenethiol(2.5 ml, 20.1 mmol) was added to 2-(4-methoxyphenyl)acrylic acid (3 g, 16.8 mmol) and stirred for 21 hours with heating at 125° C. The reaction solution was extracted with diethyl ether, and the ether solution was washed with 0.1N iodine-potassium iodide solution, water and saturated sodium chloride solution and dried over anhydrous magnesium sulfate. The residue was concentrated under reduced pressure to remove the organic solvent to obtain the title compound as a brown oil. The resulting compound was used in the next reaction without further purification.

EXAMPLE 25

Synthesis of 7-methoxy-3-(4-methoxyphenyl)thiochroman-4-one

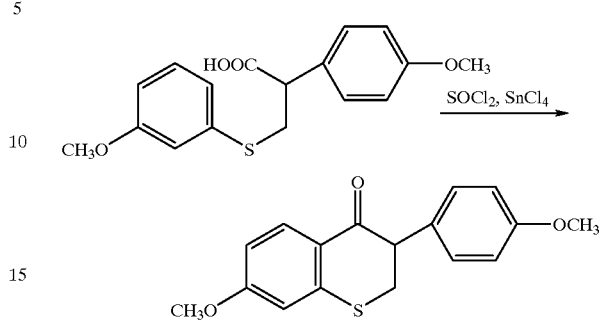

2-(4-Methoxyphenyl)-3-(3-methoxyphenylthio)propionic acid obtained in Example 24 was dissolved in benzene (20 ml) and thionyl chloride (4.1 ml, 55.9 mmol) was added thereto. The reaction mixture was heated for 2 hours at 80° C. When the reaction is completed, the reaction solution was concentrated under reduced pressure to remove benzene and cooled to 5° C. Benzene (10 ml) was added to the reaction solution and then tin(IV) chloride (4.1 ml, 34.9 mmol) was slowly added dropwise thereto. The reaction mixture was stirred for 12 hours and then water (30 ml), concentrated hydrochloric acid (10 ml) and chloroform (30 ml) were added thereto. The reaction solution was heated under refluxing for one hour and extracted with chloroform. The organic layer was washed with water and sodium hydrogen carbonate solution, dried over anhydrous magnesium sulfate and concentrated under reduced pressure. The residue was purified with column chromatography (n-hexane:ethyl acetate=8:2) to obtain 1 g (yield in two reaction steps: 20%) of the title compound as a yellow solid.

$^1$H-NMR(270 MHz, CDCl$_3$): δ 8.13(d, $^3$J=9.5 Hz, H, C5-H), 7.12(d, $^3$J=8.9 Hz, 2H, Ar—H), 6.88(d, $^3$J=8.6Hz, 2H, Ar—H), 6.73(m, 2H, Ar—H), 4.01(dd, $^3$J=10.5 and 3.9 Hz, 1H, C3-H), 3.85(s, 3H, OCH$_3$), 3.79(s, 3H, OCH$_3$), 3.53(dd, $^3$J=10.5 and 13.2 Hz, 1H, C2-H), 3.31(dd, $^3$J=13.2 and 3.9 Hz, 1H, C2-H).

EXAMPLE 26

Synthesis of 7-methoxy-3-(4-methoxyphenyl)-3-methylthiochroman-4-one

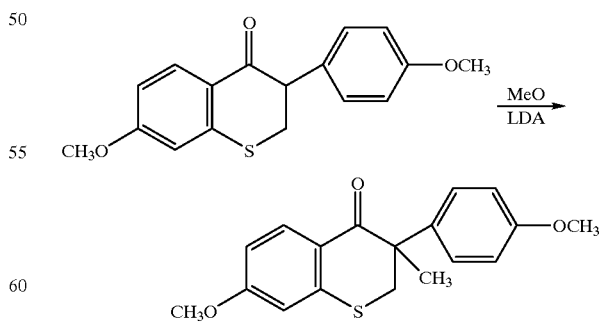

To 7-methoxy-3-(4-methoxyphenyl)thiochroman-4-one (725 mg, 2.41 mmol) obtained in Example 25 was added dry tetrahydrofuran (30 ml). Then lithium diisopropylamide (2.41 ml, 4.83 mmol, 2.0 mol hexane/tetrahydrofuran solution) was added dropwise thereto at −78° C. The reaction mixture was stirred for 45 minutes and methyl iodide (7.5 ml, 120.6 mmol) was added thereto. The reaction solution was stirred for one hour at −78° C. and for 24 hours at −10° C. and, after adding water, extracted with ethyl acetate. The organic layer was washed with water and saturated sodium chloride solution, dried over anhydrous magnesium sulfate and then concentrated under reduced pressure. The residue was purified with column chromatography (n-hexane:ethyl acetate=9:1) to obtain 550 mg (yield: 72%) of the title compound as a yellow solid.

$^1$H-NMR(270 MHz, CDCl$_3$): δ 8.17(d, $^3$J=8.9 Hz, 1H, C5-H), 7.14(dd, $^3$J=8.9 Hz, $^4$J=2.0 Hz, 2H, Ar—H), 6.82(dd, $^3$J=8.9 Hz, 2.0 Hz, 2H, Ar—H), 6.70(dd, $^3$J=8.9 Hz, $^4$J=2.3 Hz, 1H, C6-H), 6.57(d, $^4$J=2.7 Hz, 1H, C8-H), 3.78(s, 3H, OCH$_3$), 3.75(s, 3H, OCH$_3$), 3.44(d, $^2$J=4.9 Hz, 2H, 2×C2-H), 1.58(s, 3H, C3-CH$_3$).

EXAMPLE 27

Synthesis of 4-[9-(t-butyldimethylsilyloxy)-1-nonynyl]-4-hydroxy-7-methoxy-3-(4-methoxyphenyl)-3-methylthiochroman

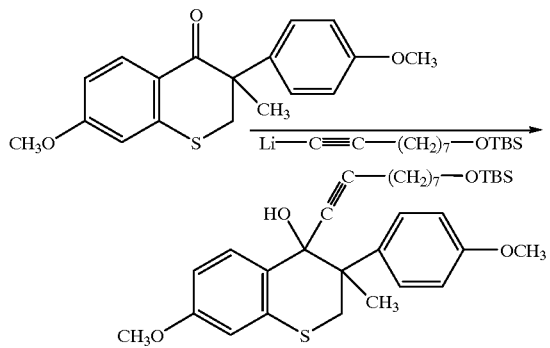

To 9-(t-butyldimethylsilyloxy)-1-nonyne (2.23 g, 8.75 mmol) was added dry tetrahydrofuran (30 ml). Then n-butyl lithium (4.65 ml, 7.87 mol, 1.69 mol/l tetrahydrofuran solution) was added dropwise thereto at −78° C. and the resulting mixture was stirred for one hour at −20° C. At the same temperature, to the reaction solution was added 7-methoxy-3-(4-methoxyphenyl)-3-methylthiochroman-4-one (550 mg, 1.75 mmol), as obtained in Example 26, dissolved in tetrahydrofuran (20 ml), and then the mixture was stirred for 24 hours at −10° C. When the reaction is completed, saturated ammonium chloride solution was added to the reaction solution which was then extracted with ethyl acetate. The extract was dried over anhydrous magnesium sulfate and concentrated under reduced pressure. The residue was purified with column chromatography (n-hexane:ethyl acetate=9:1) to obtain 946 mg (yield: 95%) of the title compound as a white solid.

$^1$H-NMR(270 MHz, CDCl$_3$): δ 7.86(d, $^3$J=8.5 Hz, 1H, Ar—H), 7.59(d, $^3$J=8.9 Hz, 2H, Ar—H), 6.87(d, $^3$J=8.9 Hz, 2H, Ar—H), 6.63(m, 2H, Ar—H), 4.25(d, $^2$J=12.6 Hz, 1H, C2-H), 3.81(s, 3H, OCH$_3$), 3.77(s, 3H, OCH$_3$), 3.59(t $^3$J=6.6 Hz, 2H, CH$_2$-OTBS), 2.70(d, $^2$J=12.6 Hz, 1H, C2-H), 2.18(t, $^2$J=6.6 Hz, 3H, CH$_2$—C≡C and OH), 1.48(s, 3H, C3-CH$_3$), 1.36(m, 10H, alkyl-H), 0.89(s, 9H, t-butyl-H), 0.04(s, 6H, 2×CH$_3$).

EXAMPLE 28

Synthesis of 4-[9-(t-butyldimethylsilyloxy)-1-nonynyl]-7-methoxy-3-(4-methoxyphenyl)-3-methylthiochroman

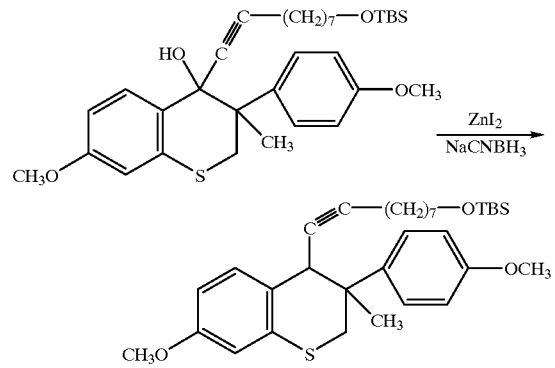

Dichloromethane (30 ml) was added to 4-[9-(t-butyldimethylsilyloxy)-1-nonynyl]-4-hydroxy-7-methoxy-3-(4-methoxyphenyl)-3-methylthiochroman (946 mg, 1.66 mmol) obtained in Example 27, and then zinc iodide (795 mg, 2.49 mmol) and sodium cyanoborohydride (782 mg, 12.45 mmol) were added thereto. The reaction solution was stirred for 24 hours at room temperature and, after adding water, extracted with ethyl acetate. The extract was dried over anhydrous magnesium sulfate and concentrated under reduced pressure. The residue was purified with column chromatography (n-hexane:ethyl acetate=9:1) to obtain 569 mg (yield: 62%, 3RS,4RS/3RS,4SR=5:1) of the title compound as a white solid.

$^1$H-NMR(270 MHz, CDCl$_3$, 3RS,4RS-compound): δ 7.25 (m, 3H, Ar—H), 6.82(d, $^3$J=8.9 Hz, 2H, Ar—H), 6.68(m, 2H, Ar—H), 3.78(s, 3H, OCH$_3$), 3.76(s, 3H, OCH$_3$), 3.72(s, 1H, C4-H), 3.76(d, $^2$J=12.2 Hz, 1H, C2-H), 3.58(t, $^3$J=6.6 Hz, 2H, CH$_2$—OTBS), 2.99(d, $^2$J=12.2 Hz, 1H, C2-H), 2.02(m, 2H, CH$_2$—C≡C), 1.44(s, 3H, C3-CH$_3$), 1.20(m, 10H, alkyl-H), 0.89(s, 9H, t-butyl-H), 0.05(s, 6H, 2×CH$_3$).

EXAMPLE 29

Synthesis of 4-[9-(t-butyldimethylsilyloxy)nonyl]-7-methoxy-3-(4-methoxyphenyl)-3-methylthiochroman

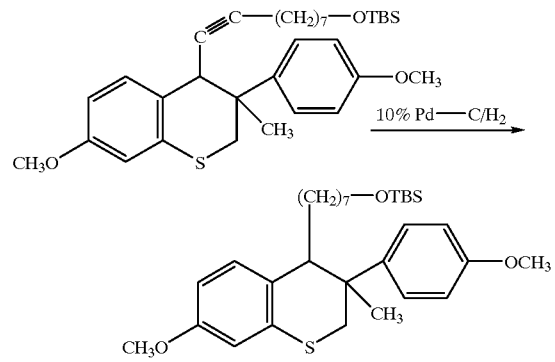

Methanol (60 ml) and 10% Pd/C (500 mg) were added to 4-[9-(t-butyl-dimethylsilyloxy)-1-nonynyl]-7-methoxy-3-(4-methoxyphenyl)-3-methylthiochroman (560 mg, 1.01 mmol) obtained in Example 28, and the mixture was stirred for 2 days under hydrogen gas (normal pressure). Ethyl acetate was added to the reaction solution which was then filtered, washed several times with ethyl acetate and concentrated under reduced pressure to remove the organic solvent. To the residue were added methanol (60 ml) and 10% Pd/C (300 mg), and the reaction mixture was stirred for 8 hours at 5 atomsphere under hydrogen gas. Ethyl acetate was added again to the reaction solution which was then filtered and concentrated under reduced pressure to obtain 450 mg (yield: 80%) of the title compound as an oil. The resulting compound was used in the next reaction without further purification.

$^1$H-NMR(270 MHz, CDCl$_3$, 3RS,4RS-compound): δ 7.28 (d, $^3$J=8.9 Hz, 2H, Ar—H), 6.91(m, 3H, Ar—H), 6.72(d, $^4$J=2.3 Hz, 1H, C8-H), 6.58(dd, $^3$J=8.6 Hz, $^4$J=2.6 Hz, 1H, Ar—H), 3.82(s, 3H, OCH$_3$), 3.78(s, 3H, OCH$_3$), 3.64(d, $^2$J=11.5 Hz, 1H, C2-H), 3.56(t, $^3$J=6.6 Hz, 2H, CH$_2$—OTBS), 2.98(d, $^2$J=11.5 Hz, 1H, C2-H), 2.71(brt, 1H, C4-H), 1.48–1.17(m, 19H, C3-CH$_3$ and alkyl-H), 0.88(s, 9H, t-butyl-H), 0.03(s, 6H, 2×CH$_3$).

EXAMPLE 30

Synthesis of 4-(9-hydroxynonyl)-7-methoxy-3-(4-methoxyphenyl)-3-methylthiochroman

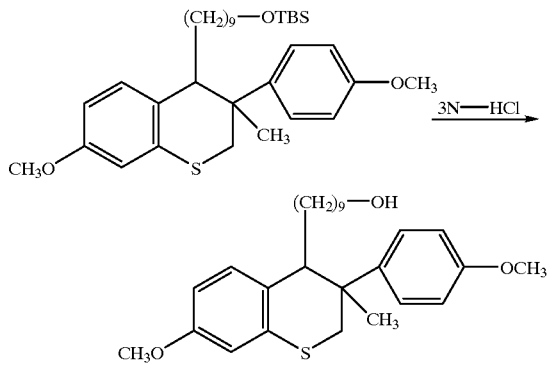

4-[9-(t-Butyldimethylsilyloxy)nonyl]-7-methoxy-3-(4-methoxyphenyl)-3-methylthiochroman (400 mg, 0.72 mmol) obtained in Example 29 was dissolved in tetrahydrofuran (40 ml), and 3N—HCl (2 ml) was added thereto. The reaction mixture was stirred for 3 hours at room temperature. When the reaction is completed, water was added to the reaction solution which was then extracted with ethyl acetate. The extract was dried over anhydrous magnesium sulfate and concentrated under reduced pressure. The residue was purified with column chromatography (n-hexane:ethyl acetate=7:3) to obtain 235 mg (yield: 74%, 3RS,4RS/3RS,4SR=9:1) of the title compound as a white solid.

$^1$H-NMR(270 MHz, CDCl$_3$, 3RS,4RS-compound): δ 7.29 (d, $^3$J=8.9 Hz, 2H, Ar—H), 6.91(m, 3H, Ar—H), 6.71(m, 1H, Ar—H), 6.58(m, 1H, Ar—H), 3.82(s, 3H, OCH$_3$), 3.78(s, 3H, OCH$_3$), 3.68(m, 4H, CH$_2$—OH, C2-H), 2.98(d, $^2$J=11.6 Hz, 1H, C2-H), 2.78(brt, 1H, C4-H), 1.56–1.08(m, 19H, C3-CH$_3$ and alkyl-H).

EXAMPLE 31

Synthesis of 4-(9-methanesulfonyloxynonyl)-7-methoxy-3-(4-methoxyphenyl)-3-methylthiochroman

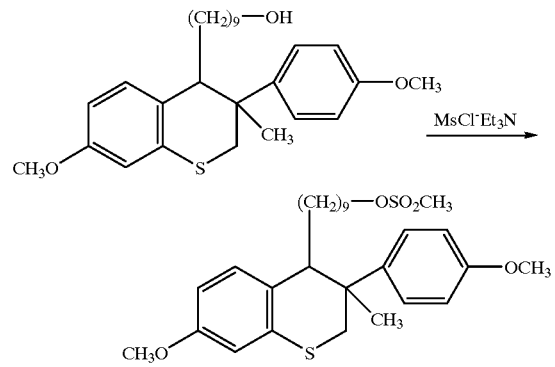

4-(9-Hydroxynonyl)-7-methoxy-3-(4-methoxyphenyl)-3-methylthiochroman (131 mg, 0.30 mmol) obtained in Example 30 was dissolved in dichloromethane (12 ml) and then triethylamine (0.2 ml, 1.48 mmol) and methanesulfonyl chloride (0.11 ml, 1.48 mmol) were added thereto. The reaction mixture was stirred for 40 minutes at room temperature. When the reaction is completed, water was added to the reaction solution which was then extracted with ethyl acetate. The organic layer was washed with water and saturated sodium chloride solution and dried over anhydrous magnesium sulfate. The residue was purified with column chromatography (n-hexane:ethyl acetate=7:3) to obtain 141 mg (yield: 91%, 3RS,4RS/3RS,4SR=8.5/1) of the title compound as an oil.

$^1$H-NMR(270 MHz, CDCl$_3$, 3RS,4RS-compound): δ 7.29 (d, $^3$J=8.9 Hz, 2H, Ar—H), 6.91(m, 3H, Ar—H), 6.70(d, $^4$J=2.3 Hz, 1H, C8-H), 6.58(dd, $^3$J=8.5 Hz, $^4$J=2.3 Hz, 1H, Ar—H), 4.18(t, $^3$J=6.6 Hz, 2H, OCH$_2$), 3.82(s, 3H, OCH$_3$), 3.78(s, 3H, OCH$_3$), 3.64(d, $^2$J=11.3 Hz, 1H, C2-H), 2.99(s, 3H, OSO$_2$CH$_3$), 2.97(brd, $^2$J=not resolved, 1H, C2-H), 2.78 (brt, 1H, C4+1), 1.63(m, 3H, alkyl-H), 1.37–1.08(m, 16H, C3-CH$_3$ and alkyl-H).

EXAMPLE 32

Synthesis of 7-methoxy-3-(4-methoxyphenyl)-3-methyl-4-[9-(4,4,5,5,5-pentafluoropentylthio)nonyl]-thiochroman

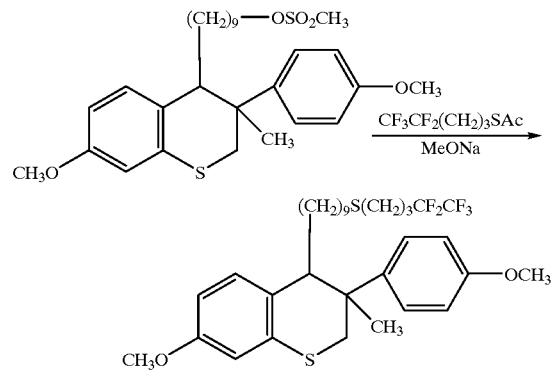

4,4,5,5,5-Pentafluoropentylthioacetate (424 mg, 1.89 mmol) was dissolved in absolute methanol (10 ml) and 1M sodium methoxide (1.62 ml) was added thereto. The reaction solution was stirred for one hour at room temperature and 4-(9-methanesulfonyloxynonyl)-7-methoxy-3-(4-methoxyphenyl)-3-methylthiochroman (141 mg, 0.27 mmol), as obtained in Example 31, dissolved in dry tetrahydrofuran (10 ml) was added dropwise thereto at room temperature. The reaction mixture was stirred for 24 hours. When the reaction is completed, water was added to the reaction solution which was then extracted with ethyl acetate. The organic layer was washed with water and saturated sodium chloride solution and dried over anhydrous magnesium sulfate. The residue was concentrated under reduced pressure to remove the organic solvent and then purified with column chromatography (n-hexane:ethyl acetate=9:1) to obtain 164 mg (yield: 98%, 3RS,4RS/3RS, 4SR=8.5/1) of the title compound as a yellow oil.

$^1$H-NMR(270 MHz, CDCl$_3$, 3RS,4RS-compound): δ 7.29 (d, $^3$J=8.9 Hz, 2H. Ar—H), 6.90(m, 3H, Ar—H), 6.72(d, $^4$J=2.7 Hz, 1H, C8-H), 6.58(dd, $^3$J=8.6 Hz, $^4$J=2.7 Hz, 1H, Ar—H), 3.83(d, $^2$J=11.9 Hz, 1H, C2-H), 3.82(s, 3H, OCH$_3$), 3.78(s, 3H, OCH$_3$), 2.98(d, $^2$J=11.9 Hz, 1H, C2-H), 2.74(brt, 1H, C4-H), 2.57(t, $^3$J=6.9 Hz, 2H, S—CH$_2$), 2.47(t, $^3$J=6.9 Hz, 2H, S—CH$_2$), 2.13(m, 2H, alkyl-H), 1.88(m, 2H, alkyl-H), 1.50–1.08(m, 19H, C3-CH$_3$ and alkyl-H).

EXAMPLE 33

Synthesis of (3RS,4RS)- and (3RS,4SR)-7-hydroxy-3-(4-hydroxyphenyl)-3-methyl-4-[9-(4,4,5,5,5-pentafluoropentylthio)nonyl]thiochroman

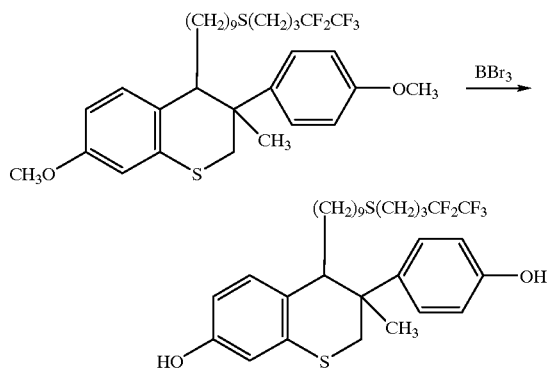

7-Methoxy-3-(4-methoxyphenyl)-3-methyl-4-[9-(4,4,5,5,5-pentafluoropentylthio)nonyl]-thiochroman (164 mg, 0.26 mmol) obtained in Example 32 was dissolved in dichloromethane (18 ml) and boron tribromide (1.85 ml, 1.0 mol/l dichloromethane solution) was added thereto at −78° C. The reaction mixture was stirred for one hour at the same temperature and for about 10 hours at room temperature. When the reaction is completed, water was added to the reaction solution which was then extracted with ethyl acetate. The organic layer was washed with sodium hydrogen sulfite solution and water and dried over anhydrous magnesium sulfate. The residue was concentrated under reduced pressure to remove the organic solvent and then purified with column chromatography (n-hexane:ethyl acetate=8:2) to obtain 109 mg (yield: 70%) of the title 3RS,4RS-compound and 9 mg (yield: 6%) of the 3RS,4SR-compound as a white solid.

$^1$H-NMR(270 MHz, CDCl$_3$, 3RS,4RS-compound): δ 7.25 (d, $^3$J=8.6 Hz, 2H, Ar—H), 6.85(dd, $^3$J=8.6 and 8.21 Hz, 3H, Ar—H), 6.67(d, $^4$J=2.6 Hz, 1H, C8-H), 6.50(dd, $^3$J=8.3 Hz, $^4$J=2.3 Hz, 1H, Ar—H), 4.94(brs, 1H, OH), 4.75(brs, 1H, OH), 3.62(d, $^2$J=11.6 Hz, 1H, C2-H), 2.96(d, $^2$J=11.6 Hz, 1H, C2-H), 2.69(brt, 1H, C4-H), 2.58(t, $^3$J=6.9 Hz, 2H, S—CH$_2$), 2.48(t, $^3$J=6.9 Hz, 2H, S—CH$_2$), 2.12(m, 2H, alkyl-H), 1.88(m, 2H, alkyl-H), 1.69–1.07(m, 19H, C3-CH$_3$ and alkyl-H).

$^1$H-NMR(270 MHz, CDCl$_3$, 3RS,4SR-compound): δ 7.24 (d, $^3$J=8.6 Hz, 2H, Ar—H), 6.65(m, 3H, Ar—H), 6.48(d, $^4$J=2.4 Hz, 1H, Ar—H), 6.31(dd, $^3$J=8.3 Hz, $^4$J=2.3 Hz, 1H, Ar—H), 4.54(brs, 1H, OH), 4.46(brs, 1H, OH), 3.21(2×d, $^2$J=not resolved, 2H, 2×C2-H), 2.85(brt, 1H, C4-H), 2.58(t, $^3$J=6.9 Hz, 2H, S—CH$_2$), 2.50(t, $^3$J=6.9 Hz, 2H, S—CH$_2$), 2.16(m, 2H, alkyl-H), 1.87(m, 2H, alkyl-H), 1.63–1.16(m, 19H, C3-CH$_3$ and alkyl-H).

EXAMPLE 34

Synthesis of (3RS,4RS)-7-hydroxy-3-(4-hydroxyphenyl)-3-methyl-4-[9-(4,4,5,5,5-pentafluoropentylsulfinyl)nonyl]thiochroman

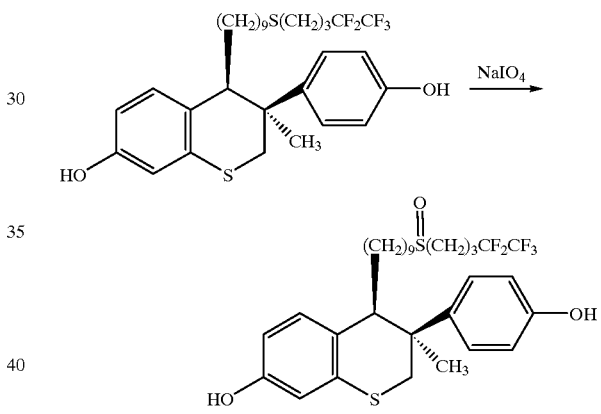

Methanol (16 ml) and water (4 ml) were added to the mixture of (3RS,4RS)-7-hydroxy-3-(4-hydroxyphenyl)-3-methyl-4-[9-(4,4,5,5,5-pentafluoropentylthio)nonyl] thiochroman (85 mg, 0.14 mmol) obtained in Example 33 and NaIO$_4$ (34 mg, 0.16 mmol), and the reaction mixture was stirred for 3.5 hours at room temperature. Water was added to the reaction solution which was then extracted with ethyl acetate. The extract was dried over anhydrous magnesium sulfate and then purified with preparative TLC (n-hexane:ethyl acetate=1:1) to obtain 39 mg (yield: 45%) of the title compound as a white solid. In this reaction, 13 mg (15%) of the unreacted starting 3RS,4RS-compound was recovered.

$^1$H-NMR(270 MHz, CD$_3$OD): δ 7.21(d, $^3$J=8.6 Hz, 2H, Ar—H), 6.81(d, $^3$J=8.3 Hz, 1H, C5-H), 6.73(d, $^3$J=8.6 Hz, 2H, Ar—H), 6.51(d, $^4$J=2.3 Hz, 1H, C8-H), 6.39(dd, 3J=8.3 Hz, $^4$J=2.3 Hz, 1H, C6-H), 3.57(d, $^2$J=11.5 Hz, 1H, C2-H), 3.26(d, $^2$J=11.5 Hz, 1H, C2-H), 2.80(m, 4H, 2×S(O)—CH$_2$), 2.27(m, 2H, alkyl-H), 2.04(m, 2H, alkyl-H), 1.67(m, 2H, alkyl-H), 1.54–1.02(m, 17H, C3-CH$_3$ and alkyl-H).

EXAMPLE 35

Synthesis of (3RS,4RS)-4-hydroxy-4-(3-hydroxyphenyl)-7-methoxymethyloxy-3-[4-(methoxymethyloxy)phenyl]-3-methyl-2,3-dihydro-4H-benzopyran

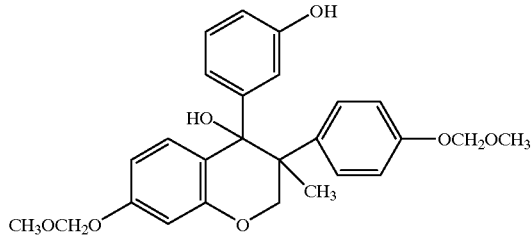

Under argon atmosphere 3-bromomagnesium phenyl trimethylsilyl ether was prepared from 3-bromophenyl trimethylsilyl ether (3 g, 12.24 mmol) and magnesium turning (300 mg, 12.34 mmol) in dry tetrahydrofuran (10 ml) and cooled to 0° C. 7-Methoxymethyloxy-3-[4-(methoxymethyloxy)phenyl]-3-methyl-2,3-dihydro-4H-benzopyran-4-one (900 mg, 2.51 mmol) dissolved in dry tetrahydrofuran (5 ml) was slowly added dropwise thereto and then refluxed for 12 hours. The reaction mixture was cooled to room temperature, quenched with water and then extracted with ethyl acetate. The organic layer was dried over anhydrous magnesium sulfate and concentrated under reduced pressure to remove the organic solvent. The concentrate was separated by column chromatography (n-hexane:ethyl acetate=2:1) to obtain 760 mg (yield: 67%) of the title compound as a foam.

EXAMPLE 36

Synthesis of (3RS,4RS)-4-(3-hydroxyphenyl)-7-methoxymethyloxy-3-[4-(methoxymethyloxy)phenyl]-3-methyl-2,3-dihydro-4H-benzopyran

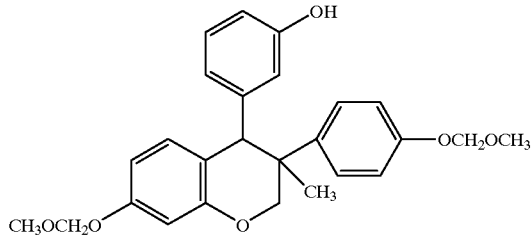

(3RS,4RS)-4-Hydroxy-4-(3-hydroxyphenyl)-7-methoxymethyloxy-3-[4-(methoxymethyloxy)phenyl]-3-methyl-2,3-dihydro-4H-benzopyran (1.19 g, 2.63 mmol) prepared in Example 35 was dissolved in methanol (50 ml), and 10% Pd/C (200 mg) was slowly added dropwise thereto. The reaction mixture was stirred under hydrogen atmosphere for 12 hours and then filtered. The filtrate was concentrated under reduced pressure to remove the organic solvent. The concentrate was separated by column chromatography (n-hexane:ethyl acetate=8:1) to obtain 594 mg (yield: 50%) of the title compound as a colorless foam.

$^1$H-NMR(300 MHz, CDCl$_3$): δ 7.17(s, 1H), 6.81(d, 2H), 6.76(s, 1H), 6.71(d, 2H), 6.59(s, 1H), 6.47(d, 1H), 6.41(m, 1H), 6.08(d, 1H), 5.92(s, 1H), 5.30(s, 1H), 5.08(s, 2H), 5.05(s, 2H), 4.53(d, 1H), 3.94(d, 1H), 3.81(s, 1H), 3.39(s, 3H), 3.36(s, 3H), 1.42(s, 3H).

EXAMPLE 37

Synthesis of (3RS,4RS)-4-[3-(4-chlorobutyloxy)phenyl]-7-methoxymethyloxy-3-[4-(methoxymethyloxy)phenyl]-3-methyl-2,3-dihydro-4H-benzopyran

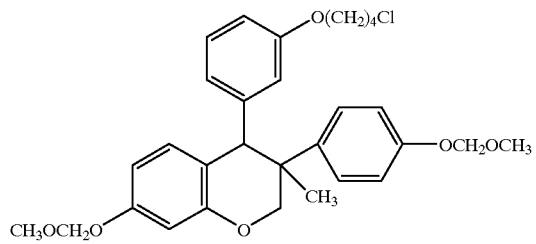

(3RS,4RS)-4-(3-Hydroxyphenyl)-7-methoxymethyloxy-3-[4-(methoxymethyloxy)phenyl]-3-methyl-2,3-dihydro-4H-benzopyran (260 mg, 0.59 mmol), 1-bromo-4-chlorobutane (0.8 ml, 2.98 mmol) and aqueous 2N-NaOH solution (0.8 ml) were dissolved in acetone (10 ml) and then stirred for 4 hours at 50° C. The reaction mixture was cooled to room temperature and then water was added thereto. The reaction solution was extracted with ethyl acetate and the organic layer was dried over anhydrous magnesium sulfate, filtered and concentrated under reduced pressure to remove the organic solvent. The concentrate was separated by column chromatography (n-hexane:ethyl acetate=4:1) to obtain 300 mg (yield: 96%) of the title compound as a colorless oil.

$^1$H-NMR(300 MHz, CDCl$_3$): δ 7.17(d, 1H), 6.79(d, 2H), 6.70(d, 2H), 6.69(s, 1H), 6.59(s, 1H), 6.45(m, 2H), 6.15(d, 1H), 5.98(s, 1H), 5.06(s, 2H), 5.01(s, 2H), 4.53(d, 1H), 3.96(d, 1H), 3.84(s, 1H), 3.60–3.47(m, 4H), 3.41(s, 3H), 3.35(s, 3H), 1.9–1.7(m, 4H), 1.42(s, 3H).

EXAMPLE 38

Synthesis of (3RS,4RS)-4-[3-(4-iodobutyloxy)phenyl]-7-methoxymethyloxy-3-[4-(methoxymethyloxy)phenyl]-3-methyl-2,3-dihydro-4H-benzopyran

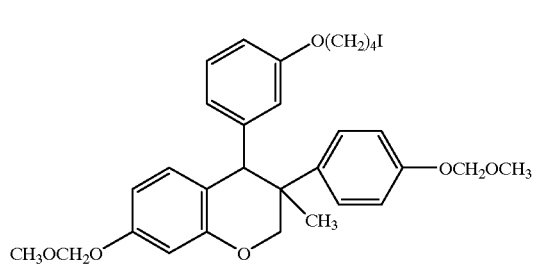

(3RS,4RS)-4-[3-(4-Chlorobutyloxy)phenyl]-7-methoxymethyloxy-3-[4-(methoxymethyloxy)phenyl]-3-methyl-2,3-dihydro-4H-benzopyran (300 mg, 0.57 mmol) and sodium iodide (260 mg, 1.73 mmol) were dissolved in methyl ethyl ketone (30 ml) and then refluxed for 12 hours. The reaction mixture was cooled to room temperature and then water was added thereto. The reaction solution was extracted with ethyl acetate and the organic layer was dried over anhydrous magnesium sulfate, filtered and then concentrated under reduced pressure to remove the organic solvent. The concentrate was separated by column chromatography (n-hexane:ethyl acetate=4:1) to obtain 340 mg (yield: 97%) of the title compound as a colorless oil.

$^1$H-NMR(300 MHz, CDCl$_3$): δ 7.17(d, 1H), 6.79(d, 2H), 6.70(d, 2H), 6.69(s, 1H), 6.59(s, 1H), 6.45(m, 2H), 6.15(d, 1H), 5.98(s, 1H), 5.06(s, 2H), 5.01(s, 2H), 4.53(d, 1H), 3.96(d, 1H), 3.84(s, 1H), 3.60–3.45(m, 2H), 3.41(s, 3H), 3.35(s, 3H), 3.13(t, 2H), 1.9–1.7(m, 4H), 1.42(s, 3H).

EXAMPLE 39

Synthesis of (3RS,4RS)-7-methoxymethyloxy-3-[4-(methoxymethyloxy)phenyl]-3-methyl-4-[3-(4-(4,4,5,5,5-pentafluoropentylthio)butyloxy)phenyl]-2,3-dihydro-4H-benzopyran

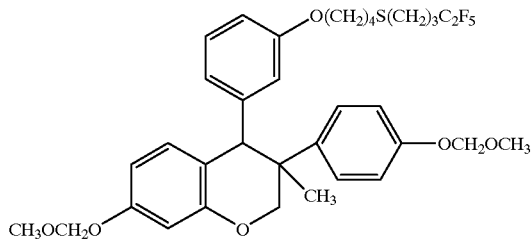

4,4,5,5,5-Pentafluoropentylthioacetate (650 mg, 2.75 mmol) was dissolved in methanol (2 ml) and aqueous 2N-NaOH solution (1.4 ml) was added thereto. The mixture was stirred for one hour at room temperature. (3RS,4RS)-4-[3-(4-Iodobutyloxy)phenyl]-7-methoxymethyloxy-3-[4-(methoxymethyloxy)phenyl]-3-methyl-2,3-dihydro-4H-benzopyran (340 mg, 0.55 mmol) dissolved in methanol (10 ml) was added dropwise thereto and then stirred for 12 hours at 60° C. The reaction mixture was cooled to room temperature and then water was added thereto. The reaction solution was extracted with ethyl acetate and the organic layer was dried over anhydrous magnesium sulfate, filtered and concentrated under reduced pressure to remove the organic solvent. The concentrate was separated by column chromatography (n-hexane:ethyl acetate=4:1) to obtain 346 mg (yield: 92%) of the title compound as a colorless oil.

$^1$H-NMR(300 MHz, CDCl$_3$): δ 7.18(d, 1H), 6.80(d, 2H), 6.71(d, 2H), 6.70(s, 1H), 6.60(s, 1H), 6.46(m, 2H), 6.16(d, 1H), 6.00(s, 1H), 5.07(s, 2H), 5.02(s, 2H), 4.54(d, 1H), 3.97(d, 1H), 3.85(s, 1H), 3.60–3.45(m, 2H), 3.42(s, 3H), 3.36(s, 3H), 2.5(m, 4H), 2.1(m, 2H), 1.81(m, 2H), 1.67(m, 4H), 1.43(s, 3H).

EXAMPLE 40

Synthesis of (3RS,4RS)-7-hydroxy-3-(4-hydroxyphenyl)-3-methyl-4-[3-(4-(4,4,5,5,5-pentafluoropentylthio)butyloxy)phenyl]-2,3-dihydro-4H-benzopyran

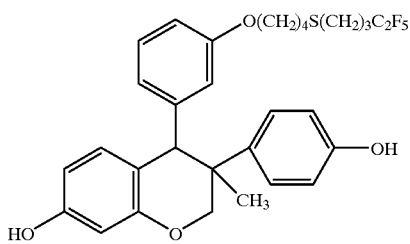

(3RS,4RS)-7-Methoxymethyloxy-3-[4-(methoxymethyloxy)phenyl]-3-methyl-4-[3-(4-(4,4,5,5,5-pentafluoropentylthio)butyloxy)phenyl]-2,3-dihydro-4H-benzopyran (274 mg, 0.4 mmol) and pyridinium p-toluenesulfonate (508 mg, 2.02 mmol) were dissolved in methanol (10 ml) and then refluxed for 14 hours. The reaction mixture was cooled to room temperature and then water was added thereto. The reaction solution was extracted with ethyl acetate and the organic layer was washed with water, dried over anhydrous magnesium sulfate and then concentrated. The residue was subjected to column chromatography (n-hexane:ethyl acetate=4:1) to obtain 167 mg (yield: 75%) of the title compound as a white foam.

$^1$H-NMR(300 MHz, CDCl$_3$): δ 6.83(m, 1H), 6.74(d, 2H), 6.65(d, 1H), 6.53(d, 2H), 6.5(m, 1H), 6.39(s, 1H), 6.27(m, 1H), 6.19(d, 1H), 5.96(s, 1H), 5.29(s, 1H), 5.22(s, 1H), 4.52(d, 1H), 3.95(d, 1H), 3.81(s, 1H), 3.6(m, 2H), 2.49(m, 4H), 2.1(m, 2H), 1.82(m, 2H), 1.65(m, 4H), 1.42(s, 3H).

EXAMPLE 41

Synthesis of (3RS,4RS)-7-hydroxy-3-(4-hydroxyphenyl)-3-methyl-4-[3-(4-(4,4,5,5,5-pentafluoropentylsulfinyl)butyloxy)phenyl]-2,3-dihydro-4H-benzopyran

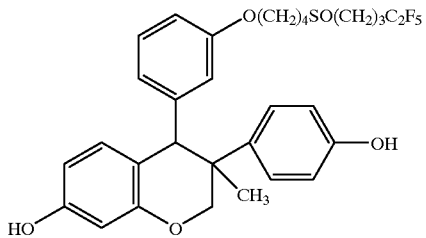

(3RS,4RS)-7-Hydroxy-3-(4-hydroxyphenyl)-3-methyl-4-[3-(4-(4,4,5,5,5-pentafluoropentylthio)butyloxy)phenyl]-2,3-dihydro-4H-benzopyran (72 mg, 0.12 mmol) was dissolved in methanol (5 ml) and water (1 ml), and NaIO$_4$ (35 mg, 0.16 mmol) was added thereto. The reaction solution was stirred for 12 hours at room temperature and then extracted with ethyl acetate. The organic layer thus separated was washed with water, dried over anhydrous magnesium sulfate and then concentrated. The residue was subjected to column chromatography (n-hexane:ethyl acetate= 2:1) to obtain 66 mg (yield: 89%) of the title compound as a white foam.

$^1$H-NMR(300 MHz, CDCl$_3$): δ 6.91(t, 1H), 6.72(s, 1H), 6.67(s, 1H), 6.58(d, 2H), 6.47(d, 1H), 6.41(s, 1H), 6.28(d, 2H), 6.17(s, 1H), 5.78(d, 1H), 4.45(m, 1H), 4.06(m, 1H), 3.78(s, 1H), 3.6(m, 1H), 3.45(m, 1H), 2.7(m, 4H), 2.2(m, 4H), 1.7(m, 4H), 1.42(s, 3H).

EXAMPLE 42

Synthesis of (3RS,4RS)-7-hydroxy-3-(4-hydroxyphenyl)-3-methyl-4-3-[4-(4,4,5,5,5-pentafluoropentylsulfonyl)butyloxy)phenyl]-2,3-dihydro-4H-benzopyran

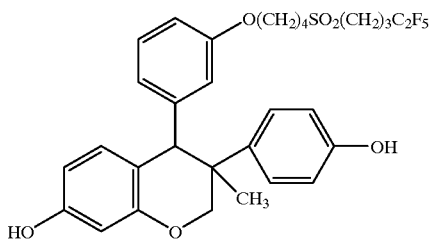

(3RS,4RS)-7-Hydroxy-3-(4-hydroxyphenyl)-3-methyl-4-[3-(4-(4,4,5,5,5-pentafluoropentylthio)butyloxy)phenyl]-2,3-dihydro-4H-benzopyran (95 mg, 0.16 mmol) was dissolved in methanol (5 ml) and water (2 ml), and oxone (147 mg, 0.24 mmol) was added thereto. The reaction solution was stirred for 4 hours at room temperature and then extracted with ethyl acetate. The organic layer thus separated was washed with water, dried over anhydrous magnesium sulfate and then concentrated. The residue was subjected to column chromatography (n-hexane:ethyl acetate= 2:1) to obtain 77 mg (yield: 77%) of the title compound as a white foam.

$^1$H-NMR(300 MHz, CDCl$_3$): δ 7.01(t, 1H), 6.83(d, 1H), 6.76(d, 2H), 6.67(d, 2H), 6.6(d, 1H), 6.50(s, 1H), 6.38(d, 2H), 6.14(s, 1H), 5.90(s, 1H), 5.11(s, 1H), 4.58(d, 1H), 4.03(d, 1H), 3.90(s, 1H), 3.6(m, 2H), 3.12(m, 4H), 2.27(m, 4H), 2.08(m, 2H), 1.82(m, 2H), 1.53(s, 3H).

EXAMPLE 43

Synthesis of thioacetic acid 2-piperidinoethyl ester

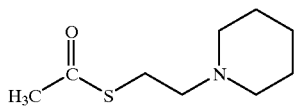

Potassium thioacetate (1.8 g, 16.35 mmol) was added to acetone (50 ml) and then stirred for 10 minutes under argon atmosphere. 1-(2-Chloroethyl)piperidine (1.61 g, 10.40 mmol) was added dropwise thereto and stirred for 18 hours under argon atmosphere at room temperature. After adding water, the reaction solution was extracted with ethyl acetate. The organic layer thus separated was dried over anhydrous magnesium sulfate and then concentrated under reduced pressure. The residue was purified with flash column chromatography (dichloromethane:ethyl acetate=19:1) to obtain 0.71 g (yield: 35%) of the title compound as a red oil.

$^1$H-NMR(CDCl$_3$): δ 3.04(t, J=8 Hz, 2H), 2.52(t, J=6 Hz, 2H), 2.45(t, J=5 Hz, 4H), 2.34(s, 3H), 1.60(m, 4H), 1.44(m, 2H).

EXAMPLE 44

Synthesis of (3RS,4RS)-7-methoxymethyloxy-3-[4-(methoxymethyloxy)phenyl]-3-methyl-4-[9-(2-piperidinoethylthio)nonyl]-2,3-dihydro-4H-benzopyran

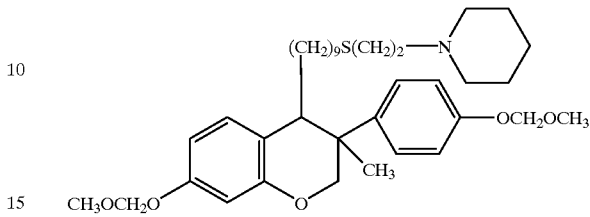

Thioacetic acid 2-piperidinoethyl ester (241 mg, 1.29 mmol) was dissolved in methanol (10 ml) and aqueous 2N-NaOH solution (1.5 ml) was added thereto. The mixture was stirred for one hour at room temperature. To the resulting solution was added (3RS,4RS)-3-[4-(methoxymethyloxy)phenyl]-3-methyl-4-[9-(p-toluenesulfonyloxy)nonyl]-2,3-dihydro-4H-benzopyran (274 mg, 0.43 mmol) dissolved in methanol (10 ml). The reaction mixture was stirred for 2 hours at 60° C. and then cooled to room temperature. After adding water, the reaction solution was extracted with ethyl acetate. The organic layer thus separated was dried over anhydrous magnesium sulfate and then concentrated under reduced pressure. The residue was purified with flash column chromatography (n-hexane:ethyl acetate=8:1→dichloromethane:ethyl acetate=19:1→dichloromethane:ethanol=9:1) to obtain 187 mg (yield: 70%) of the title compound as a pale yellow oil.

$^1$H-NMR(300 MHz, CDCl$_3$): δ 7.07(d, J=7 Hz, 2H), 6.95(d, J=9 Hz, 2H), 6.88(d, J=9 Hz, 1H), 6.50(m, 2H), 5.11(s, 2H), 5.07(s, 2H), 4.45(d, J=10 Hz, 1H), 4.20(d, J=2 Hz, 1H), 3.42(s, 6H), 2.57(m, 3H), 2.50(m, 2H), 2.44(m, 3H), 2.39(m, 4H), 1.53(m, 6H), 1.38(d, J=5 Hz, 2H), 1.30–1.05(m, 16H).

EXAMPLE 45

Synthesis of (3RS,4RS)-7-hydroxy-3-(4-hydroxyphenyl)-3-methyl-4-[9-(2-piperidinoethylthio)nonyl]-2,3-dihydro-4H-benzopyran

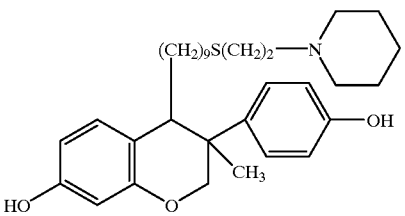

(3RS,4RS)-7-Methoxymethyloxy-3-[4-(methoxymethyloxy)phenyl]-3-methyl-4-[9-(2-piperidinoethylthio)nonyl]-2,3-dihydro-4H-benzopyran (174 mg, 0.28 mmol) and methanol solution of 5N—HCl (1 ml) were dissolved in methanol (10 ml) and then stirred for 5 hours at 40° C. The reaction solution was cooled to room temperature and, after adding water, extracted with ethyl acetate. The organic layer thus separated was dried over anhydrous magnesium sulfate and then concentrated under reduced pressure. The residue was purified with flash column chromatography (dichloromethane:ethanol=9:1) to obtain 139 mg (yield: 93%) of the title compound as a pale yellow oil.

¹H-NMR(300 MHz, CDCl₃): δ 6.99(dd, J=9 Hz, J=2 Hz, 2H), 6.82(d, J=9 Hz, 1H), 6.73(d, J=9 Hz, 2H), 6.28(m, 2H), 4.43(d, J=10 Hz, 1H), 4.17(d, J=2 Hz, 1H), 2.85(m, 1H), 2.61(m, 3H), 2.53(m, 4H), 2.42(t, J=9 Hz, 3H), 1.63(m, 5H), 1.41(m, 4H), 1.22–1.03(m, 16H).

EXAMPLE 46

Synthesis of (3RS,4RS)-7-hydroxy-3-(4-hydroxyphenyl)-3-methyl-4-[9-((2-piperidinoethyl)sulfinyl)nonyl]-2,3-dihydro-4H-benzopyran

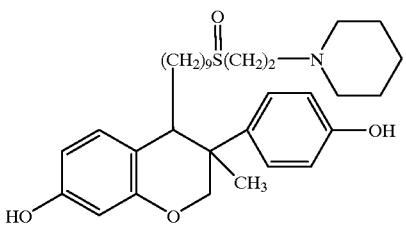

(3RS,4RS)-7-Hydroxy-3-(4-hydroxyphenyl)-3-methyl-4-[9-(2-piperidinoethylthio)nonyl]-2,3-dihydro-4H-benzopyran (126 mg, 0.24 mmol) was dissolved in methanol (5 ml)and water (1.2 ml), and NaIO₄ (62 mg, 0.29 mmol) was added thereto. The reaction was stirred for 4 hours at room temperature and then filtered. The filtrate was concentrated and the residue was purified with flash column chromatography (dichloromethane:ethanol=13:1→10:1) to obtain 96 mg (yield: 74%) of the title compound as a white foamy solid.

¹H-NMR(300 MHz, CD₃OD): δ 6.98(d, J=9 Hz, 2H), 6.76(d, J=8 Hz, 1H), 6.69(d, J=9 Hz, 2H), 6.23(dd, j=8 Hz, J=2 Hz, 1H), 6.15(d, J=2 Hz, 1H), 4.43(d, J=10 Hz, 1H), 4.15(d, J=7 Hz, 1H),2.92–2.61(m, 6H), 2.51(d, J=2 Hz, 1H), 2.47(m, 4H), 1.63(m, 2H), 1.51(m, 5H), 1.36(m, 4H), 1.22–1.05(m, 14H).

MS: 542(M+1)⁺

EXAMPLE 47

Synthesis of 4-(3-hydroxyphenyl)-4-hydroxy-7-methoxymethyloxy-3-[4-(methoxymethyloxy)phenyl]-2,3-dihydro-4H-benzopyran

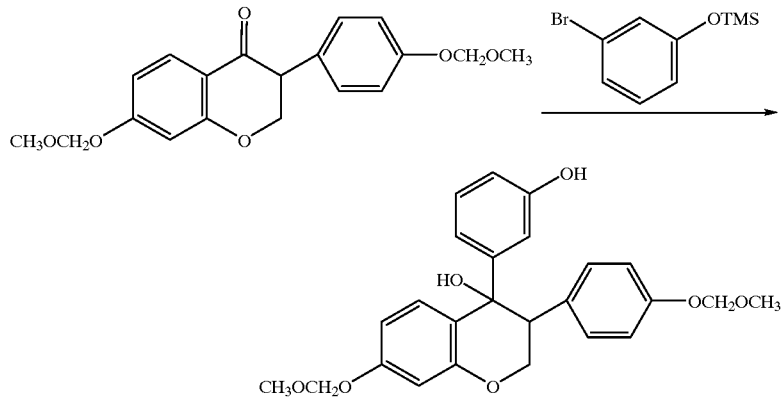

Under nitrogen atmosphere 3-bromomagnesium phenyl trimethylsilyl ether was prepared from 3-bromophenyl trimethylsilyl ether (629 mg, 2.1 mmol) and magnesium turning (52 mg, 2.1 mmol) in dry tetrahydrofuran (1.5 ml) and then cooled to −78° C. 7-Methoxymethyloxy-3-[4-(methoxymethyloxy)phenyl]-2,3-dihydro-benzopyran-4-one (250 mg, 0.7 mmol) dissolved in dry tetrahydrofuran (2 ml) was slowly added dropwise thereto and then stirred for one hour. The reaction solution was quenched with saturated aqueous ammonium chloride solution and extracted with ethyl acetate. The organic layer was dried over anhydrous magnesium sulfate and concentrated under reduced pressure to remove the organic solvent. The concentrate was separated by column chromatography (n-hexane:ethyl acetate=4:1) to obtain 283 mg (yield: 92%) of the title compound as a foam.

EXAMPLE 48

Synthesis of 4-[3-(5-chloropentyloxy)phenyl]-4-hydroxy-7-methoxymethyloxy-3-[4-(methoxymethyloxy)phenyl]-2,3-dihydro-4H-benzopyran

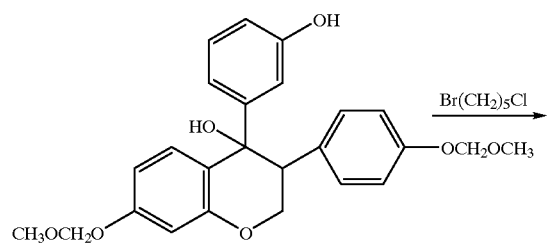

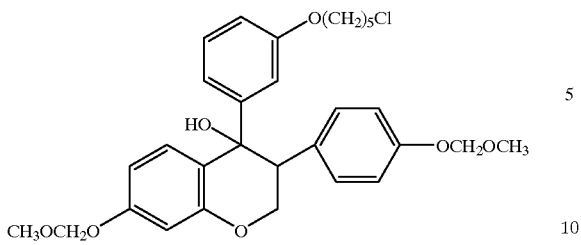

4-(3-Hydroxyphenyl)-4-hydroxy-7-methoxymethyloxy-3-[4-(methoxymethyloxy)phenyl]-2,3-dihydro-4H-benzopyran (283 mg, 0.6 mmol), 1-bromo-5-chloropentane (598 mg, 3.2 mmol) and aqueous 2N-NaOH solution (1 ml) were dissolved in acetone (3 ml) and then refluxed for 6 hours. The reaction mixture was cooled to room temperature and then water was added thereto. The reaction solution was extracted with ethyl acetate and the organic layer was dried over anhydrous magnesium sulfate, filtered and concentrated under reduced pressure to remove the organic solvent. The concentrate was separated by column chromatography (n-hexane:ethyl acetate=8:1) to obtain 307 mg (yield: 94%) of the title compound as a colorless oil.

EXAMPLE 49

Synthesis of 4-[3-(5-chloropentyloxy)phenyl]-7-methoxymethyloxy-3-[4-(methoxymethyloxy)phenyl]-2,3-dihydro-4H-benzopyran

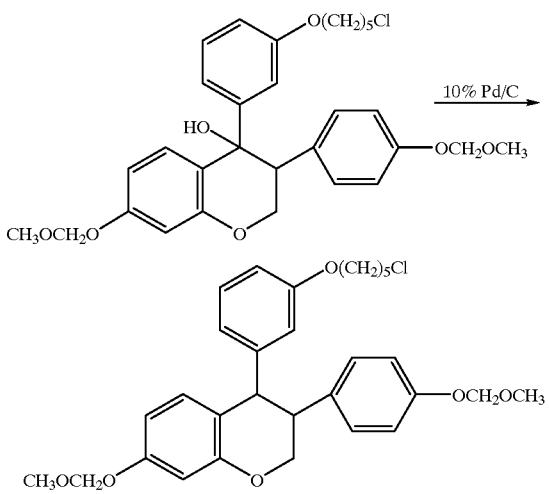

4-[3-(5-Chloropentyloxy)phenyl]-4-hydroxy-7-methoxymethyloxy-3-[4-(methoxymethyloxy)phenyl]-2,3-dihydro-4H-benzopyran (307 mg, 0.56 mmol) was dissolved in methanol (15 ml), and 10% Pd/C (102 mg) was slowly added dropwise thereto. Then the reaction mixture was stirred under hydrogen atmosphere for 2 hours and filtered. The filtrate was concentrated under reduced pressure to remove the organic solvent. The concentrate was separated by column chromatography (n-hexane:ethyl acetate=8:1) to obtain 283 mg (yield: 95%, 3RS,4RS/3RS,4SR=1:1) of the title compound as a colorless oil.

$^1$H-NMR(300 MHz, CDCl$_3$, 3RS,4RS-compound): δ 7.10 (m, 1H), 6.78 (m, 5H), 6.70(t, 3H), 6.63(s, 1H), 6.45(d, 1H), 5.90(s, 1H), 5.15(d, 4H), 4.61 (dd, 1H), 4.20(dd, 1H), 3.83(t, 2H), 3.42(s, 3H), 3.21(s, 3H), 1.80–1.17(m, 6H).

EXAMPLE 50

Synthesis of 4-[3-(5-iodopentyloxy)phenyl]-7-methoxymethyloxy-3-[4-(methoxymethyloxy)phenyl]-2,3-dihydro-4H-benzopyran

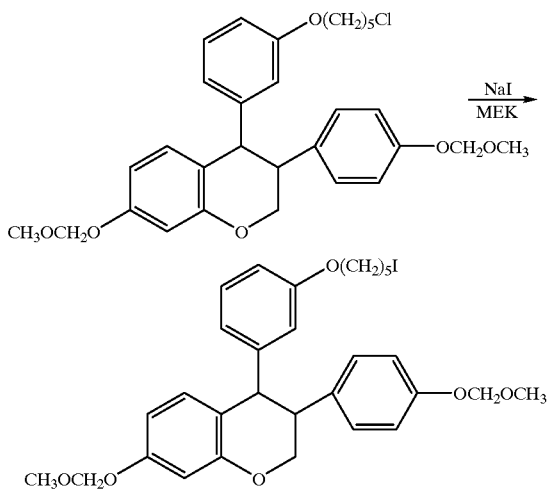

4-[3-(5-Chloropentyloxy)phenyl]-7-methoxymethyloxy-3-[4-(methoxymethyloxy)phenyl]-2,3-dihydro-4H-benzopyran (283 mg, 0.5 mmol) and sodium iodide (24 mg, 1.6 mmol) were dissolved in methyl ethyl ketone (5 ml) and then refluxed for 12 hours. The reaction mixture was cooled to room temperature and then water was added thereto. The reaction solution was extracted with ethyl acetate and the organic layer was dried over anhydrous magnesium sulfate, filtered and concentrated under reduced pressure to remove the organic solvent. The concentrate was separated by column chromatography (n-hexane:ethyl acetate=8:1) to obtain 293 mg (yield: 94%) of the title compound as a yellow oil.

EXAMPLE 51

Synthesis of 7-methoxymethyloxy-3-[4-(methoxymethyloxy)phenyl]4-3-(5-(4,4,5,5,5-pentafluoropentylthio)pentyloxy)phenyl[-2,3-dihydro-4H-benzopyran

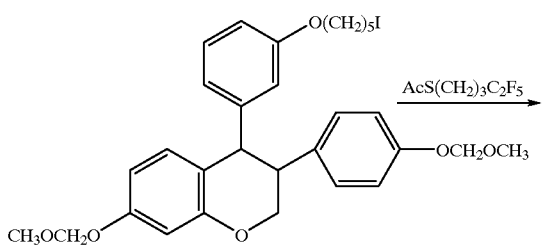

-continued

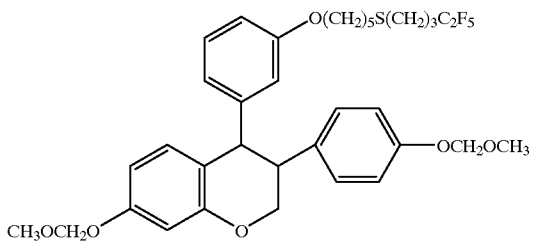

4,4,5,5,5-Pentafluoropentylthioacetate (537 mg, 2.3 mmol) was dissolved in methanol (5 ml) and aqueous 2N-NaOH solution (0.5 mg) was added thereto. The mixture was stirred for one hour at room temperature. 4-[3-(5-Iodopentyloxy)phenyl]-7-methoxymethyloxy-3-[4-(methoxymethyloxy)phenyl]-2,3-dihydro-4H-benzopyran (293 mg, 0.47 mmol) dissolved in methanol (2 ml) was added dropwise thereto and then stirred for 2 hours at 60° C. The reaction mixture was cooled to room temperature and then water was added thereto. The reaction solution was extracted with ethyl acetate and the organic layer was dried over anhydrous magnesium sulfate, filtered and concentrated under reduced pressure to remove the organic solvent. The concentrate was separated by column chromatography (n-hexane:ethyl acetate=8:1) to obtain 290 mg (yield: 89%) of the title compound as a colorless oil.

EXAMPLE 52

Synthesis of 7-hydroxy-3-(4-hydroxyphenyl)-4-[3-(5-(4,4,5,5,5-pentafluoropentylthio)pentyloxy)phenyl]-2,3-dihydro-4H-benzopyran

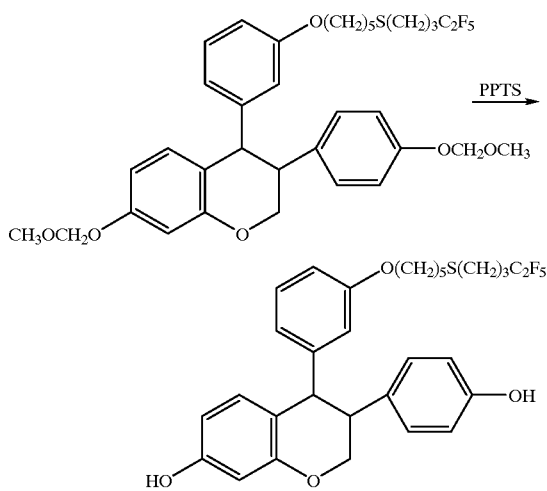

7-Methoxymethyloxy-3-[4-(methoxymethyloxy)phenyl]-4-[3-(5-(4,4,5,5,5-pentafluoropentylthio)pentyloxy)phenyl]-2,3-dihydro-4H-benzopyran (290 mg, 0.4 mmol) and pyridinium p-toluenesulfonate (1.05 g, 4 mmol) were dissolved in methanol (6 ml) and then refluxed for 8 hours. The reaction mixture was cooled to room temperature and then water was added thereto. The reaction solution was extracted with ethyl acetate and the organic layer was dried over anhydrous magnesium sulfate, filtered and then concentrated under reduced pressure to remove the organic solvent. The concentrate was separated by column chromatography (n-hexane:ethyl acetate=1:1) to obtain 177mg (yield: 74%) of the title compound as a colorless oil.

EXAMPLE 53

Synthesis of 7-hydroxy-3-(4-hydroxyphenyl)-4-[3-(5-(4,4,5,5,5-pentafluoropentylsulfinyl)pentyloxy)phenyl]-2,3-dihydro-4H-benzopyran

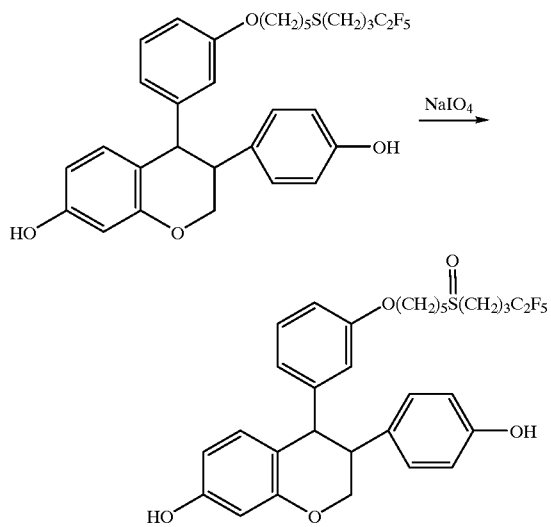

7-Hydroxy-3-(4-hydroxyphenyl)-4-[3-(5-(4,4,5,5,5-pentafluoropentylthio)pentyloxy)phenyl]-2,3-dihydro-4H-benzopyran (90 mg, 0.15 mmol) was dissolved in 1,4-dioxane (1.5 ml), methanol (1.5 ml) and water (0.38 ml), and NaIO$_4$ (35.5 mg, 0.16 mmol) was added dropwise thereto. The reaction solution was stirred for 8 hours at room temperature and then filtered. The filtrate was concentrated and the residue was separated by column chromatography (n-hexane:ethyl acetate=1:1) to obtain 58 mg (yield: 63%, 3RS,4RS/3RS,4SR=1:1) of the title compound as a colorless oil.

$^1$H-NMR(300 MHz, CDCl$_3$, 3RS,4RS-compound): δ 8.36 (s, 1H), 7.20 (dd, 1H), 6.90(d, 1H), 6.80(t, 3H), 6.52(t, 2H), 6.40(s, 1H), 6.36(m, 2H), 5.83(s, 1H), 5.15(s, 1H), 4.43(dd, 1H), 4.25(dd, 2H), 3.80–3.40(dd, 2H), 3.22–2.70(m, 4H), 2.52–2.22(m, 4H), 2.0–1.43(m, 6H).

EXAMPLE 54

Synthesis of 7-hydroxy-3-(4-hydroxyphenyl)-4-[3-(5-(4,4,5,5,5-pentafluoropentylsulfonyl)pentyloxy)phenyl]-2,3-dihydro-4H-benzopyran

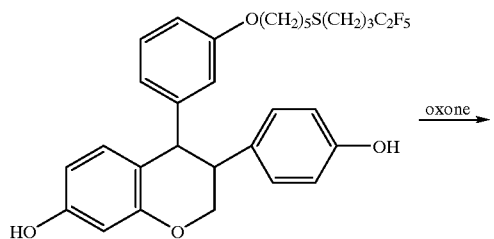

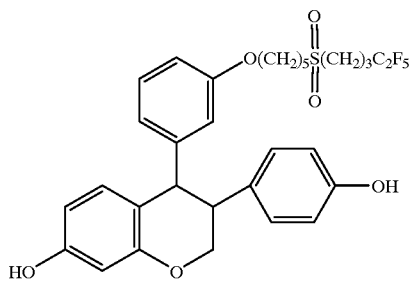

7-Hydroxy-3-(4-hydroxyphenyl)-4-[3-(5-(4,4,5,5,5-pentafluoropentylthio)pentyloxy)phenyl]-2,3-dihydro-4H-benzopyran (84 mg, 0.14 mmol) was dissolved in methanol (4 ml) and water (2 ml), and oxone (262 mg, 0.4 mmol) was added dropwise thereto. The reaction solution was stirred for 1.5 hours at room temperature and, after adding water, extracted with ethyl acetate. The organic layer thus separated was dried over anhydrous magnesium sulfate, filtered and then concentrated under reduced pressure to remove the organic solvent. The residue was separated by column chromatography (n-hexane:ethyl acetate=5:1) to obtain 36 mg (yield: 40%, 3RS,4RS/3RS,4SR=1:1) of the title compound as a colorless oil.

1H-NMR(300 MHz, CDCl$_3$, 3RS,4RS-compound): δ 7.05(dd, 1H), 6.82(dd, 1H), 6.65(t, 3H), 6.58(d, 2H), 6.40(d, 1H), 6.26(m, 2H), 6.05(s, 1H), 5.75(s, 1H), 5.16(s, 1H), 4.36(dd, 1H), 4.15(dd, 1H), 3.40–3.31(t, 2H), 3.15–2.80(m, 4H), 2.32–2.15(t, 4H), 1.75(m, 2H), 1.71–1.45(m, 4H).

EXAMPLE 55

Synthesis of 4-hydroxy-7-methoxymethyloxy-3-[4-(methoxymethyloxy)phenyl]-4-[4-(piperidinoethyloxy)phenyl]-2,3-dihydro-4H-benzopyran 4-(4-Hydroxyphenyl)-4-hydroxy-7-methoxymethyloxy-3-[4-(methoxymethyloxy)phenyl]-2,3-dihydro-4H-benzopyran (310 mg, 0.59 mmol) prepared in Example 15, [1-(2-chloroethyl)]piperidine.HCl (176 mg, 0.9 mmol) and K$_2$CO$_3$ (264 mg, 1.8 mmol) were dissolved in acetone (8 ml) and then refluxed for 62 hours. The reaction solution was cooled to room temperature and, after adding water, extracted with ethyl acetate. The organic layer thus separated was dried over anhydrous magnesium sulfate, filtered and then concentrated under reduced pressure to remove the organic solvent. The residue was separated by column chromatography (n-hexane:ethyl acetate=1:2) to obtain 83 mg (yield: 7%) of the title compound as a white foam.

$^1$H-NMR(300 MHz, CDCl$_3$): δ 7.00(d, 2H), 6.78(d, 3H), 6.62(m, 4H), 6.37(dd, 2H), 5.25(d, 2H), 4.65(dd, 1H), 4.25(dd, 1H), 3.99(t, 2H), 3.38(dd, 1H), 3.31(d, 3H), 2.78(t, 2H), 2.43(m, 4H), 1.55(m, 4H), 1.35(m, 3H).

EXAMPLE 56

Synthesis of 7-hydroxy-3-(4-hydroxyphenyl)-4-[4-(piperidinoethyloxy)phenyl]-2H-benzopyran

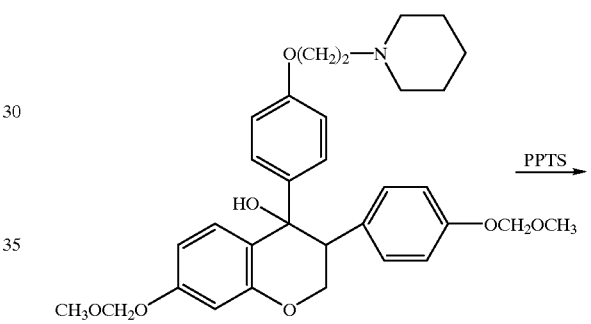

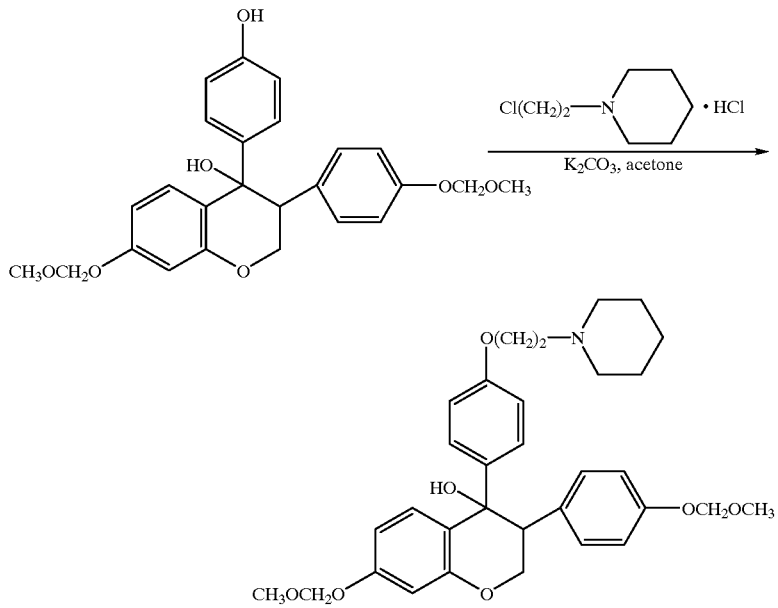

-continued

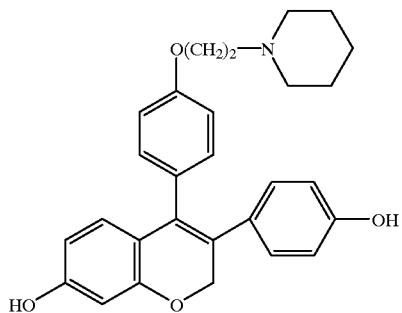

4-Hydroxy-7-methoxymethyloxy-3-[4-(methoxymethyloxy)phenyl]-4-[4-(piperidinoethyloxy)phenyl]-2,3-dihydro-4H-benzopyran (83 mg, 0.14 mmol) and pyridinium p-toulenesulfonate (214 mg, 1.4 mmol) were dissolved in methanol (6 ml) and then refluxed for 12 hours. The reaction solution was cooled to room temperature and, after adding water, extracted with ethyl acetate. The organic layer thus separated was dried over anhydrous magnesium sulfate, filtered and then concentrated under reduced pressure to remove the organic solvent. The residue was separated by column chromatography (n-hexane:ethyl acetate=1:4) to obtain 23 mg (yield: 37%) of the title compound as a foam.

$^1$H-NMR(300 MHz, CDCl$_3$): δ 6.95(d, 2H), 6.78(d, 2H), 6.65–6.48(m, 5H), 6.39(d, 1H), 6.21(dd, 1H), 5.00(s, 2H), 3.99(t, 2H), 2.76(t, 2H), 2.5(m, 4H), 1.62(m, 4H), 1.43(m, 2H).

EXAMPLE 57

Synthesis of 7-methoxy-3-(4-methoxyphenyl)-3-methylthiochroman-4-one

The process for preparing 7-methoxy-3-(4-methoxyphenyl)-3-methylthiochroman-4-one described hereinafter corresponds to the process 7 depicted in the reaction scheme VII.

(1) To a solution of oxalic acid diethyl ester (18.8 ml, 0.14 mol) in tetrahydrofuran (10 ml) and benzene (10 ml) was added sodium hydride (80% oil suspension, 6.5 g, 0.22 mol) and then stirred for 10 minutes under argon atmosphere. A benzene solution (100 ml) of 2-(p-methoxyphenyl)acetic acid ethyl ester (1) (27.0 g, 0.14 mol) was added to the resulting solution and stirred for 3 days at room temperature. The reaction solution was quenched with aqueous 2N HCl solution and extracted with ether. The organic layer was washed with saturated saline, dried over anhydrous magnesium sulfate and then distilled under reduced pressure to remove the solvent. Thus, 48.0 g of the crude product was obtained. The obtained crude product was dissolved in water (150 ml) and 37% formalin (25 ml, 0.31 mol) was added dropwise thereto. To the reaction mixture was added dropwise aqueous potassium carbonate solution (24 g, 0.17 mol, 100 ml) and then stirred for 24 hours. The reaction solution was extracted with ether, and the organic layer was washed with saturated saline, dried over anhydrous magnesium sulfate and distilled under reduced pressure to remove the solvent. The obtained crude product was then purified with silica gel column chromatography (ethyl acetate:hexane=1:5) to obtain 27.0 g (yield: 94%) of ethyl α-(4-methoxyphenyl)acrylate (2).

$^1$H-NMR(CDCl$_3$): δ 7.37, 6.88(4H, AA'BB', J=9 Hz, Ar—H), 6.25(1H, s, olefin-H), 5.82(1H, s, olefin-H), 4.28 (2H, q, J=7 Hz, CO$_2$CH$_2$), 3.82(3H, s, OCH$_3$), 1.33(3H, t, J=7 Hz, CH$_2$CH$_3$).

(2) To tetrahydrofuran solution (150 ml) of ethyl α-(4-methoxyphenyl)acrylate (2) (26.0 g, 0.13 mol) obtained above and 3-methoxybenzenethiol (15.6 ml, 0.13 mol) was added tetrahydrofuran solution (6.24 ml, 1.0 M, 6.24 mmol) of tetrabutylammoniumfluoride under argon atmosphere and then stirred for 10 minutes at room temperature. The reaction solution was distilled under reduced pressure to remove the solvent and the obtained crude product was then purified with silica gel column chromatography (ethyl acetate:hexane=1:5) to obtain 30.2 g (yield: 70%) of ethyl 2-(4-methoxyphenyl)-3-(3-methoxyphenylthio)propionate (3).

$^1$H-NMR(CDCl$_3$): δ 7.23–7.18(3H, m, Ar—H), 6.94–6.73(5H, m, Ar—H), 4.14(2H, q, J=7 Hz, CO$_2$CH$_2$), 3.79(6H, s, OCH$_3$×2), 3.74(1H, dd, J=9, 6 Hz, CHCO$_2$), 3.55(1H, dd, J=14, 9 Hz, 2-H), 3.21(1H, dd, J=14, 6 Hz, 2-H), 1.21 (3H, t, J=7 Hz, CH$_2$CH$_3$).

(3) To acetone solution (300 ml) of ethyl 2-(4-methoxyphenyl)-3-(3-methoxyphenylthio)propionate (3) (30.2 g, 87.3 mmol) obtained above was added aqueous 6N—HCl solution (200 ml) and then heated under refluxing for 60 hours. The reaction solution was extracted with ether, and the organic layer was alkalized with aqueous 20% NaOH solution. Then the aqueous layer was separated, acidified with 20% HCl solution and extracted with ether. The ether layer was washed with saturated saline, dried over anhydrous magnesium sulfate and then distilled under reduced pressure to remove the solvent to obtain 25.4 g (yield: 91%) of 2-(4-methoxyphenyl)-3-(3-methoxyphenylthio)propionic acid (4).

(4) To acetonitrile solution (120 ml) of 2-(4-methoxyphenyl)-3-(3-methoxyphenylthio)propionic acid (4) (12.8 g, 40.3 mmol) obtained above was added potassium carbonate (1.59 g, 11.5 mmol) and phosphorus oxychloride (18.7 ml, 200 mmol) at 0° C. and then stirred for 18 hours at 60° C. The reaction solution was quenched with ice-water and extracted with ether. The organic layer was washed with saturated saline, dried over anhydrous magnesium sulfate and then distilled under reduced pressure to remove the solvent. The obtained crude product was washed with ether to obtain 6.8 g of the first crop of 7-methoxy-3-(4-methoxyphenyl)thiochroman-4-one (5). Further, the filtrate was concentrated and the residue was then purified with silica gel column chromatography (ethyl acetate:hexane=1:3) to obtain 1.0 g of the second crop of 7-methoxy-3-(4-methoxyphenyl)thiochroman-4-one (5) (total yield: 7.8 g, 65%). NMR data of the compound (5) was identical to that described in Example 25.

The process for preparing the title compound, 7-methoxy-3-(4-methoxyphenyl)-3-methylthiochroman-4-one, from the compound (5) obtained above is identical to that of Example 26.

EXAMPLE 58

Synthesis of 7-hydroxy-3-(4-hydroxyphenyl)-3-methylthiochroman-4-one

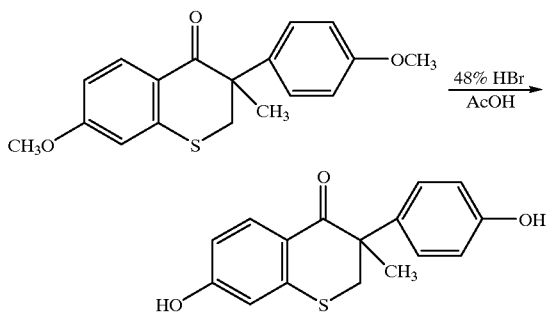

To acetic acid solution (15 ml) of 7-methoxy-3-(4-methoxyphenyl)-3-methylthiochroman-4-one (2.82 g, 8.99 mmol) was added aqueous 48% HBr solution (13 ml) and the mixture was heated under refluxing for 24 hours. The reaction solution was extracted with ethyl acetate, and the organic layer was washed with saturated aqueous sodium hydrogen carbonate solution and saturated saline, dried over anhydrous magnesium sulfate and then distilled under reduced pressure to remove the solvent. The crude product thus obtained was purified with silica gel column chromatography (ethyl acetate:hexane=2:1) to obtain 2.46 g (yield: 96%) of the title compound.

$^1$H-NMR(270 MHz, $d_6$-DMSO): δ 7.95(1H, d, J=9 Hz, 5-H), 7.00, 6.65(4H, AA'BB', J=9 Hz, Ar—H), 6.60(1H, dd, J=9, 2 Hz, 6-H), 6.47(1H, d, J=2 Hz, 8-H), 3.55(2H, ABq, J=12 Hz, 2-H), 1.38(3H, S, CH$_3$).

EXAMPLE 59

Synthesis of 7-methoxymethyloxy-3-[4-(methoxymethyloxy)phenyl]-3-methylthiochroman-4-one

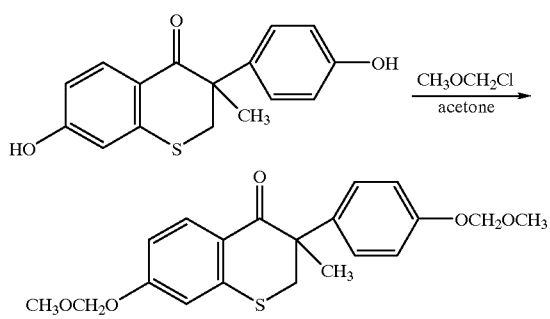

To dry acetone solution (100 ml) of 7-hydroxy-3-(4-hydroxyphenyl)-3-methylthiochroman-4-one (2.30 g, 8.04 mmol) were added potassium carbonate (8.87 g, 64.3 mmol) and methoxymethyl chloride (4.64 ml, 61.5 mmol), and the mixture was heated under refluxing for 40 hours. After adding water, the reaction solution was extracted with ethyl acetate. The organic layer was washed with saturated saline, dried over anhydrous magnesium sulfate and then distilled under reduced pressure to remove the solvent. The crude product thus obtained was purified with silica gel column chromatography (ethyl acetate:hexane=1:3) to obtain 2.65 g (yield: 88%) of the title compound.

$^1$H-NMR(CDCl$_3$): δ 8.18(1H, d, J=9 Hz, 5-H), 7.14, 6.96(4H, AA'BB', J=9 Hz, Ar—H), 6.80(1H, dd, J=9, 2 Hz, 6-H), 6.74(1H, d, J=2 Hz, 8-H), 5.35, 5.22(each 2H, each s, OCH$_2$OCH$_3$), 3.51, 3.44(each 1H, each d, J=4 Hz, 2-H), 3.44(6H, s, OCH$_3$×2), 1.47(3H, s, 3-CH$_3$).

EXAMPLE 60

Synthesis of 4-(4-t-butyldimethylsilyloxyphenyl)-4-hydroxy-7-methoxymethyloxy-3-[4-(methoxymethyloxy)phenyl]-3-methylthiochroman

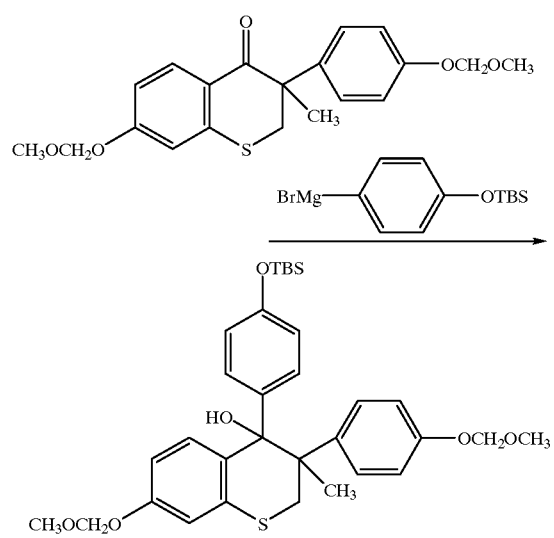

Under argon atmosphere dibromoethane (0.11 ml, 1.28 mmol) was added dropwise to tetrahydrofuran suspension (5 ml) of magnesium turning (224 mg, 9.33 mmol) and the mixture was stirred for 10 minutes at 60° C. At the same temperature, tetrahydrofuran solution (5 ml) of p-bromo-t-butyldimethylsilyloxybenzene (2.30 g, 8.01 mmol) was added dropwise thereto and the mixture was heated under refluxing for 1.5 hours. To the resulting solution was added dropwise tetrahydrofuran solution (5 ml) of 7-methoxymethyloxy-3-[4-(methoxymethyloxy)phenyl]-3-methylthiochroman-4-one (1.00 g, 2.67 mmol) and the mixture was heated under refluxing for 3 hours. After adding saturated aqueous ammonium chloride solution, the reaction solution was extracted with ethyl acetate, and the organic layer was washed with saturated saline, dried over anhydrous magnesium sulfate and then distilled under reduced pressure to remove the solvent. The crude product thus obtained was purified with silica gel column chromatography (ethyl acetate:hexane=1:4) to obtain 1.29 g (yield: 83%) of the title compound.

$^1$H-NMR(270 MHz, CDCl$_3$):δ 7.25–6.60(11H, m, Ar—H), 5.15, 5.14(each 2H, each s, OCH$_2$OCH$_3$), 4.28(1H, d, J=12 Hz, 2-H), 3.48, 3.46(each 3H, each s, OCH$_3$×2), 2.73(1H, d, J=12 Hz, 2-H), 1.45(3H, s, 3-CH$_3$), 0.98(9H, s, t-Bu), 0.19(6H, s, SiCH$_3$×2).

EXAMPLE 61

Synthesis of (3RS, 4RS)-4-(4-t-butyldimethylsilyloxyphenyl)-7-methoxymethyloxy-3-[4-(methoxymethyloxy)phenyl]-3-methylthiochroman

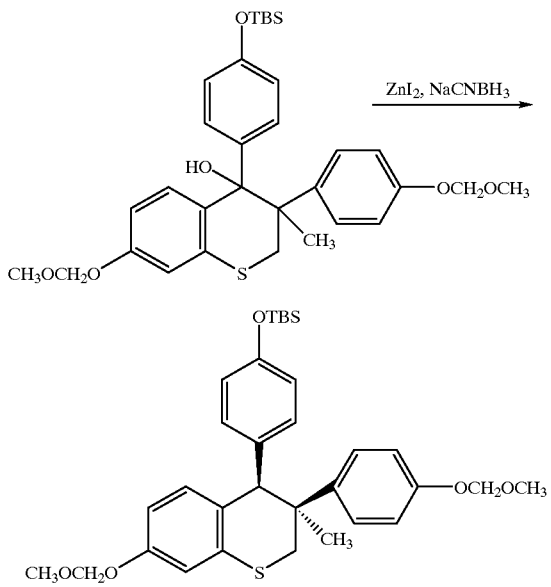

To dichloromethane solution (30 ml) of 4-(4-t-butyldimethylsilyloxyphenyl)-4-hydroxy-7-methoxymethyloxy-3-[4-(methoxymethyloxy)phenyl]-3-methylthiochroman (1.134 g, 1.95 mmol) were added zinc iodide (1.367 g, 4.9 mmol) and sodium cyanoborohydride (797 mg, 12.7 mmol), and the resulting mixture was stirred for 2 hours at room temperature. After adding acetone (5 ml) and water, the reaction solution was extracted with dichloromethane and the organic layer was washed with saturated saline, dried over anhydrous magnesium sulfate and distilled under reduced pressure to remove the organic solvent. The crude product thus obtained was purified with silica gel column chromatography (ethyl acetate:hexane=1:4) to obtain 783 mg (yield: 71%) of the title compound.

$^1$H-NMR(270 MHz, CDCl$_3$): δ 7.34, 6.90(4H, AA'BB', J=9 Hz, Ar—H), 7.00, 6.88(4H, AA'BB', J=8 Hz, Ar—H), 6.72(1H, d, J=8 Hz, 5-H), 6.71(1H, d, J=3Hz, 8-H), 6.57(1H, dd, J=8, 3 Hz, 6-H), 5.12(2H, s, OCH$_2$OCH$_3$), 5.06(2H, d, J=1 Hz, OCH$_2$OCH$_3$), 4.40(1H, s, 4-H), 3.46, 3.43(each 3H, each s, OCH$_3$× 2), 3.22(1H, d, J=13 Hz, 2-H), 3.09(1H, d, J=13 Hz, 2-H), 1.15(3H, s, 3-CH$_3$), 0.97(9H, s, t-Bu), 0.18(6H, s, SiCH$_3$×2).

EXAMPLE 62

Synthesis of (3RS,4RS)-4(4-hydroxyphenyl)-7-methoxymethyloxy-3-[4-(methoxymethyloxy)phenyl]-3-methylthiochroman

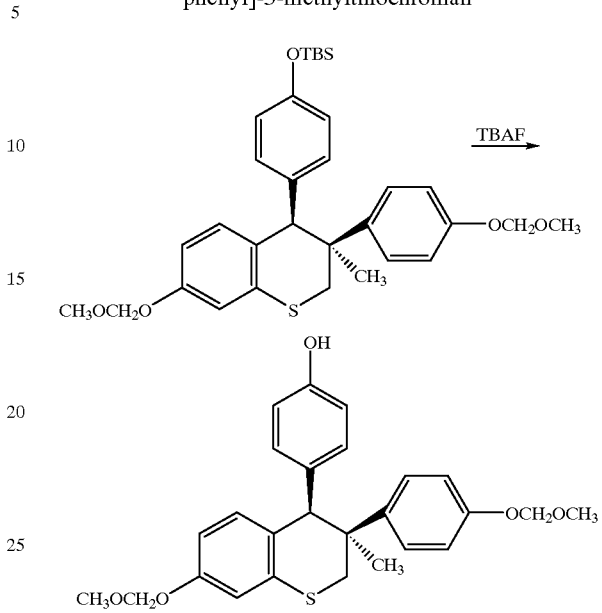

Under argon atmosphere, tetrahydrofuran solution of tetrabutylammonium fluoride (1.0M, 2.27 ml, 2.27 mmol) was added dropwise to tetrahydrofuran solution (35 ml) of (3RS,4RS)-4-(4-t-butyldimethylsilyloxyphenyl)-7-methoxymethyloxy-3-[4-(methoxymethyloxy)phenyl]-3-methylthiochroman (856 mg, 1.51 mmol) at 0° C. and the resulting mixture was stirred for 2 hours. After adding water, the reaction solution was extracted with ethyl acetate. The organic layer was washed with saturated saline, dried over anhydrous magnesium sulfate and then distilled under reduced pressure to remove the solvent. The crude product thus obtained was purified with silica gel column chromatography (ethyl acetate:hexane=1:2) to obtain 682 mg (yield: 100%) of the title compound.

$^1$H-NMR(270 MHz, CDCl$_3$): δ 7.32, 6.90(4H, AA'BB', J=8 Hz, Ar—H), 7.02, 6.86(4H, AA'BB', J=8 Hz, Ar—H), 6.72(1H, d, J=8 Hz, 5-H), 6.70(1H, d, J=3 Hz, 8-H), 6.57 (1H, dd, J=8, 3 Hz, 6-H), 5.12(2H, s, OCH$_2$OCH$_3$), 5.05(2H, d, J=1 Hz, OCH$_2$OCH$_3$), 4.76(1H, brs, OH), 4.40(1H, s, 4-H), 3.46, 3.43(each 3H, each s, OCH$_3$×2), 3.22(1H, d, J=13 Hz, 2-H), 3.09(1H, d, J=13 Hz, 2-H), 1.15(3H, s, 3-CH$_3$).

EXAMPLE 63

Synthesis of 5-(5-chloropentylthio)-1,1,1,2,2-pentafluoropentane

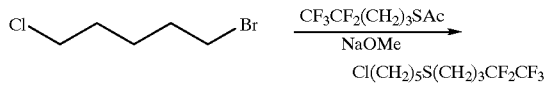

Under argon atmosphere sodium methoxide-methanol solution (1.0M, 1.7 ml, 1.7 mmol) was added dropwise to methanol solution (5 ml) of 4,4,5,5,5-pentafluoropentylthioacetate (400 mg, 1.69 mmol) at room temperature and stirred for 20 minutes. To the resulting solution was added dropwise methanol solution (5 ml) of 5-chloro-1-bromopentane (344 mg, 1.86 mmol), and the mixture was stirred for 20 hours. After adding saturated aqueous sodium hydrogen carbonate solution, the reaction solution was extracted with ether. The organic layer was washed with saturated saline, dried over anhydrous magnesium sulfate and then distilled under reduced pressure to remove the solvent. The crude product thus obtained was purified with silica gel column chromatography (ethyl acetate:hexane=1:5) to obtain 463 mg (yield: 82%) of the title compound.

$^1$H-NMR(CDCl$_3$): δ 3.54(2H, t, J=7 Hz, ClCH$_2$), 2.59, 2.53(each 2H, each t, J=7 Hz, CH$_2$SCH$_2$), 2.25–1.56(10H, m, alkyl-H).

EXAMPLE 64

Synthesis of 5-(5-chloropentylsulfonyl)-1,1,1,2,2-pentafluoropentane

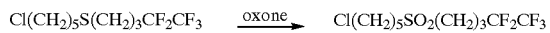

Aqueous solution (2 ml) of oxone (865 mg, 1.41 mmol) was added dropwise to tetrahydrofuran-methanol (2:1) solution (3 ml) of 5-5-chloropentylthio)-1,1,1,2,2-pentafluoropentane (210 mg, 0.70 mmol) at 0° C. and stirred for 5 hours. After adding aqueous sodium thiosulfate solution, the reaction solution was extracted with ether. The organic layer was washed with saturated saline, dried over anhydrous magnesium sulfate and then distilled under reduced pressure to remove the solvent. The crude product thus obtained was purified with silica gel column chromatography (ethyl acetate:hexane=1:10) to obtain 209 mg (yield: 90%) of the title compound.

$^1$H-NMR(CDCl$_3$): δ 3.56(2H, t, J=7 Hz, ClCH$_2$), 3.08–2.98(4H, m, CH$_2$SO$_2$CH$_2$), 2.40–1.60(10H, m, alkyl-H).

EXAMPLE 65

Synthesis of (3RS,4RS)-7-methoxymethyloxy-3-[4-(methoxymethyloxy)phenyl]-3-methyl-4-[4(5(4,4,5,5,5-pentafluoropentylsulfonyl)pentyloxy)phenyl]thiochroman

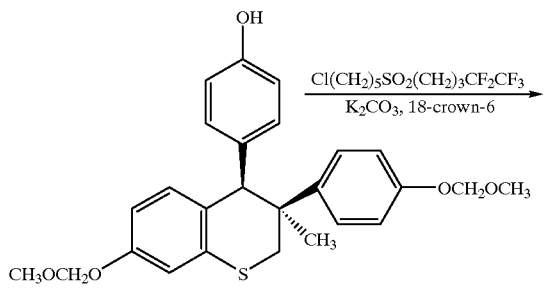

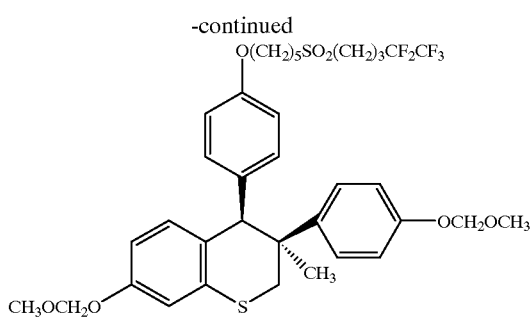

5-(5-Chloropentylsulfonyl)-1,1,1,2,2-pentafluoropentane (27 mg, 0.082 mmol), potassium carbonate (34 mg, 0.25 mmol) and 18-crown-6 (21 mg, 0.08 mmol) were added to benzene-dimethylformamide (1:1) solution (2 ml) of (3RS,4RS)-4-(4-hydroxyphenyl)-7-methoxymethyloxy-3-[4-(methoxymethyloxy)phenyl]-3-methylthiochroman (37 mg, 0.082 mmol) and then stirred for 8 hours at 100° C. under argon atmosphere. After adding water, the reaction solution was extracted with ethyl acetate. The organic layer was washed with saturated saline, dried over anhydrous magnesium sulfate and distilled under reduced pressure to remove the solvent. The crude product thus obtained was purified using silica gel plate (ethyl acetate:hexane=1:2) to obtain 41 mg (yield: 67%) of the title compound.

$^1$H-NMR(270 MHz, CDCl$_3$): δ 7.37, 6.90(4H, AA'BB', J=9 Hz, Ar—H), 7.06, 6.85(4H, AA'BB', J=8 Hz, Ar—H), 6.77(1H, d, J=9 Hz, 5-H), 6.70(1H, d, J=3 Hz, 8-H), 6.56 (1H, dd, J=9, 3 Hz, 6-H), 5.12(2H, s, OCH$_2$OCH$_3$), 5.05(2H, d, J=1 Hz, OCH$_2$OCH$_3$), 4.41(1H, s, 4-H), 3.94(2H, t, J=7 Hz, ArOCH$_2$CH$_2$), 3.46, 3.42 (each 3H, each s, OCH$_3$×2), 3.22(1H, d, J=13 Hz, 2-H), 3.09(1H, d, J=13 Hz, 2-H), 3.05–2.99(4H, m, CH$_2$SO$_2$CH$_2$), 2.38–1.60(10H, m, alkyl-H), 1.15(3H, s, 3-CH$_3$).

EXAMPLE 66

Synthesis of (3RS,4RS)-7-hydroxy-3-(4-hydroxyphenyl)-3-methyl-4-[4-(5-(4,4,5,5,5-pentafluoropentylsulfonyl)pentyloxy)phenyl]thiochroman

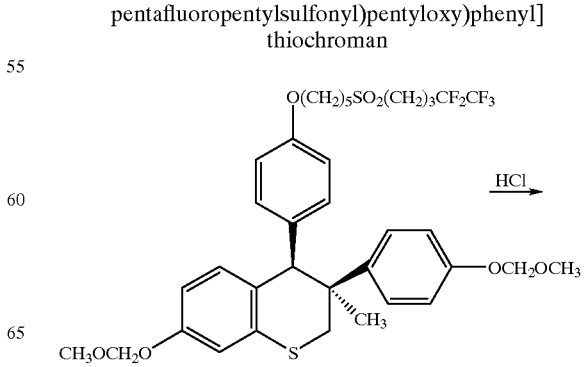

-continued

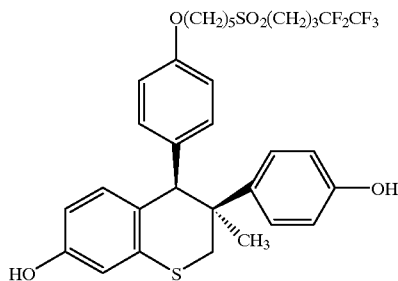

Aqueous 6N—HCl solution (1 ml) was added to tetrahydrofuran solution (1.5 ml) of (3RS,4RS)-7-methoxymethyloxy-3-[4-(methoxymethyloxy)phenyl]-3-methyl-4-[4-(5-(4,4,5,5,5-pentafluoropentylsulfonyl)pentyloxy)phenyl]thiochroman (37 mg, 0.050 mmol) and then stirred for one hour. After adding water, the reaction solution was extracted with ethyl acetate. The organic layer was washed with saturated saline, dried over anhydrous magnesium sulfate and then distilled under reduced pressure to remove the solvent. The crude product thus obtained was purified using silica gel plate (ethyl acetate:hexane=1:2) to obtain 22 mg (yield: 70%) of the title compound.

$^1$H-NMR(270 MHz, CDCl$_3$): δ 7.27(2H, d, J=8 Hz, Ar—H), 7.05(2H, d, J=8 Hz, Ar—H), 6.79–6.68(5H, m, Ar—H), 6.48(1H, d, J=3 Hz, 8-H), 6.37(1H, dd, J=9, 3 Hz, 6-H), 4.62(2H, s, OH×2), 4.37(1H, s, 4-H), 3.94(2H, t, J=7 Hz, ArOC$\underline{H}$CH$_2$), 3.19(1H, d, J=13 Hz, 2-H), 3.09(1H, d, J=13 Hz, 2-H), 3.10–2.98(4H, m, CH$_2$SO$_2$CH$_2$), 2.38–1.60 (10H, m, alkyl-H), 1.16(3H, s, 3-CH$_3$).

EXAMPLE 67

Synthesis of (3RS,4RS)-4-[4-(4-chlorobutyloxy)phenyl]-7-methoxymethyloxy-3-[4-(methoxymethyloxy)phenyl]-3-methylthiochroman

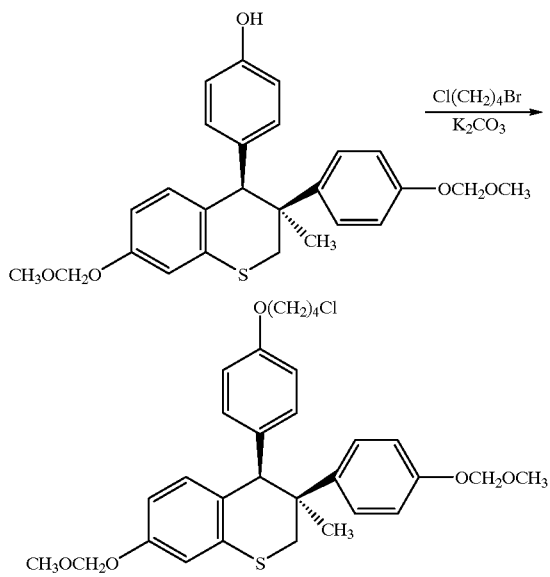

To acetone solution (2 ml) of (3RS,4RS)-4-(hydroxyphenyl)-7-methoxymethyloxy-3-[4-(methoxymethyloxy)phenyl]-3-methylthiochroman (70 mg, 0.15 mmol) were added 1-bromo-4-chlorobutane (36 μl, 0.31 mmol) and potassium carbonate (64 mg, 0.46 mmol), and the resulting mixture was heated under refluxing for 20 hours. After adding water, the reaction solution was extracted with ethyl acetate. The organic layer was washed with saturated saline, dried over anhydrous magnesium sulfate and then distilled under reduced pressure to remove the solvent. The crude product thus obtained was purified using silica gel plate (ethyl acetate:hexane=1:2) to obtain 73 mg (yield: 87%) of the title compound.

$^1$H-NMR(270 MHz, CDCl$_3$): δ 7.34, 6.90(4H, AA'BB', J=9 Hz, Ar—H), 7.05, 6.86(4H, AA'BB', J=9 Hz, Ar—H), 6.77(1H, d, J=9 Hz, 5-H), 6.70(1H, d, J=3 Hz, 8-H), 6.55 (1H, dd, J=8, 3 Hz, 6-H), 5.12(2H, s, OC$\underline{H}_2$OCH$_3$), 5.05(2H, d, J=1 Hz, OC$\underline{H}_2$OCH$_3$), 4.41(1H, s, 4-H), 3.95(2H, t, J=7 Hz, ArOC$\underline{H}_2$CH$_2$), 3.61(2H, t, J=6 Hz, ClCH$_2$), 3.45, 3.42 (each 3H, each s, OCH$_3$×2), 3.22(1H, d, J=13 Hz, 2-H), 3.09(1H, d, J=13 Hz, 2-H), 2.00–1.88(4H, m, alkyl-H), 1.15(3H, s, 3-CH$_3$).

EXAMPLE 68

Synthesis of (3RS,4RS)-7-methoxymethyloxy-3-[4-(methoxymethyloxy)phenyl]-3-methyl-4-[4-(4-piperidinobutyloxy)phenyl]thiochroman

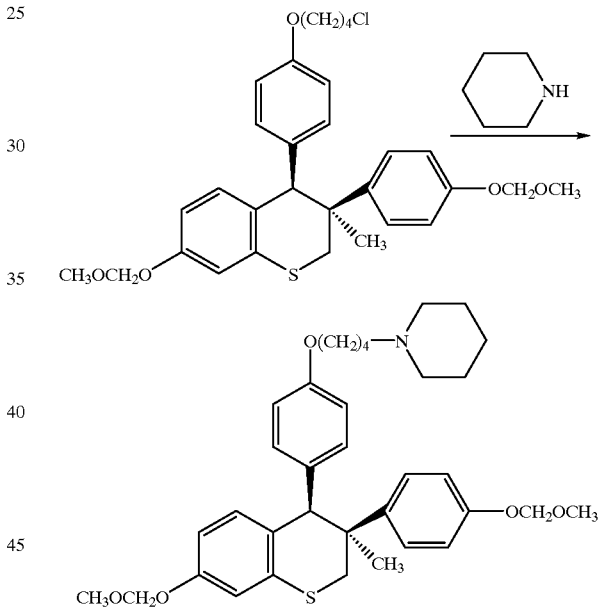

Piperidine (40 μl, 0.405 mmol) was added to ethanol solution (2 ml) of (3RS,4RS-4-[4-(4-chlorobutyloxy)phenyl]-7-methoxymethyloxy-3-[4-(methoxymethyloxy)phenyl]-3-methylthiochroman (73 mg, 0.135 mmol) and then heated under refluxing for 24 hours. The reaction solution was distilled under reduced pressure to remove the solvent. The crude product thus obtained was purified with amino silica gel chromatography (ethyl acetate:hexane=1:5) to obtain 55 mg (yield: 69%) of the title compound.

$^1$H-NMR(270 MHz, CDCl$_3$): δ 7.34, 6.90(4H, AA'BB', J=9 Hz, Ar—H), 7.05, 6.86(4H, AA'BB', J=9 Hz, Ar—H), 6.77(1H, d, J=9 Hz, 5-H), 6.70(1H, d, J=3 Hz, 8-H), 6.55 (1H, dd, J=8, 3 Hz, 6-H), 5.11(2H, s, OC$\underline{H}_2$OCH$_3$), 5.05(2H, d, J=1 Hz, OC$\underline{H}_2$OCH$_3$), 4.41(1H, s, 4-H), 3.93(2H, t, J=7 Hz, ArOC$\underline{H}$2CH$_2$), 3.61(2H, t, J=6 Hz, ClCH$_2$), 3.45, 3.42 (each 3H, each s, OCH$_3$×2), 3.22(1H, d, J=13 Hz, 2-H), 3.09(1H, d, J=13 Hz, 2-H), 2.50–2.30(6H, m, NCH$_2$×3), 1.85–1.35(10H, m, alkyl-H), 1.15(3H, s, 3-CH$_3$).

EXAMPLE 69

Synthesis of (3RS,4RS)-7-hydroxy-3-(4-hydroxyphenyl)-3-methyl-4-[4-piperidinobutyloxy)phenyl]thiochroman

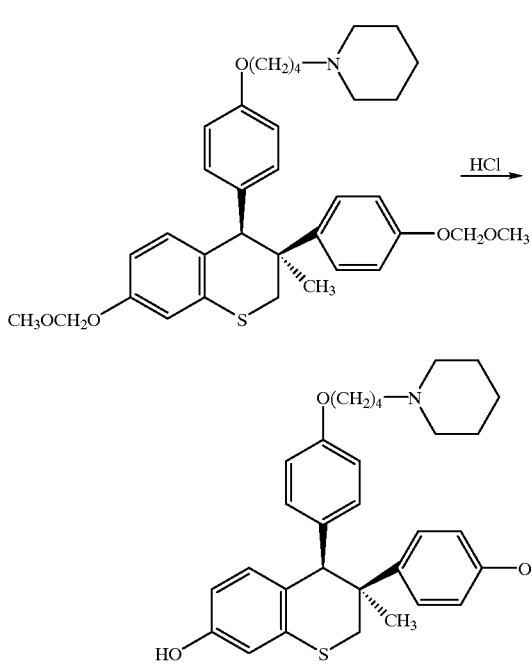

To tetrahydrofuran solution (3 ml) of (3RS,4RS)-7-methoxymethyloxy-3-[4-(methoxymethyloxy)phenyl]-3-methyl-4-[4-(4-piperidinobutyloxy)phenyl]thiochroman (55 mg, 0.093 mmol) was added aqueous 10% HCl solution (2 ml) and the resulting mixture was stirred for 20 hours. The reaction solution was distilled under reduced pressure to remove the solvent. The crude product thus obtained was purified with amino silica gel chromatography (ethyl acetate) to obtain 25 mg (yield: 53%) of the title compound.

$^1$H-NMR(270 MHz, CD$_3$OD): δ 7.29(2H, d, J=9 Hz, Ar—H), 7.08(2H, d, J=8 Hz, Ar—H), 6.78(2H, d, J=9 Hz, Ar—H), 6.73(1H, d, J=8 Hz, Ar—H), 6.62(2H, d, J=8 Hz, Ar—H), 6.40(1H, t, J=2 Hz, 8-H), 6.30(1H, dd, J=8, 2 Hz, 6-H), 4.40(1H, s, 4-H), 3.95(2H, t, J=7 Hz, ArOCH$_2$CH$_2$), 3.31(2H, s, OH×2), 3.12(2H, s, 2-H), 2.50–2.30(6H, m, NCH$_2$×3), 1.85–1.35(10H, m, alkyl-H), 1.11(3H, s, 3-CH$_3$).

EXAMPLE 70

Synthesis of (3RS,4RS)-7-hydroxy-3-(4-hydroxyphenyl)-3-methyl-4-[4-(4-piperidinobutyloxy)phenyl]thiochroman hydrochloride

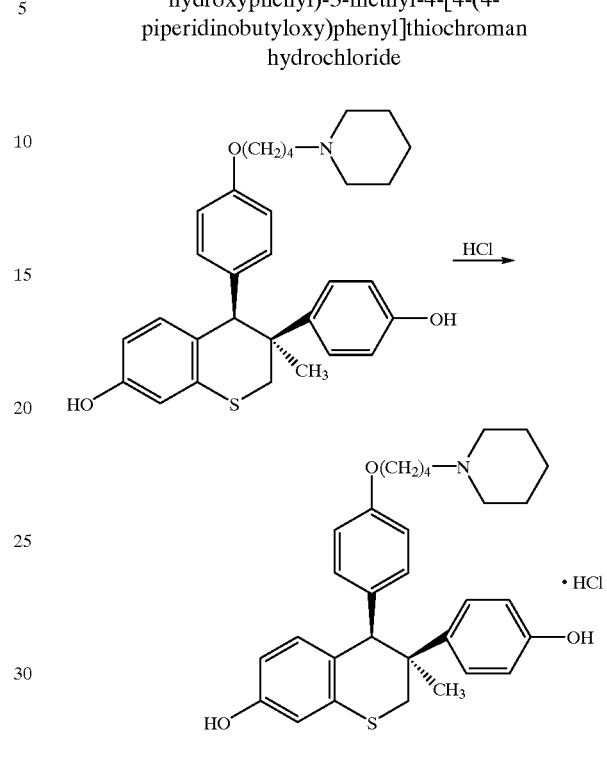

To methanol solution (3 ml) of (3RS,4RS)-7-hydroxy-3-(4-hydroxyphenyl)-3-methyl-4-[4-(4-piperidinobutyloxy)phenyl]thiochroman (18 mg, 0.093 mmol) was added aqueous 20% HCl solution (0.3 ml) and the resulting mixture was stirred for 20 hours. The reaction solution was distilled under reduced pressure to remove the solvent and the crude product thus produced was dissolved in methanol. To the resulting solution was added Dowex 1-×8 (240 mg) and the mixture was stirred for 30 minutes. Dowex 1-×8 was filtered off and the filtrate was then distilled under reduced pressure to remove the solvent. To the residue were added toluene (0.5 ml), methanol (0.5 ml) and 35% HCl (0.5 ml) and the mixture was distilled under reduced pressure to obtain 17 mg (yield: 96%) of the title compound.

$^1$H-NMR(270 MHz, CD$_3$OD): δ 7.30(2H, d, J=9 Hz, Ar—H), 7.11(2H, d, J=8 Hz, Ar—H), 6.81(2H, d, J=9 Hz, Ar—H), 6.73(1H, d, J=8 Hz, Ar—H), 6.63(2H, d, J=8 Hz, Ar—H), 6.40(1H, t, J=2 Hz, 8-H), 6.29(1H, dd, J=8, 2 Hz, 6-H), 6.42(1H, s, 4-H), 4.01(2H, t, J=7 Hz, ArOC<u>H</u>$_2$CH$_2$), 3.60–3.40(2H, m, NCH$_2$), 3.12(4H, brs, NCH$_2$×2), 2.00–1.70(10H, m, alkyl-H), 1.11(3H, s, 3-CH$_3$).

EXAMPLE 71

Synthesis of 1-(4,4,5,5,5-pentafluoropentyl)piperazine

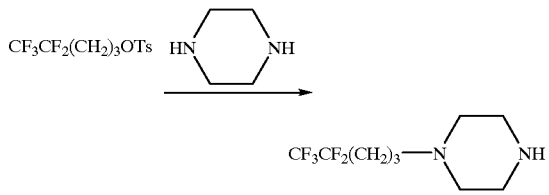

Piperazine (777 mg, 9.0 mmol) was added to ethanol solution (10 ml) of 4,4,5,5,5-pentafluoropentyloxytoluenesulfonate (600 mg, 1.81 mmol) and then heated under refluxing for 40 hours. After adding water, the reaction solution was extracted with ethyl acetate. The solvent was distilled off under reduced pressure from the extract to obtain 315 mg (yield: 100%) of the title compound.

$^1$H-NMR(CDCl$_3$): δ 2.89(4H, t, J=5 Hz, C$\underline{H}_2$NH×2), 2.38(6H, m, NCH$_2$×3), 2.20–1.95(2H, m, CF$_2$CH$_2$), 1.83–1.70(2H, m, CF$_2$CH$_2$C$\underline{H}_2$).

EXAMPLE 72

Synthesis of (3RS,4RS)-4-[4-(2-chloroethyloxy)phenyl]-7-methoxymethyloxy-3-[4-(methoxymethyloxy)phenyl]-3-methylthiochroman

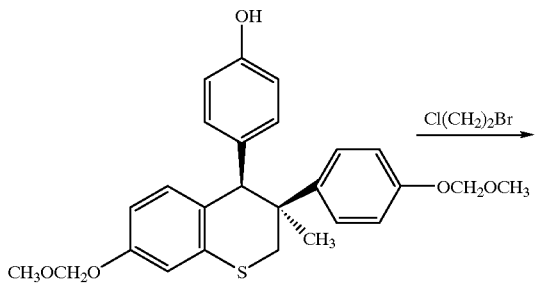

To methyl ethyl ketone solution (3 ml) of (3RS,4RS)-4-(4-hydroxyphenyl)-7-methoxymethyloxy-3-[4-(methoxymethyloxy)phenyl]-3-methyl-thiochroman (126 mg, 0.28 mmol) were added potassium carbonate (96 mg, 0.70 mmol) and 1-bromo-2-chloroethane (115 ml, 1.38 mmol), and the mixture was heated under refluxing for 70 hours. After adding water, the reaction solution was extracted with ethyl acetate. The extract was distilled under reduced pressure to remove the solvent and the crude product thus obtained was then purified using silica gel plate (ethyl acetate:hexane=1:2) to obtain 69 mg (yield: 48%) of the title compound.

$^1$H-NMR(270 MHz, CDCl$_3$): δ 7.34, 6.90(4H, AA'BB', J=9 Hz, Ar—H), 7.08, 6.81(4H, AA'BB', J=9 Hz, Ar—H), 6.89(1H, d, J=8 Hz, 5-H), 6.71(1H, d, J=3 Hz, 8-H), 6.55(1H, dd, J=8, 3 Hz, 6-H), 5.12(2H, s, OC$\underline{H}_2$OCH$_3$), 5.05(2H, d, J=1 Hz, OC$\underline{H}_2$OCH$_3$), 4.42(1H, s, 4-H), 4.19(2H, t, J=6 Hz, ArOC$\underline{H}_2$), 3.79(2H, t, J=6 Hz, ClCH$_2$), 3.45, 3.43(each 3H, each s, OCH$_3$×2), 3.20(1H, d, J=13 Hz, 2-H), 3.09(1H, d, J=13 Hz, 2-H), 1.15(3H, s, 3-CH$_3$).

EXAMPLE 73

Synthesis of (3RS,4RS)-7-methoxymethyloxy-3-[4-(methoxymethyloxy)phenyl]-3-methyl-4-{4-[2-(4-(4,4,5,5,5-pentafluoropentyl)piperazino)ethyloxy]phenyl}thiochroman

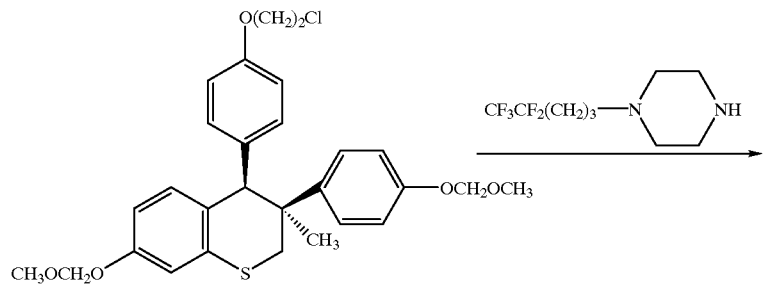

-continued

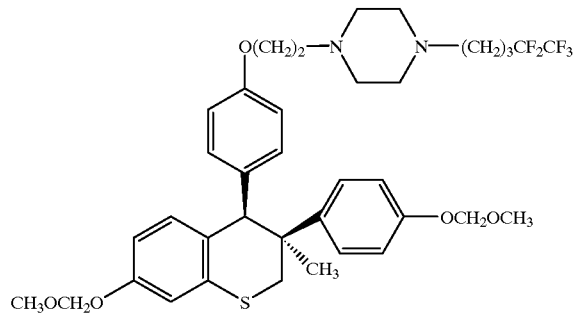

Under argon atmosphere 4-(4,4,5,5,5-pentafluoropentyl)piperazine (70 mg, 0.4 mmol) was added to dimethylformamide solution (0.5 ml) of (3RS,4RS)-4-[4-(2-chloroethyloxy)phenyl]-7-methoxymethyloxy-3-[4-(methoxymethyloxy)phenyl]-3-methyl-thiochroman (69 mg, 0.13 mmol) and then stirred for 8 hours at 80° C. After adding water, the reaction solution was extracted with ethyl acetate. The extract was distilled under reduced pressure to remove the solvent and the crude product thus obtained was then purified using amino silica gel plate (ethyl acetate:hexane=1:2) to obtain 67 mg (yield: 77%) of the title compound.

$^1$H-NMR(270 MHz, CDCl$_3$): δ 7.33, 6.90(4H, AA'BB', J=9 Hz, Ar—H), 7.05, 6.79(4H, AA'BB', J=9 Hz, Ar—H), 6.86(1H, d, J=8 Hz, 5-H), 6.70(1H, d, J=3 Hz, 8-H), 6.55 (1H, dd, J=8, 3 Hz, 6-H), 5.11(2H, s, OCH$_2$OCH$_3$), 5.05(2H, d, J=1 Hz, OCH$_2$OCH$_3$), 4.41(1H, s, 4-H), 4.06(2H, t, J=6 Hz, ArOCH$_2$), 3.45, 3.42(each 3H, each s, OCH$_3$×2), 3.22 (1H, d, J=13 Hz, 2-H), 3.09(1H, d, J=13 Hz, 2-H), 2.80(2H, t, J=6 Hz, OCH$_2$OCH$_2$), 2.60, 2.59(each 4H, each brs, NCH$_2$CH$_2$N×2), 2.40(2H, t, J=7 Hz, NCH$_2$), 2.20–1.95(2H, m, CF$_2$CH$_2$), 1.85–1.70(2H, m, CF$_2$CH$_2$CH$_2$), 1.15(3H, s, 3-CH$_3$).

EXAMPLE 74

Synthesis of (3RS,4RS)-7-hydroxy-3-(4-hydroxyphenyl)-3-methyl-4-}4-[2-(4-(4,4,5,5,5-pentafluoropentyl)piperazino)ethyloxy]phenyl}thiochroman dihydrochloride

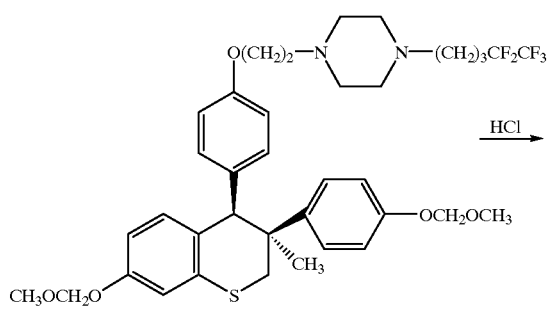

-continued

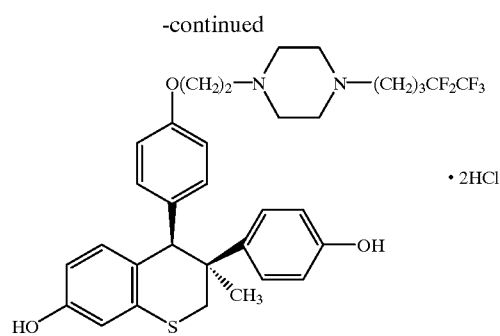

To methanol solution (1 ml) of (3RS,4RS)-7-methoxymethyloxy-3-[4-(methoxymethyloxy)phenyl]-3-methyl-4-{4-[2-(4-(4,4,5,5,5-pentafluoropentyl)piperazino)ethyloxy]phenyl}thiochroman (67 mg, 0.10 mmol) was added aqueous 20% HCl solution (0.5 ml) and the resulting mixture was then stirred for 20 hours at room temperature. The solvent was distilled off under reduced pressure to obtain the crude product which was then purified using amino silica gel plate (ethyl acetate:methanol=10:1). After adding aqueous 20% HCl solution to the product, the solvent was distilled off under reduced pressure to obtain 62 mg (yield: 85%) of the title compound.

$^1$H-NMR(270 MHz, CD$_3$OD): δ 7.30, 6.93(4H, AA'BB', J=9 Hz, Ar—H), 7.09, 6.62(4H, AA'BB', J=9 Hz, Ar—H), 6.72(1H, d, J=9 Hz, 5-H), 6.40(1H, d, J=3 Hz, 8-H), 6.30 (1H, dd, J=8.2 Hz, 6-H), 4.46(1H, s, 4-H), 4.39(2H, brs, ArOCH$_2$CH$_2$), 3.90–3.60(10H, d, NCH$_2$×5), 3.31(2H, m, NCH$_2$), 3.12(2H, ABq, J=13 Hz, 2-H), 2.40–2.00(4H, m, CF$_2$CH$_2$), 1.12(3H, s, 3-CH$_3$).

EXAMPLE 75

Synthesis of (3RS,4RS)-7-hydroxy-3-(4-hydroxyphenyl)-3-methyl-4-[8-(4,4,5,5,5-pentafluoropentylsulfinyl)octyl]thiochroman

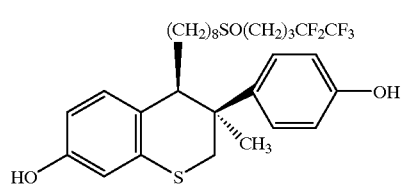

The title compound was prepared from 7-methoxy-3-(4-methoxyphenyl)-3-methylthiochroman-4-one and 8-t-butyldimethylsilyloxyoctyne according to the same method as Examples 25 to 34.

¹H-NMR(270 MHz, CDCl₃) δ 7.22(d, J=8.6 Hz, 2H, Ar—H), 6.86(d, J=8.3 Hz, 3H, Ar—H and C5-H), 6.67(d, J=2.3 Hz, 1H, C8-H), 6.50(dd, J=2.3 Hz and 8.3 Hz, 1H, C6-H), 3.65(d, J=11.6 Hz, 1H, C2-H), 2.94(d, J=11.6 Hz, 1H, C2-H), 2.90–2.50(m, 5H, 2×CH₂S(O) and C4-H), 2.40–2.10(m, 4H, CH₂CH₂CF₂CF₃), 1.66(m, 2H, alkyl-H), 1.21(s, 3H, C3-CH₃), 1.45–0.90(m, 12H, alkyl-H).

EXAMPLE 76

Synthesis of (3RS,4RS)-7-hydroxy-3-(4-hydroxyphenyl)-3-methyl-4-[10-(4,4,5,5,5-pentafluoropentylsulfinyl)decyl]thiochroman

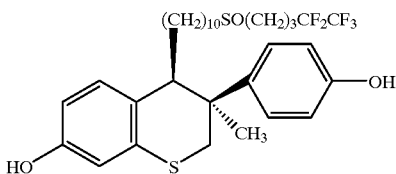

The title compound was prepared from 7-methoxy-3(4-methoxyphenyl)-3-methylthiochroman-4-one and 10-t-butyldimethylsilyloxydecyne according to the same method as Examples 25 to 34.

¹H-NMR(270 MHz, CDCl₃): δ 7.21(d, J=8.6 Hz, 2H, Ar—H), 6.86(m, 3H, Ar—H and C5-H), 6.69(s, 1H, C8-H), 6.51(d, J-6.9 Hz, 1H, C6-H), 3.63(d, J-1.2 Hz, 1H, C2-H), 2.94(d, J=11.2 Hz, 1H, C2-H), 2.90–2.60(m, 5H, 2×CH₂S(O) and C4-H), 2.40–2.10(m, 4H, CH₂CH₂CF₂CF₃), 1.90–1.70(m, 2H, alkyl-H), 1.17(s, 3H, C3-CH₃), 1.50–0.90 (m, 16H, alkyl-H).

EXAMPLE 77

Synthesis of (3RS,4RS)-7-hydroxy-3-phenyl-3-methyl-4-[9-(4,4,5,5,5-pentafluoropentylsulfinyl)nonyl]thiochroman

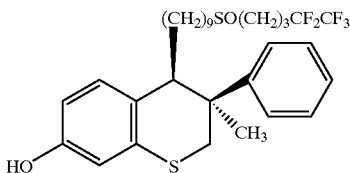

The title compound was prepared from 7-methoxy-3-phenyl-3-methylthiochroman-4-one and 9-t-butyldimethylsilyloxynonyne according to the same method as Examples 25 to 34.

¹H-NMR(270 MHz, CDCl₃) δ 7.39–7.33(m, 5H, Ar—H), 6.89(d, J=7.9 Hz, 1H, C5-H), 6.69(s, 1H, C8-H), 6.58–6.48 (m, 2H, C6-H and ArOH), 3.68(d, J=11.5 Hz, 1H, C2-H), 3.01(d, J=11.5 Hz, 1H, C2-H), 2.90–2.60(m, 5H, 2×CH₂S(O) and C4-H), 2.40–2.10(m, 4H, CH₂CH₂CF₂CF₃), 1.67(m, 2H, alkyl-H), 1.26(s, 3H, C3-CH₃), 1.50–0.90(m, 14H, alkyl-H).

EXAMPLE 78

Synthesis of (3RS,4RS)-3-(4-hydroxyphenyl)-3-methyl-4-[9-(4,4,5,5,5 pentafluoropentylsulfinyl)nonyl]thiochroman

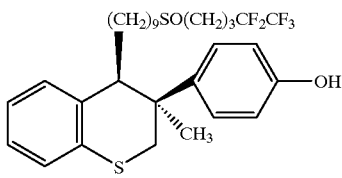

The title compound was prepared from 3-(4-methoxyphenyl)-3-methylthiochroman-4-one and 9-t-butyldimethylsilyloxynonyne according to the same method as Examples 25 to 34.

¹H-NMR(270 MHz, CDCl₃): δ 7.24–6.81(m, 8H, Ar—H), 3.67(m, 1H, C2-H), 2.97(m, 1H, C2-H), 2.82–2.63 (m, 5H, 2×CH₂S(O) and C4-H), 2.40–2.10(m, 4H, CH₂CH₂CF₂CF₃), 1.78(m, 2H, alkyl-H), 1.40–0.80(m, 17H, alkyl-H and C3-CH₃).

EXAMPLE 79

Synthesis of 7-methoxy-3-(4-methoxyphenyl)-3-methyl-4-(9-pentylthiononyl)thiochroman

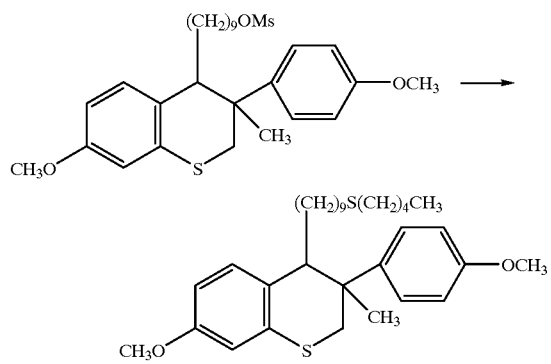

To a solution of pentylthioacetate (430 mg, 2.94 mmol) in methanol (10 ml) was added dropwise 1M solution of sodium methanolate (2.5 ml, 2.52 mmol) at room temperature and stirred for one hour. A solution of 7-methoxy-3-(4-methoxyphenyl)-3-methyl-4-(9-methanesulfonyloxynonyl) thiochroman (204 mg, 0.391 mmol) in tetrahydrofuran (5 ml) was added dropwise to the reaction mixture at the same temperature and stirred for overnight. The reaction mixture was quenched with water and then diluted with ethyl acetate. The organic layer was separated, washed with saturated NaCl solution, dried over magnesium sulfate, filtered and then concentrated. The concentrate was subjected to flash silica gel chromatography (hexane:ethyl acetate=9:1) to obtain 230 mg (yield: 95%, 3RS,4RS/3RS,4SR=9:1) of the title compound as a yellow oil.

¹H-NMR(270 MHz, CDCl₃): δ 7.29(d, J=8.9 Hz, 2H, Ar—H), 6.91(m, 3H, Ar—H), 6.79(d, J=2.6 Hz, 1H, C8-H), 6.58(dd, J=8.2 Hz and 2.6 Hz, 1H, Ar—H), 3.82(s, 3H, OCH₃), 3.78(s, 3H, OCH₃), 3.64(d, J=1 1.2 Hz, 1H, C2-H), 2.98(d, J=11.6 Hz, 1H, C2-H), 2.74(brt, 1H, C4-H), 2.47(m, 4H, 2×SCH₂), 1.55–0.89(m, 28H, C3-CH₃ and alkyl-H).

EXAMPLE 80

Synthesis of (3RS,4RS)-7-hydroxy-3-(4-hydroxyphenyl)-3-methyl-4-(9-pentylthiononyl)thiochroman

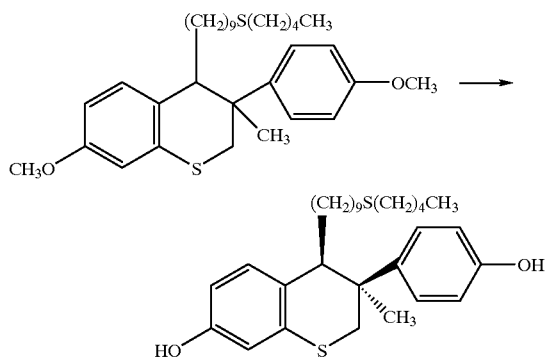

To a solution of 7-methoxy-3-(4-methoxyphenyl)-3-methyl-4-(9-pentylthiononyl)thiochroman (230 mg, 0.435 mmol) in dry dichloromethane (20 ml) was added dropwise 1M solution of boron tribromide in dichloromethane (3.04 ml, 3.04 mmol) at −78° C. and stirred at the same temperature for one hour. Then the reaction mixture was warmed to room temperature and stirring was continued for additional 10 hours. The reaction mixture was quenched with water and then diluted with ethyl acetate. The organic layer was washed with saturated sodium hydrogen sulfide solution and water, dried over magnesium sulfate, filtered and evaporated. The concentrate was subjected to flash silica gel chromatography (hexane:ethyl acetate=9:1) to obtain 178 mg (yield: 82%) of the title compound as a colorless oil.

$^1$H-NMR(270 MHz, CDCl$_3$): δ 7.23(d, J=8.6 Hz, 2H, Ar—H), 6.84(dd, J=8.3 Hz and 8.5 Hz, 3H, Ar—H), 6.67(d, J=2.6 Hz, 1H, C8-H), 6.50(dd, J=8.3Hz and 2.3 Hz, 1H, Ar—H), 5.12(brs, 1H, OH), 4.83(brs, 1H, OH), 3.62(d, J=11.5 Hz, 1H, C2-H), 2.95(d, J=11.5 Hz, 1H, C2-H), 2.68(brt, 1H, C4-H), 2.49(m, 4H, 2×SCH$_2$), 1.58–0.89(m, 28H, C3-CH$_3$ and alkyl-H).

EXAMPLE 81

Synthesis of (3RS,4RS)-7-hydroxy-3-(4-hydroxyphenyl)-3-methyl-4-(9-pentylsulfinylnonyl)thiochroman

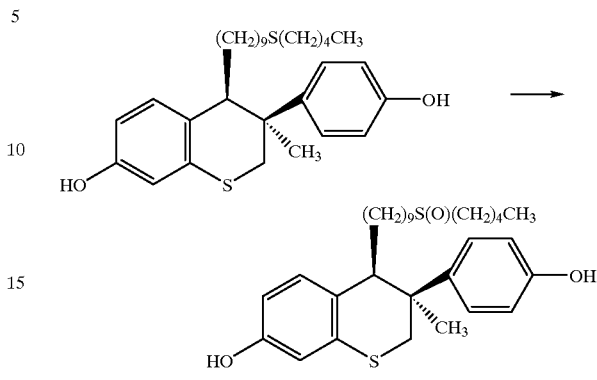

A solution of (3RS,4RS)-7-hydroxy-3-(4-hydroxyphenyl)-3-methyl-4-(9-pentylthiononyl)thiochroman (178 mg, 0.355 mmol) and sodium periodate (83 mg, 0.390 mmol) in methanol (20 ml) and water (5 ml) was stirred at room temperature for 3.5 hours. The reaction mixture was quenched with water and then diluted with ethyl acetate. The organic layer was washed with water, dried over magnesium sulfate, filtered and concentrated. The concentrate was purified with preparative chromatography on silica gel plate (hexane:ethyl acetate=1:1) to obtain 101 mg (yield: 55%) of the title compound as a colorless oil.

$^1$H-NMR(270 MHz, CDCl$_3$): δ 7.24(m, 3H, Ar—H), 6.86(dd, J=8.4 Hz and 2.4 Hz, 2H, Ar—H), 6.66(d, J=2.3 Hz, 1H, C8-H), 6.51(m, 1H, Ar—H), 5.67(s, 1H, OH), 5.43(s, 1H, OH), 3.62(dd, J=11.5 Hz and 3.9 Hz, 1H, C2-H), 2.76(m, 5H, C2-H and 2×S(O)CH$_2$), 1.71(m, 3H, alkyl-H), 1.42–0.90(m, 25H, C3-CH3 and alkyl-H).

EXAMPLE 82

Optical resolution of rac-(3RS,4RS)-7-hydroxy-3-(4-hydroxyphenyl)-3-methyl-4-[9-(4,4,5,5,5-pentafluoropentylthio)nonyl]thiochroman and synthesis of its sulfinyl derivative

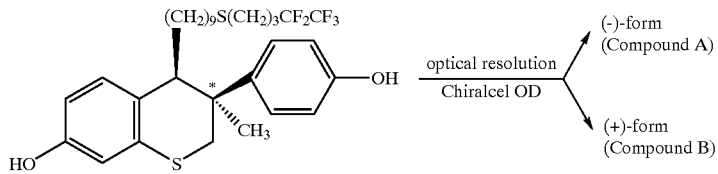

The racemate of (3RS,4RS)-7-hydroxy-3-(4-hydroxyphenyl)-3-methyl-4-[9-(4,4,5,5,5-pentafluoropentylthio)nonyl]thiochroman (205 mg) was separated by preparative HPLC using a Chiralcel OD (2×25 cm, available from Daicel Chemical Industries, LTD) and a UV detector at 280 nm. The eluent was a (85:12:3:0.2) mixture of n-hexane/isopropanol/methanol/trifluoroacetic acid at flow rate of 9.0 ml/min. The first eluted peak was, after evaporation of the solvent, the (−)-compound (Compound A, retention time: 19.0 min., 78.9 mg, 84.3% ee) and the second was the (+)-compound (Compound B, retention time: 21.2 min., 64.9 mg, 84.4% ee). Additionally the obtained (−) and (+)-compounds were purified by preparative HPLC under the same condition as in the first separation to give 47.6 mg of Compound A [95.8% ee, $[a]_D=-18.39$ (c=1.000, $CHCl_3$)] and 34.5 mg of Compound B [96.8% ee, $[a]_D=+16.80$ (c=1.000, $CHCl_3$)], respectively.

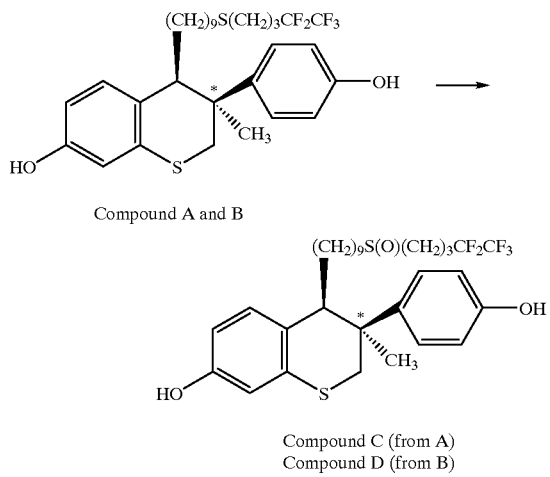

Compound A and B

Compound C (from A)
Compound D (from B)

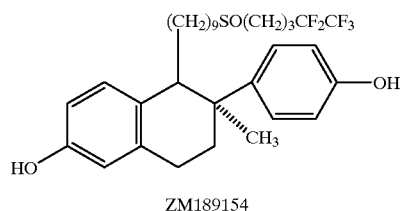

ZM189154

MCF-7 cell lines (ATCC) were incubated in MEM (minimum essential medium) medium which is supplemented by 3% DCC (dextran coated charcoal)-treated FBS (fetal bovine serum) but does not contain phenol red, for one week. One day before drug administration, incubated MCF-7 cells were plated in 96-well plate in the concentration of $5 \times 10^3$ cells per well. After the 96-well plate was incubated for one day, 0.1 nM of estradiol and the test compound in the given concentration were added to each well. The plate was incubated for 7 days at 37° C. and then MTT solution (Sigma) was added to each well in the amount of 15 μl and allowed to react for 2 hours at 37° C. After the reaction is completed, the solubilizing/stopping solution (constitution: SDS, acetic acid, N,N-dimethylformamide) was added to each well in the amount of 100 μl. Then, the absorption for each well at 570 nm was measured by means of a plate reader. $IC_{50}$ value for inhibiting cell growth of 50% was calculated from the results as measured and described in the following Table 1.

TABLE 1

| Test compound | $IC_{50}$ value of the test compounds (nM) | | | | |
| --- | --- | --- | --- | --- | --- |
| | Compound of Example 6 | Compound of Example 7 | Compound of Example 12 | Compound of Example 46 | ZM189154 |
| $IC_{50}$ (nM) | 277 | 54.8 | 524 | 33 | 77 |

The obtained optically active Compounds A and B were oxidized to the corresponding sulfinyl Compound C (18.8 mg, yield: 38% from 47.8 mg of Compound A) and Compound D (9.8 mg, yield: 29% from 34.5 mg of Compound B) in a similar manner to Example 34.

Experiment 1: Cell Growth Inhibiting Activity

In this experiment, the cell growth inhibiting activity was determined by using the compounds of Examples 6, 7, 12 and 46 as the test compound and the known anti-estrogenic compound ZM189154 having the following structure (see, EP0124369 B1) as the control compound, according to the method described hereinafter.

From the results described in the above Table 1, it could be seen that the compound of the present invention exhibits cell growth inhibiting activity comparable to that of ZM189154 which has been known as anti-estrogenic compound in the prior art.

Experiment 2: Anti-Estrogenic Activity (Subcutaneous Administration)

Anti-estrogenic activity of the test compound by subcutaneous administration was determined according to the method described hereinafter. In this experiment, the compounds of Examples 6, 7, 12 and 46 were used as the test compound and the known anti-estrogenic compound ZM189154 was used as the control compound as in Experiment 1.

The anti-estrogenic activity was determined by subcutaneously injecting 17 β-estradiol-benzoate (Sigma) to mice (ICR, weight 30±2 g), which were ovariectomized two weeks before, in an amount of 0.1 μg/day, per mouse for 3 days and then measuring the degree that the test compound inhibits the increase of uterine weight. In this experiment, the test compound or the control compound was dissolved in peanut oil (Sigma) and injected subcutaneously for 3 days, once a day. After 24 hours from the last injection, the test animal was sacrificed and uterus was removed and weighed. The results as measured are described in the following Table 2.

TABLE 2

Anti-estrogenic activity of the test compound in ovariectomized mice which were administered with 17 β-estradiol

| Test compound/dosage (s.c., 3 days) | | Inhibition (%) |
|---|---|---|
| Compound of Example 6 | 30 μg/mouse | 83.1 |
| Compound of Example 7 | 30 μg/mouse | 87.0 |
| Compound of Example 12 | 30 μg/mouse | 74.8 |
| Compound of Example 46 | 30 μg/mouse | 16.7 |
| Control compound ZM189154 | 30 μg/mouse | 73.8 |

From the results described in the above Table 2, it could be seen that the compounds of Examples 6, 7, 12 and 46 according to the present invention substantially inhibit the increase of uterine weight by estradiol to the degree rather superior to that of ZM189154 which has been known as anti-estrdgenic compound in the prior art.

Experiment 3: Anti-Estrogenic Activity (Oral Administration)

Oral anti-estrogenic activity of the test compound was determined according to the method described hereinafter. In this experiment, the compound of Example 7 was used as the test compound and the known anti-estrogenic compound ZM189154 was used as the control compound as in Experiment 2.

Anti-estrogenic activity was determined by subcutaneous administration of 17-estradiol-benzoate (Sigma) to mice (ICR, weight 30±2 g), which were ovariectomized 2 weeks before, in the amount of 0.1 μg/day, per mouse for 3 days and then measuring the degree that the test compound inhibits the increase in uterus weight by stimulus with estradiol. In this experiment, the test compound or the control compound was suspended in 5% arabic gum solution and orally administered for 3 days, once a day. After 24 hours from the last administration, the test animal was sacrificed and uterus was removed and weighed. The results as measured are described in the following Table 3.

TABLE 3

Anti-estrogenic activity of the test compound in ovariectomized mice which were administered with 17 β-estradiol (oral administration, 3 days)

| Test compound/dosage (p.o., 3 days) | | Inhibition (%) |
|---|---|---|
| Compound of Example 7 | 10 mg/kg | 68.1 |
| ZM189154 | 10 mg/kg | 41.7 |

From the results described in the above Table 3, it could be seen that the compound according to the present invention administered via oral route substantially inhibits the increase of uterine weight by estradiol to the degree superior to that of ZM189154 which has been known as anti-estrogenic active compound in the prior art.

Experiment 4: Effect on Bone Mineral Density of Mouse Femur

The effect of the compound of the present invention on bone mineral density of mouse femur was determined according to the method described hereinafter. In this experiment, the compounds of Example 7 was used as the test compound and the known anti-estrogenic compound ZM189154 was used as the control compound as in Experiment 2.

MCF-7 cells (ATCC) as human breast cancer cell were transplanted subcutaneously into BALB/c nude mouse (female, 6 weeks) and then estradiol was percutaneously injected twice a week in an amount of 0.01 mg/mouse, for 3 weeks. Thereafter, estradiol was administered once a week in the same amount and the test compound or the control compound dissolved in 10% ethanol-90% peanut oil was administered. The control group received only vehicle. The test or control compound was administered subcutaneously in an amount of 1 mg/0.1 mg/mouse, once a week. After the administration of the test compound for 6 weeks, left femur was excised and soft tissue was removed therefrom. Then the bone mineral density (BMD) was measured in a SPA mode by means of dual energy X-ray absorptiometry DCS-600 (Aloka). For interpretation, femur was divided into ten in the direction of long axis and the mean bone marrow densities of 3, 4 and 3 fragments from proximal position were calculated. Each of the fragments was represented as proximal, middle or distal, respectively. The result as measured is described in the following Table 4.

TABLE 4

Effect of the compound of the present invention on bone mineral density of mouse femur

| | proximal BMD[a] | distal BMD | whole BMD |
|---|---|---|---|
| Control group | 35.95 ± 1.50[b] | 37.80 ± 1.75 | 35.63 ± 0.97 |
| Compound of Example 7 | 35.05 ± 2.05 | 36.29 ± 1.46 | 37.23 ± 1.41 |
| ZM189154 | 34.19 ± 2.19 | 32.80 ± 1.30 | 34.57 ± 1.40 |

*[a]mg/cm$^2$, [b]mean ± SE

It is generally agreed that we focus on proximal and distal portion for elucidating the effect of anti-estrogen on bone metabolism. As can be seen from the results described in the above Table 4, the compound according to the present invention did little affect bone mineral density (BMD) at both proximal and distal portion and increased whole BMD by 4.5% when compared to control. In contrast, ZM189154 decreased BMD by 4.9%, 13.3% and 3.0% at proximal, distal and whole femur, respectively. There was no difference in inhibition of MCF-7 tumor growth between the test compound and ZM189154. Therefore, it could be identified that the compound of the present invention has little affect on BMD different from ZM189154 which has been known as anti-estrogenic active compound in the prior art.

What is claimed is:

1. A benzopyran derivative represented by formula (I):

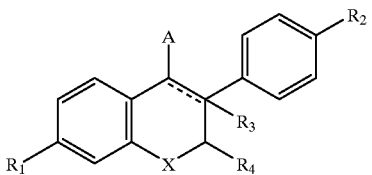

(I)

and pharmaceutically acceptable salt thereof, in which
----- represents a single bond or a double bond;
$R_1$ and $R_2$ independently of one another represent hydrogen, hydroxy or OR group, wherein R represents acyl or alkyl;
$R_3$ represents hydrogen, lower alkyl or halogeno lower alkyl, provided that when ----- represents a double bond, $R_3$ is not present;
$R_4$ represents hydrogen or lower alkyl;
A represents a group of formula (a), (b), (c) or (d);

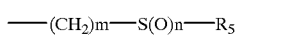 (a)

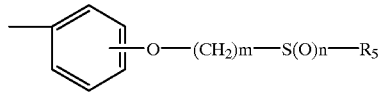 (b)

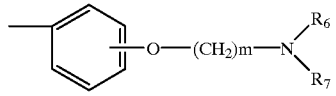 (c)

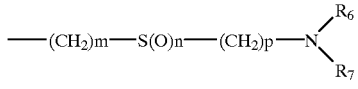 (d)

$R_5$, $R_6$ and $R_7$ independently of one another represent hydrogen, alkyl, halogenoalkyl, alkenyl or halogenoalkenyl, or
$R_6$ and $R_7$ together with nitrogen atom to which they are bound can form a 4- to 8-membered heterocyclic ring which can be substituted with $R_5$;
X represents O, S or $NR_8$, wherein $R_8$ represents hydrogen or lower alkyl;
m denotes an integer of 2 to 15;
n denotes an integer of 0 to 2; and
p denotes an integer of 0 to 4.

2. The benzopyran derivative of formula (I) as defined in claim 1, wherein ----- represents a single bond or a double bond; $R_1$ and $R_2$ independently of one another represent hydrogen, hydroxy or OR wherein R represents alkyl; $R_3$ represents hydrogen, $C_1$–$C_4$ lower alkyl or halogeno-$C_1$–$C_4$ lower alkyl, provided that when ----- represents a double bond, $R_3$ is not present; $R_4$ represents hydrogen or $C_1$–$C_4$ lower alkyl; A represents a group of formula (a), (b), (c) or (d); $R_5$, $R_6$ and $R_7$ independently of one another represent hydrogen, $C_1$–$C_6$ alkyl, halogeno-$C_1$–$C_6$ alkyl, $C_2$–$C_6$ alkenyl or halogeno-$C_2$–$C_6$ alkenyl, or $R_6$ and $R_7$ together with nitrogen atom to which they are bound can form a 5- to 6-membered heterocyclic ring which can contain 1 to 2 nitrogen atoms and can be substituted with halogeno-$C_1$–$C_6$ alkyl; X represents O, S or $NR_8$, wherein $R_8$ represents hydrogen or $C_1$–$C_4$ lower alkyl; m denotes an integer of 4 to 12; n denotes an integer of 0 to 2 and p denotes an integer of 1 to 3.

3. The benzopyran derivative of formula (I) as defined in claim 2, wherein ----- represents a single bond or a double bond; $R_1$ and $R_2$ independently of one another represent hydrogen or hydroxy; $R_3$ represents hydrogen or $C_1$–$C_2$ lower alkyl, provided that when ----- represents a double bond, $R_3$ is not present; $R_4$ represents hydrogen or $C_1$–$C_2$ lower alkyl; A represents a group of formula (a), (b), (c) or (d); $R_5$, $R_5$ and $R_7$ independently of one another represents hydrogen, $C_1$–$C_6$ alkyl or halogeno-$C_1$–$C_6$ alkyl, or $R_6$ and $R_7$ together with nitrogen atom to which they are bound can form piperazinyl or piperidino group which can be substituted with halogeno-$C_1$–$C_6$ alkyl; X represents O or S; m denotes an integer of 4 to 12; n denotes an integer of 0 to 2 and p denotes an integer of 2.

4. The benzopyran derivative of formula (I) as defined in claim 3, wherein X represents S.

5. The benzopyran derivative of formula (I) as defined in claim 1, which is selected from the group consisting of:
(3RS,4RS)-7-hydroxy-3-(4-hydroxyphenyl)-3-methyl-4-[9-(4,4,5,5,5-pentafluoropentylthio)nonyl]-2,3-dihydro-4H-benzopyran;
(3RS,4RS)-7-hydroxy-3-(4-hydroxyphenyl)-3-methyl-4-[9-(4,4,5,5,5-pentafluoropentylsulfinyl)nonyl]-2,3-dihydro-4H-benzopyran;
(3RS,4RS)-7-hydroxy-3-(4-hydroxyphenyl)-3-methyl-4-[8-(4,4,5,5,5-pentafluoropentylthio)octyl]-2,3-dihydro-4H-benzopyran;
(3RS,4RS)-7-hydroxy-3-(4-hydroxyphenyl)-3-methyl-4-[8-(4,4,5,5,5-pentafluoropentylsulfinyl)octyl]-2,3-dihydro-4H-benzopyran;
(3RS,4RS)-7-hydroxy-3-(4-hydroxyphenyl)-3-methyl-4-[9-(4,4,5,5,5-pentafluoropentylsulfonyl)nonyl]-2,3-dihydro-4H-benzopyran;
7-hydroxy-3-(4-hydroxyphenyl)-4-[4-(5-(4,4,5,5,5-pentafluoropentylthio)pentyloxy)phenyl]-2H-benzopyran;
(3RS,4RS)-7-hydroxy-3-(4-hydroxyphenyl)-3-methyl-4-[9-(4,4,5,5,5-pentafluoropentylsulfinyl)nonyl]-thiochroman;
(3RS,4RS)-7-hydroxy-3-(4-hydroxyphenyl)-3-methyl-4-[3-(4-(4,4,5,5,5-pentafluoropentylthio)butyloxy)phenyl]-2,3-dihydro-4H-benzopyran;
(3RS,4RS)-7-hydroxy-3-(4-hydroxyphenyl)-3-methyl-4-[3-(4-(4,4,5,5,5-pentafluoropentylsulfinyl)butyloxy)phenyl]-2,3-dihydro-4H-benzopyran;
(3RS,4RS)-7-hydroxy-3-(4-hydroxyphenyl)-3-methyl-4-[3-(4-(4,4,5,5,5-pentafluoropentylsulfonyl)butyloxy)phenyl]-2,3-dihydro-4H-benzopyran;
(3RS,4RS)-7-hydroxy-3-(4-hydroxyphenyl)-3-methyl-4-[9-(2-piperidinoethylthio)-nonyl]-2,3-dihydro-4H-benzopyran;
(3RS,4RS)-7-hydroxy-3-(4-hydroxyphenyl)-3-methyl-4-[9-(2-piperidinoethylsulfinyl)nonyl]-2,3-dihydro-4H-benzopyran;
(3RS,4RS)-7-hydroxy-3-(4-hydroxyphenyl)-3-methyl-4-[3-(5-(4,4,5,5,5-pentafluoropentylthio)pentyloxy)phenyl]-2,3-dihydro-4H-benzopyran;
(3RS,4RS)-7-hydroxy-3-(4-hydroxyphenyl)-3-methyl-4-[3-(5-(4,4,5,5,5-pentafluoropentylsulfinyl)pentyloxy)phenyl]-2,3-dihydro-4H-benzopyran;

(3RS,4RS)-7-hydroxy-3-(4-hydroxyphenyl)-3-methyl-4-[3-(5-(4,4,5,5,5-pentafluoropentylsulfonyl)pentyloxy)phenyl]-2,3-dihydro-4H-benzopyran;
(3RS,4RS)-7-hydroxy-3-(4-hydroxyphenyl)-3-methyl-4-[4-(piperidinoethyloxy)phenyl]-2,3-dihydro-4H-benzopyran;
(3RS,4RS)-7-hydroxy-3-(4-hydroxyphenyl)-3-methyl-4-[4-(5-(4,4,5,5,5-pentafluoropentylsulfonyl)pentyloxy)phenyl]thiochroman;
(3RS,4RS)-7-hydroxy-3-(4-hydroxyphenyl)-3-methyl-4-[4-(4-piperidinobutyloxy)phenyl]thiochroman or its hydrochloride;
(3RS,4RS)-7-hydroxy-3-(4-hydroxyphenyl)-3-methyl-4-{4-[2-(4-(4,4,5,5,5-pentafluoropentyl)piperazino)ethyloxy]phenyl}thiochroman dihydrochloride;
(3RS,4RS)-7-hydroxy-3-(4-hydroxyphenyl)-3-methyl-4-[8-(4,4,5,5,5-pentafluoropentylsulfinyl)octyl]thiochroman;
(3RS,4RS)-7-hydroxy-3-(4-hydroxyphenyl)-3-methyl-4-[10-(4,4,5,5,5-pentafluoropentylsulfinyl)decyl]thiochroman;
(3RS,4RS)-7-hydroxy-3-phenyl-3-methyl-4-[9-(4,4,5,5,5-pentafluoropentylsulfinyl)nonyl]thiochroman;
(3RS,4RS)-3-(4-hydroxyphenyl)-3-methyl-4-[9-(4,4,5,5,5-pentafluoropentylsulfinyl)nonyl]thiochroman;
(3RS,4RS)-7-methoxy-3-(4-methoxyphenyl)-3-methyl-4-(9-pentylthiononyl)thiochroman;
(3RS,4RS)-7-hydroxy-3-(4-hydroxyphenyl)-3-methyl-4-(9-pentylthiononyl)thiochroman;
(3RS,4RS)-7-hydroxy-3-(4-hydroxyphenyl)-3-methyl-[4-(9-pentylsulfinynonyl)thiochroman;
(3RS,4RS)-7-hydroxy-3-(4-hydroxyphenyl)-3-methyl-4-[9-(4,4,5,5,5-pentafluoropentylthio)nonyl]thiochroman; and
(3RS,4RS)-7-hydroxy-3-(4-hydroxyphenyl)-3-methyl-4-[9-(4,4,5,5,5-pentafluoropentylsulfinyl)nonyl]thiochroman.

6. A process for preparing the compound of formula (I):

(I)

and salt thereof, in which

----- represents a single bond or a double bond;

$R_1$ and $R_2$ independently of one another represent hydrogen, hydroxy or OR group, wherein R represents acyl or alkyl;

$R_3$ represents hydrogen, lower alkyl or halogeno lower alkyl, provided that when ----- represents a double bond, $R_3$ is not present;

$R_4$ represents hydrogen or lower alkyl;

A represents a group of formula (a), (b), (c) or (d);

(a)
—(CH$_2$)m—S(O)n—R$_5$ (b)

—O—(CH$_2$)m—S(O)n—R$_5$ (c)

—O—(CH$_2$)m—N(R$_6$)(R$_7$)

(d)

—(CH$_2$)m—S(O)n—(CH$_2$)p—N(R$_6$)(R$_7$)

$R_5$, $R_6$ and $R_7$ independently of one another represent hydrogen, alkyl, halogenoalkyl, alkenyl or halogenoalkenyl, or $R_6$ and $R_7$ together with nitrogen atom to which they are bound can form a 4- to 8-membered heterocyclic ring which can be substituted with $R_5$;

X represents O, S or $NR_8$, wherein $R_8$ represents hydrogen or lower alkyl;

m denotes an integer of 2 to 15;

n denotes an integer of 0 to 2; and p denotes an integer of 0 to 4, characterized in that a compound of formula (VIII):

(VIII)

wherein $R_3$, $R_4$ and X are defined as above and P represents hydrogen or protected hydroxy group, is reacted with a compound of formula (IX):

Li—C≡C—(CH$_2$)qOTBS    (IX)

wherein q denotes an integer of m−2 and TBS means t-butyldimethylsilyl group, to produce a compound of formula (VII):

(VII)

wherein $R_3$, $R_4$, X, P, q and TBS are defined as above, the resulting compound of formula (VII) is reduced with sodium cyanoborohydride and zinc iodide to produce a compound of formula (VIA):

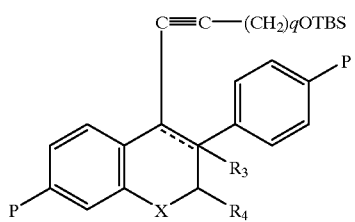
(VIA)

wherein ----, $R_3$, $R_4$, X, P, q and TBS are defined as above, the resulting compound of formula (VIA) is reduced with palladium on carbon (Pd/C) to produce a compound of formula (VIB):

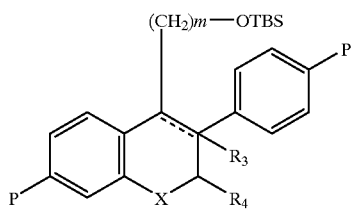
(VIB)

wherein ----, $R_3$, $R_4$, X, P, m and TBS are defined as above, the resulting compound of formula (VIB) is then treated with pyridinium p-toluenesulfonate to produce a compound of formula (VIC):

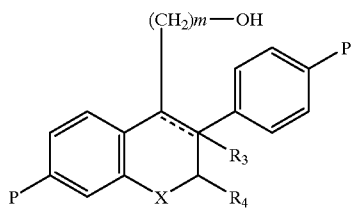
(VIC)

wherein ----, $R_3$, $R_4$, X, P and m are defined as above, the resulting compound of formula (VIC) is reacted with a compound of formula (V):

(V)

wherein $R_9$ represents methyl or tolyl, to produce a compound of formula (IV):

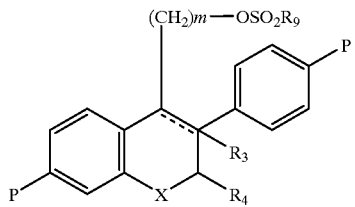
(IV)

wherein ----, $R_3$, $R_4$, X, P, m and $R_9$ are defined as above, the compound of formula (IV) is reacted with a compound of formula (III):

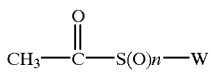
(III)

wherein W represents $R_5$ or

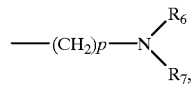

wherein $R_5$, $R_6$, $R_7$, n and p are defined as in formula (I), to produce a compound of formula (II):

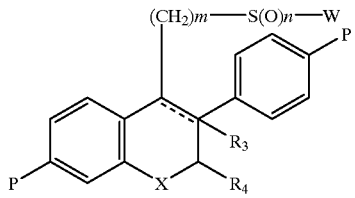
(II)

wherein ----, $R_3$, $R_4$, X, W, P, m and n are defined as above, and the resulting compound of formula (II) is deprotected to produce a compound of formula (Ia):

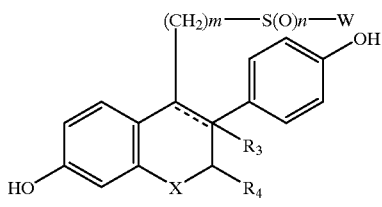
(Ia)

wherein ----, $R_3$, $R_4$, X, W, m and n are defined as above, or the resulting compound of formula (Ia) is esterified or alkylated to produce a compound of formula (Ib):

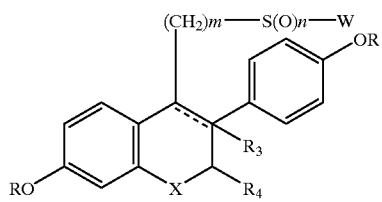
(Ib)

wherein ----, R, $R_3$, $R_4$, X, W, m and n are defined as above.

7. A process for preparing the compound of formula (I):

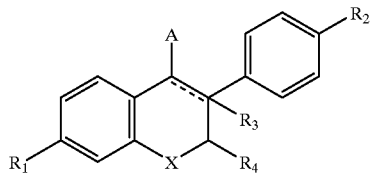
(I)

and salt thereof, in which
----- represents a single bond or a double bond;
$R_1$ and $R_2$ independently of one another represent hydrogen, hydroxy or OR group, wherein R represents acyl or alkyl;
$R_3$ represents hydrogen, lower alkyl or halogeno lower alkyl, provided that when ----- represents a double bond, $R_3$ is not present;
$R_4$ represents hydrogen or lower alkyl;
A represents a group of formula (a), (b), (c) or (d);

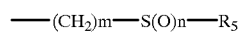 (a)

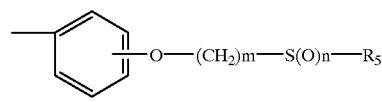 (b)

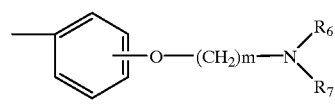 (c)

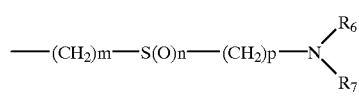 (d)

$R_5$, $R_6$ and $R_7$ independently of one another represent hydrogen, alkyl, halogenoalkyl, alkenyl or halogenoalkenyl, or
$R_6$ and $R_7$ together with nitrogen atom to which they are bound can form a 4- to 8-membered heterocyclic ring which can be substituted with $R_5$;
X represents O, S or $NR_8$, wherein $R_8$ represents hydrogen or lower alkyl;
m denotes an integer of 2 to 15;
n denotes an integer of 0 to 2; and
p denotes an integer of 0 to 4,
characterized in that a compound of formula (VIII):

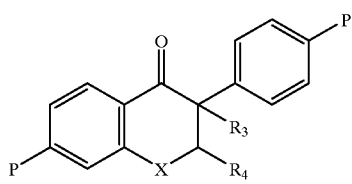
(VIII)

wherein $R_3$, $R_4$ and X are defined as above and P represents hydrogen or protected hydroxy group, is reacted with a compound of formula (XIV):

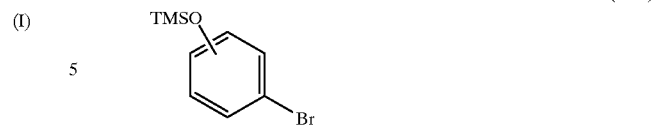
(XIV)

wherein TMS means trimethylsilyl group, to produce a compound of formula (XIII):

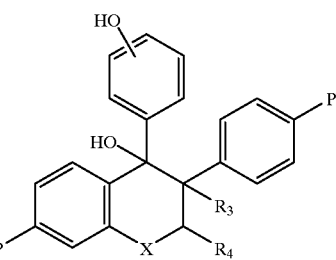
(XIII)

wherein $R_3$, $R_4$, X and P are defined as above, the resulting compound of formula (XIII) is reacted with a compound of formula (XII):

$Z(CH_2)mY$ (XII)

wherein Z represents halogen, Y represents halogen or hydroxy and m is defined as above, to produce a compound of formula (XI):

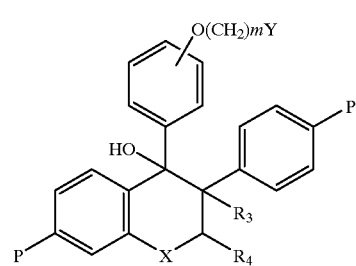
(XI)

wherein $R_3$, $R_4$, X, P, Y and m are defined as above, the resulting compound of formula (XI) is reacted with a compound of formula (IIIa):

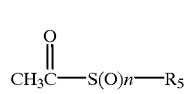
(IIIa)

wherein $R_5$ and n are defined as above, to produce a compound of formula (X):

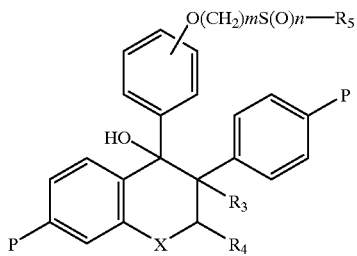

wherein $R_3$, $R_4$, $R_5$, X, P, m and n are defined as above, and the resulting compound of formula (X) is deprotected to produce a compound of formula (Ic):

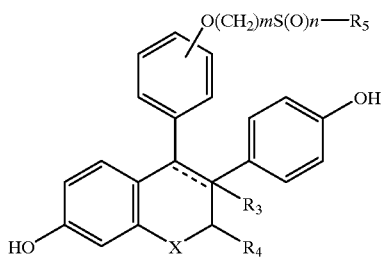

wherein -----, $R_3$, $R_4$, $R_5$, X, m and n are defined as above, or the resulting compound of formula (Ic) is esterified or alkylated to produce a compound of formula (Id):

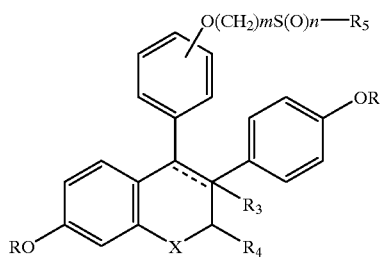

wherein -----, R, $R_3$, $R_4$, $R_5$, X, m and n are defined as above.

8. A process for preparing the compound of formula (I):

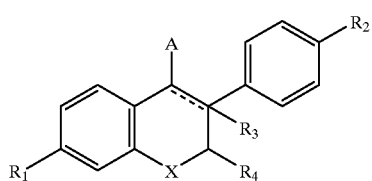

and salt thereof, in which
- ----- represents a single bond or a double bond;
- $R_1$ and $R_2$ independently of one another represent hydrogen, hydroxy or OR group, wherein R represents acyl or alkyl;
- $R_3$ represents hydrogen, lower alkyl or halogeno lower alkyl, provided that when ----- represents a double bond, $R_3$ is not present;
- $R_4$ represents hydrogen or lower alkyl;

A represents a group of formula (a), (b), (c) or (d);

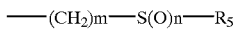

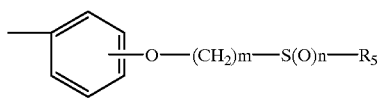

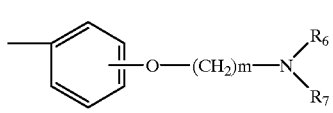

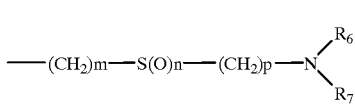

$R_5$, $R_6$ and $R_7$ independently of one another represent hydrogen, alkyl, halogenoalkyl, alkenyl or halogenoalkenyl, or $R_6$ and $R_7$ together with nitrogen atom to which they are bound can form a 4- to 8-membered heterocyclic ring which can be substituted with $R_5$;

X represents O, S or $NR_8$, wherein $R_8$ represents hydrogen or lower alkyl;

m denotes an integer of 2 to 15;

n denotes an integer of 0 to 2; and p denotes an integer of 0 to 4, characterized in that a compound of formula (XI):

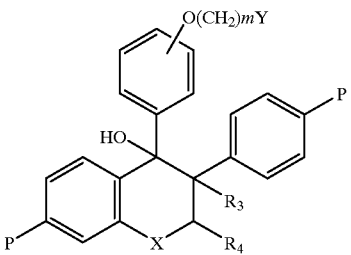

wherein $R_3$, $R_4$, X and m are defined as above, Y represents halogen or hydroxy and P represents hydrogen or protected hydroxy group, is reacted with a compound of formula (XVI):

wherein $R_6$ and $R_7$ are defined as above, to produce a compound of formula (XV):

83

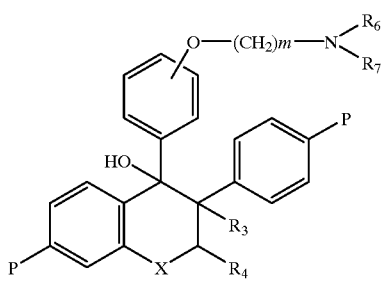

(XV)

wherein $R_3, R_4, R_6, R_7, X, P$ and m are defined as above, and the resulting compound of formula (XV) is deprotected to produce a compound of formula (Ie):

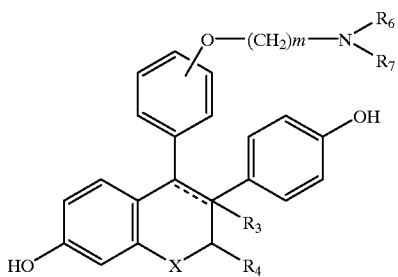

(Ie)

wherein -----, $R_3, R_4, R_6, R_7, X$ and m are defined as above, or the resulting compound of formula (Ie) is esterified or alkylated to produce a compound of formula (If):

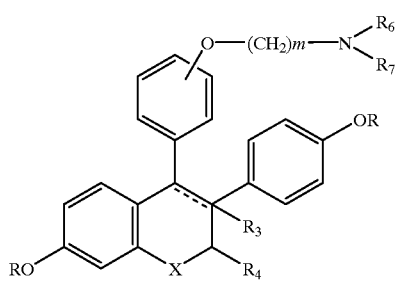

(If)

wherein -----, R, $R_3, R_4, R_6, R_7, X$ and m are defined as above.

9. A process for preparing the compound of formula (Ig):

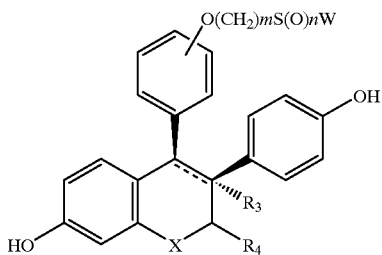

(Ig)

and salt thereof, in which
$R_3$ represents hydrogen, lower alkyl or halogeno lower alkyl;

84

$R_4$ represents hydrogen or lower alkyl;

W represents $R_5$ or

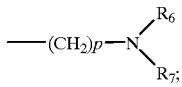

$R_5, R_6$ and $R_7$ independently of one another represent hydrogen, alkyl, halogenoalkyl, alkenyl or halogenoalkenyl, or $R_6$ and $R_7$ together with nitrogen atom to which they are bound an form a 4- to 8-membered heterocyclic ring which can be substituted with $R_5$;

X represents O, S or $NR_8$, wherein $R_8$ represents hydrogen or lower alkyl;

m denotes an integer of 2 to 15;

n denotes an integer of 0 to 2; and p denotes an integer of 0 to 4, characterized in that a compound of formula (VIII):

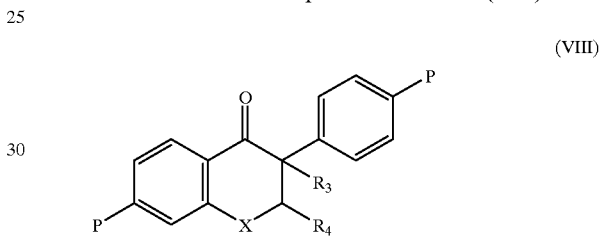

(VIII)

wherein $R_3, R_4$ and X are defined as above and P represents hydrogen or protected hydroxy group, is reacted with a compound of formula (XVI):

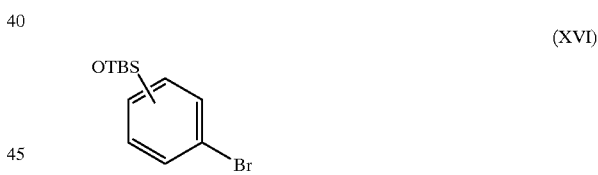

(XVI)

wherein TBS means t-butyldimethylsilyl group, to produce a compound of formula (XVII):

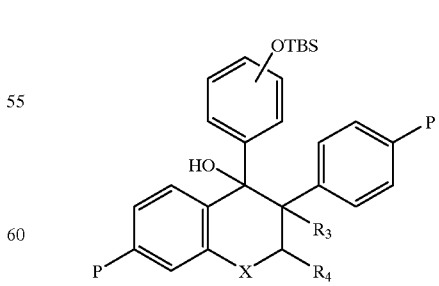

(XVII)

wherein $R_3, R_4, X, P$ and TBS are defined as above, the resulting compound of formula (XVII) is reduced to produce a compound of formula (XVIII):

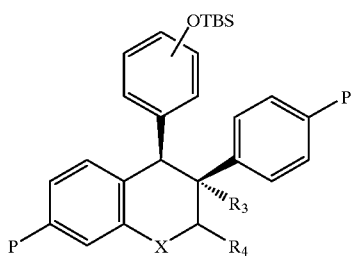
(XVIII)

wherein $R_3$, $R_4$, X, P and TBS are defined as above, the resulting compound of formula (XVIII) is deprotected to produce a compound of formula (XIX):

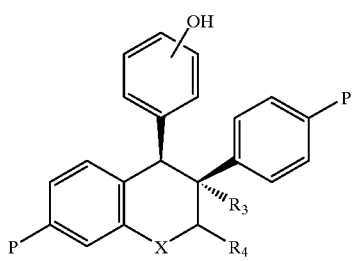
(XIX)

wherein $R_3$, $R_4$, X and P are defined as above, the resulting compound of formula (XIX) is reacted with a compound of formula (XX):

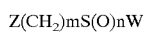
$Z(CH_2)mS(O)nW$ (XX)

wherein W, m and n are defined as above and Z represents halogen, to produce a compound of formula (XXI):

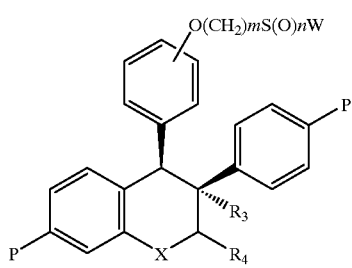
(XXI)

wherein $R_3$, $R_4$, X, P, W, m and n are defined as above, and the resulting compound of formula (XIX) is deprotected to produce a compound of formula (Ig).

10. A process for preparing a compound of formula (XX):

Z—(CH$_2$)mS(O)n—W (XX)

in which
  W represents $R_5$ or

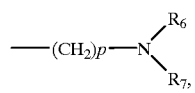

$R_5$, $R_6$ and $R_7$ independently of one another represent hydrogen, alkyl, halogenoalkyl, alkenyl or halogenoalkenyl, or $R_6$ and $R_7$ together with nitrogen atom to which they are bound can form a 4- to 8-membered heterocyclic ring which can be substituted with $R_5$;

Z represents halogen m denotes an integer of 2 to 15;

n denotes an integer of 0 to 2; and p denotes an integer of 0 to 4, characterized in that a compound of formula (XXII):

Y(CH$_2$)mZ (XXII)

wherein Y represents halogen or hydroxy and Z and m are defined as above, is reacted with a compound of formula (XXIII):

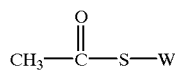
(XXIII)

wherein W is defined as above, to produce a compound of formula (XXIV):

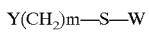
Y(CH$_2$)m—S—W (XXIV)

wherein W, Y and m are defined as above; and the resulting compound of formula (XXIV) is then oxidized to produce the compound of formula (XX).

11. A process for preparing a compound of formula (XXVIII) or (XXIX):

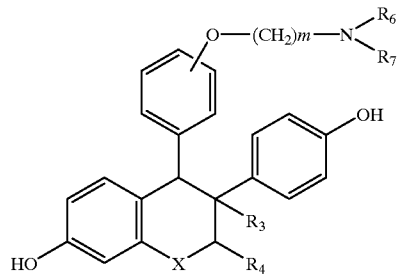
(XXVIII)

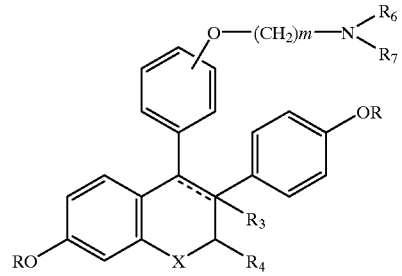
(XXIX)

in which
  ----- represents a single bond or a double bond;
  R represents acyl or alkyl;
  $R_3$ represents hydrogen, lower alkyl or halogeno lower alkyl, provided that
    when ----- represents a double bond, $R_3$ is not present;
  $R_4$ represents hydrogen or lower alkyl;
  $R_6$ and $R_7$ independently of one another represent hydrogen, alkyl, halogenoalkyl, alkenyl or halogenoalkenyl, or $R_6$ and $R_7$ together with nitrogen atom to which they are bound can form a 4- to 8-membered heterocyclic ring which can be substituted with $R_5$;

X represents O, S or $NR_8$, wherein $R_8$ represents hydrogen or lower alkyl; and m denotes an integer of 2 to 15, characterized in that a compound of formula (XXV):

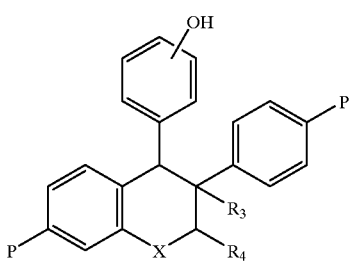

(XXV)

wherein $R_3$, $R_4$ and X are defined as above and P represents hydrogen or protected hydroxy group, is reacted with a compound of formula (XII):

 (XII)

wherein Z represents halogen, Y represents halogen or hydroxy and m is defined as above, to produce a compound of formula (XXVI):

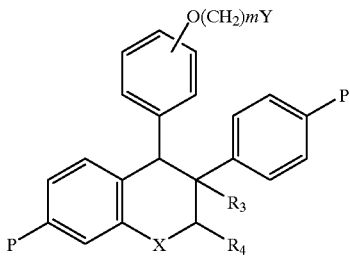

(XXVI)

wherein $R_3$, $R_4$, X, P, Y and m are defined as above, the resulting compound of formula (XXVI) is reacted with a compound of formula (XVI):

(XVI)

wherein $R_6$ and $R_7$ are defined as above, to produce a compound of formula (XVVII):

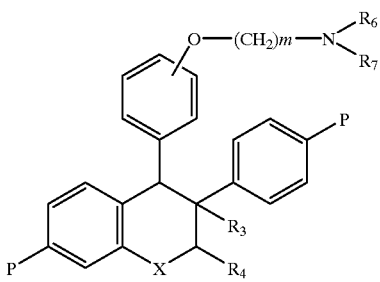

(XXVII)

wherein $R_3$, $R_4$, $R_6$, $R_7$, X, P and m are defined as above, and the resulting compound of formula (XV) is deprotected to produce a compound of formula (XXVIII), or the resulting compound of formula (XXVIII) is esterified or alkylated to produce a compound of formula (XXIX).

12. A process for preparing a compound of formula (6):

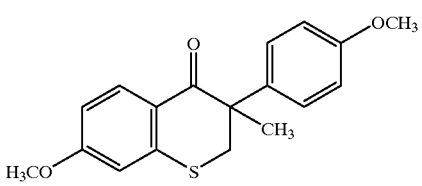

(6)

characterized in that a compound of formula (1):

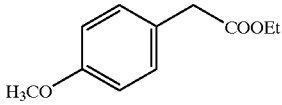

(1)

is reacted with oxalic acid diethyl ester and sodium hydride to produce a compound of formula (2):

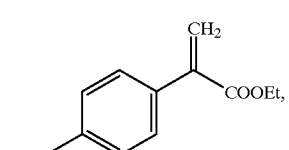

(2)

the resulting compound of formula (2) is reacted with 3-methoxybenzenethiol represented by the formula:

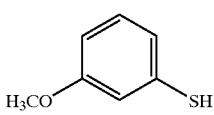

to produce a compound of formula (3):

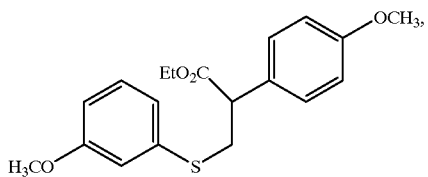
(3)

the resulting compound of formula (3) is reacted with hydrochloric acid to produce a compound of formula (4):

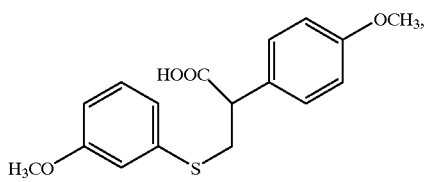
(4)

the compound of formula formula (4) is then cyclized to produce a compound of formula (5):

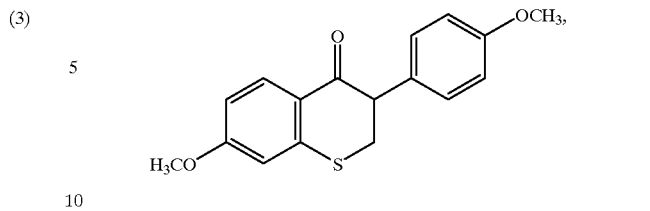
(5)

and the compound of formula (5) is reacted with methyl iodide in the presence of lithium diisopropylamide to produce the compound of formula (6).

13. An anti-estrogenic pharmaceutical composition containing the compound of formula (I) according to anyone of claims 1 to 5, as an active component.

14. The benzofuran derivative of claim 1 wherein when X represents O, $R_3$ is not hydrogen.

15. The benzofuran derivative of claim 2 wherein when X represents O, $R_3$ is not hydrogen.

16. The benzofuran derivative of claim 3 wherein when X represents O, $R_3$ is not hydrogen.

* * * * *